US011926817B2

(12) United States Patent
Eldridge et al.

(10) Patent No.: US 11,926,817 B2
(45) Date of Patent: Mar. 12, 2024

(54) MICROFLUIDIC APPARATUS AND METHODS OF USE THEREOF

(71) Applicant: Nutcracker Therapeutics, Inc., Emeryville, CA (US)

(72) Inventors: Benjamin Eldridge, Danville, CA (US); Ximiao Wen, Hayward, CA (US)

(73) Assignee: NUTCRACKER THERAPEUTICS, INC., Emeryville, CA (US)

(*) Notice: Subject to any disclaimer, the term of this patent is extended or adjusted under 35 U.S.C. 154(b) by 522 days.

(21) Appl. No.: 16/989,824

(22) Filed: Aug. 10, 2020

(65) Prior Publication Data

US 2021/0039106 A1 Feb. 11, 2021

Related U.S. Application Data

(60) Provisional application No. 62/914,374, filed on Oct. 11, 2019, provisional application No. 62/885,170, (Continued)

(51) Int. Cl.

| | |
|---|---|
| ***G01N 21/01*** | (2006.01) |
| ***B01J 19/00*** | (2006.01) |
| ***B01L 3/00*** | (2006.01) |
| ***C12M 1/36*** | (2006.01) |
| ***C12N 15/10*** | (2006.01) |

(52) U.S. Cl.

CPC ........ *C12N 15/101* (2013.01); *B01J 19/0046* (2013.01); *B01J 19/0093* (2013.01); *B01L 3/502769* (2013.01); *C12M 41/48* (2013.01); *G01N 21/01* (2013.01); *B01J 2219/00313* (2013.01); *B01J 2219/00333* (2013.01); *B01J 2219/00722* (2013.01); *B01J 2219/00759* (2013.01); *B01L 2400/0487* (2013.01); *G01N 2021/0187* (2013.01)

(58) Field of Classification Search

CPC .. C12N 15/101; A61P 35/00; B01L 3/502707; B01L 3/502769; B01L 2400/0487; C12M 41/48; G01N 21/01; G01N 2021/0187

See application file for complete search history.

(56) References Cited

U.S. PATENT DOCUMENTS 1,127,434 A 2/1915 Greve
1,670,252 A 5/1928 Gardner
(Continued)

FOREIGN PATENT DOCUMENTS

AU 2016202045 A1 * 4/2016
CA 2836577 A1 * 11/2012 ........... C12Q 1/6809
(Continued)

OTHER PUBLICATIONS

RU_2627927_C2 Translated Version (Year: 2017).*
(Continued)

*Primary Examiner* — Jennifer Wecker
*Assistant Examiner* — Ali Husain Faraz
(74) *Attorney, Agent, or Firm* — FROST BROWN TODD LLP

(57) ABSTRACT

Apparatuses and methods are described herein for processing polynucleotides in a sealed path environment. The apparatuses include optical sensors to monitor operations and to track material usage for good manufacturing practice.

38 Claims, 27 Drawing Sheets

Related U.S. Application Data filed on Aug. 9, 2019, provisional application No. 62/885,159, filed on Aug. 9, 2019.

(56) References Cited

U.S. PATENT DOCUMENTS 5,334,525 A 8/1994 Seeger
5,360,714 A 11/1994 Seeger
5,691,140 A 11/1997 Noren et al.
5,773,244 A 6/1998 Ares et al.
5,837,852 A 11/1998 Chung et al.
5,843,723 A 12/1998 Dubensky et al.
5,849,891 A 12/1998 Lin et al.
5,871,744 A 2/1999 Vakharia et al.
5,922,591 A 7/1999 Anderson et al.
6,156,883 A 12/2000 Estes et al.
6,190,666 B1 2/2001 Garoff et al.
6,197,554 B1 3/2001 Lin et al.
6,228,580 B1 5/2001 Blumenfeld et al.
6,231,868 B1 5/2001 Vakharia et al.
6,271,002 B1 8/2001 Linsley et al.
6,274,147 B1 8/2001 Vakharia et al.
6,303,299 B1 10/2001 Hecht et al.
6,379,897 B1 4/2002 Weidenhammer et al.
6,408,878 B2 6/2002 Unger et al.
6,511,832 B1 1/2003 Guarino et al.
6,558,902 B1 5/2003 Hillenkamp
6,582,938 B1 6/2003 Su et al.
6,620,587 B1 9/2003 Taussig et al.
6,733,994 B2 5/2004 Weiner et al.
6,794,138 B1 9/2004 Cao et al.
6,893,866 B1 5/2005 Westaway et al.
6,942,865 B2 9/2005 Estes et al.
6,951,725 B2 10/2005 Kurz et al.
6,955,876 B2 10/2005 Kane et al.
6,977,150 B2 12/2005 Forster et al.
7,011,958 B2 3/2006 Watzele et al.
7,063,946 B2 6/2006 Kenten et al.
7,118,883 B2 10/2006 Inoue et al.
7,241,605 B1 7/2007 Narimatsu et al.
7,371,540 B2 5/2008 Barber
7,405,062 B2 7/2008 Ji
7,413,856 B2 8/2008 Henkin et al.
7,659,391 B2 2/2010 De Backer et al.
7,794,939 B2 9/2010 Maki et al.
7,807,407 B2 10/2010 Garvin et al.
7,820,427 B2 10/2010 Unger et al.
8,357,529 B2 1/2013 Swartz et al.
8,557,518 B2 10/2013 Jovanovich et al.
8,580,494 B2 11/2013 Ginsberg et al.
8,859,229 B2 10/2014 Rabinovich et al.
8,945,861 B2 2/2015 Bomgarden et al.
9,090,928 B2 7/2015 Park et al.
9,206,216 B2 12/2015 Etienne et al.
9,249,423 B2 2/2016 Rabinovich et al.
9,410,148 B2 8/2016 Suga et al.
9,506,845 B2 11/2016 Fowler et al.
9,574,167 B2 2/2017 Lee et al.
9,637,739 B2 5/2017 Siksnys
9,701,993 B2 7/2017 Suga et al.
9,738,908 B2 8/2017 Wu
9,951,349 B2 4/2018 Rabinovich et al.
10,113,168 B2 10/2018 Golden et al.
10,118,950 B2 11/2018 Jewett et al.
10,155,038 B2 12/2018 Rabinovich et al.
10,201,620 B2 2/2019 Meis et al.
10,227,630 B2 3/2019 Sorek et al.
2001/0036672 A1 11/2001 Anderson et al.
2001/0039014 A1 11/2001 Bass et al.
2002/0029113 A1 3/2002 Wang et al.
2002/0081619 A1 6/2002 Bastian et al.
2002/0119484 A1 8/2002 Weidenhammer et al.
2002/0168706 A1 11/2002 Chatterjee et al.
2002/0197685 A1 12/2002 Zhou
2003/0003465 A1 1/2003 Little et al.
2003/0017453 A1 1/2003 Roberts et al.
2003/0119027 A1 6/2003 Roberts et al.
2003/0134272 A1 7/2003 Messiaen et al.
2003/0186237 A1 10/2003 Ginsberg et al.
2003/0224389 A1 12/2003 Bastian et al.
2004/0014043 A1 1/2004 Levison et al.
2004/0076966 A1 4/2004 Windsor et al.
2004/0036884 A1 5/2004 Beach et al.
2004/0086906 A1 5/2004 Takiguchi
2004/0110135 A1 6/2004 Nemetz et al.
2004/0110153 A1 6/2004 Dong et al.
2004/0115763 A1 6/2004 Narimatsu et al.
2004/0137572 A1 7/2004 Finney et al.
2004/0161748 A1 8/2004 He et al.
2004/0175719 A1 9/2004 Christians
2004/0185443 A1 9/2004 Dahl
2004/0191756 A1 9/2004 Matthias et al.
2004/0214223 A1 10/2004 Cao et al.
2004/0224328 A1 11/2004 Prydz et al.
2005/0003369 A1 1/2005 Christians et al.
2005/0003392 A1 1/2005 Salceda et al.
2005/0032086 A1 2/2005 Sakanyan et al.
2005/0048549 A1 3/2005 Cao et al.
2005/0064421 A1 3/2005 Gehrmann et al.
2005/0095626 A1 5/2005 Komazawa et al.
2005/0100946 A1 5/2005 Lipshutz et al.
2005/0123910 A1 6/2005 Cookson et al.
2005/0176930 A1 8/2005 Coy et al.
2006/0014169 A1 1/2006 Fiandt et al.
2006/0099602 A1 5/2006 Tajima et al.
2006/0110733 A1 5/2006 Toohey et al.
2006/0246434 A1 11/2006 Erlander et al.
2007/0077572 A1 4/2007 Tawfik et al.
2007/0154906 A1 7/2007 Martin et al.
2007/0248578 A1 10/2007 Tcherepanova
2007/0256148 A1 11/2007 Katz et al.
2007/0256149 A1 11/2007 Katz et al.
2007/0281336 A1 12/2007 Jendrisak et al.
2007/0292868 A1 12/2007 Madejon Seiz et al.
2008/0038727 A1 2/2008 Spier
2008/0145845 A1 6/2008 Remacle et al.
2008/0275219 A1 11/2008 Green et al.
2008/0281090 A1 11/2008 Lee et al.
2008/0305961 A1 12/2008 Abu Khabar
2009/0029353 A1 1/2009 Maki et al.
2009/0042244 A1 2/2009 Voloshin et al.
2009/0155854 A1 6/2009 Yueh et al.
2009/0162832 A1 6/2009 Brugidou et al.
2009/0221444 A1 9/2009 Borlak et al.
2009/0226899 A1 9/2009 Chen
2009/0286852 A1 11/2009 Kariko et al.
2009/0291854 A1 11/2009 Wiesinger-Mayr et al.
2010/0008935 A1 1/2010 Borlak et al.
2010/0047261 A1 2/2010 Hoerr et al.
2010/0069255 A1 3/2010 Borlak et al.
2010/0189729 A1 7/2010 Hoerr et al.
2010/0196788 A1 8/2010 Enomura
2010/0260717 A1 10/2010 Einav et al.
2010/0304378 A1 12/2010 Griffiths et al.
2011/0064739 A1 3/2011 Borlak et al.
2011/0155667 A1 6/2011 Charest et al.
2012/0164036 A1* 6/2012 Stern .................. B01L 3/50273 422/502
2012/0196278 A1 8/2012 Jendrisak et al.
2012/0245042 A1 9/2012 Liu et al.
2013/0040840 A1 2/2013 Huang et al.
2013/0129754 A1 5/2013 Thess et al.
2013/0132006 A1* 5/2013 Gwynn .................. B01L 3/021 702/55
2013/0156849 A1 6/2013 de Fougerolles et al.
2013/0189741 A1 7/2013 Meis et al.
2013/0266640 A1 10/2013 de Fougerolles et al.
2014/0227300 A1 8/2014 Chin et al.
2014/0256589 A1 9/2014 Fabrizio
2014/0335561 A1 11/2014 Park et al.
2014/0378538 A1 12/2014 Bancel
2015/0050699 A1 2/2015 Siksnys et al.
2016/0122727 A1 5/2016 Heartlein et al.
2016/0193299 A1 7/2016 de Fougerolles et al.
2016/0228841 A2 8/2016 Fan et al.

(56) References Cited

U.S. PATENT DOCUMENTS

| | | | |
|---|---|---|---|
| 2016/0244829 | A1 | 8/2016 | Bang et al. |
| 2016/0304854 | A1 | 10/2016 | Izpisua Belmonte et al. |
| 2016/0369248 | A1 | 12/2016 | Richardson et al. |
| 2017/0107566 | A1 | 4/2017 | Church et al. |
| 2017/0183664 | A1 | 6/2017 | Lucks et al. |
| 2017/0343539 | A1 | 11/2017 | Epstein et al. |
| 2018/0010179 | A1 | 1/2018 | Hansen et al. |
| 2018/0085391 | A1 | 3/2018 | Bouchon et al. |
| 2018/0142275 | A1 | 5/2018 | Roos et al. |
| 2018/0171340 | A1 | 6/2018 | Kamrud et al. |
| 2018/0223274 | A1 | 8/2018 | Townshend et al. |
| 2018/0237847 | A1 | 8/2018 | Culler et al. |
| 2018/0237849 | A1 | 8/2018 | Thompson |
| 2018/0245242 | A1 | 8/2018 | Schendel et al. |
| 2018/0256748 | A1 | 9/2018 | Angel et al. |
| 2018/0291413 | A1 | 10/2018 | Chiocchini et al. |
| 2019/0002906 | A1 | 1/2019 | Limphong et al. |
| 2019/0002943 | A1 | 1/2019 | Mazutis et al. |
| 2019/0009274 | A1 * | 1/2019 | Novak ............... G01N 33/5088 |
| 2019/0010485 | A1 | 1/2019 | Yazdan Panah et al. |
| 2019/0071484 | A1 | 3/2019 | Uckert et al. |
| 2019/0071704 | A1 | 3/2019 | Nelson et al. |
| 2019/0106698 | A1 | 4/2019 | Kim |
| 2019/0127731 | A1 | 5/2019 | McDermott |
| 2019/0144480 | A1 | 5/2019 | DeRosa et al. |
| 2019/0153425 | A1 | 5/2019 | Baiersdorfer et al. |
| 2019/0168221 | A1 | 6/2019 | Sollier et al. |

FOREIGN PATENT DOCUMENTS

| | | | | |
|---|---|---|---|---|
| EP | 0315254 | A1 | 5/1989 | |
| EP | 0965635 | A1 | 12/1999 | |
| EP | 1103604 | A1 | 5/2001 | |
| EP | 1197556 | A1 | 4/2002 | |
| EP | 0934331 | B1 | 11/2002 | |
| EP | 1316616 | A1 | 6/2003 | |
| EP | 1137801 | B1 | 2/2004 | |
| EP | 1426442 | A1 | 6/2004 | |
| EP | 1681347 | A1 | 7/2006 | |
| EP | 1892302 | A1 | 2/2008 | |
| EP | 1540009 | B1 | 9/2011 | |
| EP | 2669291 | A1 | 12/2013 | |
| EP | 3061826 | A1 | 8/2016 | |
| EP | 2970955 | B1 | 11/2018 | |
| EP | 2802417 | B1 | 5/2019 | |
| JP | 2009183876 | A | 8/2009 | |
| KR | 10-2009-106089 | A | 10/2009 | |
| RU | 2627927 | C2 * | 8/2017 | ............ B01L 3/0275 |
| WO | WO89/002472 | A1 | 3/1989 | |
| WO | WO90/012107 | A1 | 10/1990 | |
| WO | WO92/002536 | A1 | 2/1992 | |
| WO | WO92/007949 | A1 | 5/1992 | |
| WO | WO92/010578 | A1 | 6/1992 | |
| WO | WO94/005700 | A2 | 3/1994 | |
| WO | WO94/009127 | A2 | 4/1994 | |
| WO | WO95/011922 | A1 | 5/1995 | |
| WO | WO95/027044 | A1 | 10/1995 | |
| WO | WO95/027069 | A1 | 10/1995 | |
| WO | WO97/002357 | A1 | 1/1997 | |
| WO | WO98/008953 | A1 | 3/1998 | |
| WO | WO99/011821 | A1 | 3/1999 | |
| WO | WO99/031267 | A1 | 6/1999 | |
| WO | WO99/047650 | A2 | 9/1999 | |
| WO | WO99/050419 | A2 | 10/1999 | |
| WO | WO99/057318 | A2 | 11/1999 | |
| WO | WO00/005366 | A2 | 2/2000 | |
| WO | WO00/34513 | A1 | 6/2000 | |
| WO | WO00/045840 | A1 | 8/2000 | |
| WO | WO00/075356 | A1 | 12/2000 | |
| WO | WO01/051663 | A2 | 7/2001 | |
| WO | WO01/057073 | A2 | 8/2001 | |
| WO | WO02/016426 | A2 | 2/2002 | |
| WO | WO02/029088 | A2 | 4/2002 | |
| WO | WO02/036828 | A2 | 5/2002 | |
| WO | WO02/059293 | A2 | 8/2002 | |
| WO | WO02/065093 | A2 | 8/2002 | |
| WO | WO02/072890 | A1 | 9/2002 | |
| WO | WO03/000727 | A2 | 1/2003 | |
| WO | WO03/000856 | A2 | 1/2003 | |
| WO | WO03/022028 | A2 | 3/2003 | |
| WO | WO03/037302 | A1 | 5/2003 | |
| WO | WO03/062394 | A2 | 7/2003 | |
| WO | WO03/102587 | A1 | 12/2003 | |
| WO | WO2004/007677 | A2 | 1/2004 | |
| WO | WO2004/007684 | A2 | 1/2004 | |
| WO | WO2004/039953 | A2 | 5/2004 | |
| WO | WO2004/063375 | A1 | 7/2004 | |
| WO | WO2005/012487 | A2 | 2/2005 | |
| WO | WO2005/015156 | A2 | 2/2005 | |
| WO | WO2005/060697 | A2 | 7/2005 | |
| WO | WO2005/100585 | A2 | 10/2005 | |
| WO | WO2005/118857 | A2 | 12/2005 | |
| WO | WO2006/002283 | A1 | 1/2006 | |
| WO | WO2006/019876 | A2 | 2/2006 | |
| WO | WO2006/022712 | A1 | 3/2006 | |
| WO | WO2006/091892 | A2 | 8/2006 | |
| WO | WO2007/120166 | A2 | 10/2007 | |
| WO | WO2007/120863 | A2 | 10/2007 | |
| WO | WO2008/009751 | A2 | 1/2008 | |
| WO | WO2008/091283 | A2 | 7/2008 | |
| WO | WO2008/097926 | A2 | 8/2008 | |
| WO | WO2009/053679 | A1 | 4/2009 | |
| WO | WO2012/019630 | A1 | 2/2012 | |
| WO | WO2013/086008 | A1 | 6/2013 | |
| WO | WO2013/090648 | A1 | 6/2013 | |
| WO | WO2013/136095 | A1 | 9/2013 | |
| WO | WO2014/013067 | A1 | 1/2014 | |
| WO | WO2014/062036 | A1 | 4/2014 | |
| WO | WO2014/071978 | A1 | 5/2014 | |
| WO | WO2014/075083 | A1 | 5/2014 | |
| WO | WO2016/014409 | A1 | 1/2016 | |
| WO | WO2016/168763 | A1 | 10/2016 | |
| WO | WO2016/187531 | A1 | 11/2016 | |
| WO | WO2016/207300 | A1 | 12/2016 | |
| WO | WO2017/109134 | A1 | 6/2017 | |
| WO | WO2017/124034 | A1 | 7/2017 | |
| WO | WO2017143894 | A1 | 8/2017 | |
| WO | WO2017/162297 | A1 | 9/2017 | |
| WO | WO2017/173105 | A1 | 10/2017 | |
| WO | WO2017/173354 | A2 | 10/2017 | |
| WO | WO2017/201352 | A1 | 11/2017 | |
| WO | WO2017/218881 | A1 | 12/2017 | |
| WO | WO2018/005445 | A1 | 1/2018 | |
| WO | WO2018/005720 | A1 | 1/2018 | |
| WO | WO2018/035158 | A1 | 2/2018 | |
| WO | WO2018/035377 | A1 | 2/2018 | |
| WO | WO2018/053209 | A1 | 3/2018 | |
| WO | WO2018/053414 | A1 | 3/2018 | |
| WO | 2018089799 | A1 | 5/2018 | |
| WO | WO2018/081462 | A1 | 5/2018 | |
| WO | WO2018/106615 | A2 | 6/2018 | |
| WO | WO2018/125982 | A1 | 7/2018 | |
| WO | WO2018165159 | A1 | 9/2018 | |
| WO | WO2018/204854 | A1 | 11/2018 | |
| WO | WO2018/208856 | A1 | 11/2018 | |
| WO | WO2018/209092 | A1 | 11/2018 | |
| WO | WO2018/211038 | A1 | 11/2018 | |
| WO | WO2018/219093 | A1 | 12/2018 | |
| WO | WO2018/222890 | A1 | 12/2018 | |
| WO | WO2019/025984 | A1 | 2/2019 | |
| WO | WO2019/033095 | A1 | 2/2019 | |
| WO | WO2019/036683 | A1 | 2/2019 | |
| WO | WO2019/036685 | A1 | 2/2019 | |
| WO | WO2019/068066 | A1 | 4/2019 | |
| WO | WO2019/073055 | A1 | 4/2019 | |
| WO | WO2019/084043 | A1 | 5/2019 | |
| WO | WO2021/133765 | A1 | 7/2021 | |

OTHER PUBLICATIONS

Haslam et al., “Microfluidic reflow pumps”, Biomicrofluidics, Jul. 9, 2015, 9, 044104.

(56) References Cited

OTHER PUBLICATIONS

Chen et al.; Rapid discovery of potent siRNA-containing lipid nanoparticles enabled by controlled microfluidic formulation; Journal of the American Chemical Society; 134(16); pp. 6948-6951; 2 pages (Abstract Only) Apr. 2012.
Kimura et al.; Development of the iLiNP device: fine tuning the lipid nanoparticle size within 10 nm for drug delivery; ACS Omega; 3(5); pp. 5044-5051; May 2018.
Van Hoecke et al.; How mRNA therapeutics are entering the monoclonal antibody field; Journal of Translational Medicine; 17(1); pp. doi.org/10.1186/s12967-019-1804-8; 14 pages; Dec. 2019.
Deutsch et al.; U.S. Appl. No. 16/989,833 entitled "Methods and apparatuses for manufacturing for removing material from a therapeutic composition," filed Aug. 10, 2020.

* cited by examiner (top)

(bottom)

MICROFLUIDIC APPARATUS AND METHODS OF USE THEREOF

CROSS REFERENCE TO RELATED APPLICATIONS

This patent application claims priority to U.S. Provisional Patent Application No. 62/885,159, filed on Aug. 9, 2019, and titled "MICROFLUIDIC APPARATUS AND METHODS OF USE THEREOF," as well as U.S. Provisional Patent Application No. 62/885,170, filed Aug. 9, 2019, and titled "METHODS AND APPARATUSES FOR MANUFACTURING THERAPEUTIC COMPOSITIONS," and U.S. Provisional Patent Application No. 62/914,374, filed on Oct. 11, 2019, titled "METHODS AND APPARATUSES FOR MANUFACTURING FOR REMOVING MATERIAL FROM A THERAPEUTIC COMPOSITION," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein may be used for the manufacture and formulation of biomolecule-containing (including therapeutic mRNA) products, particularly therapeutics for individualized care. In particular, described herein are closed path methods and apparatuses for processing therapeutic polynucleotides, including at a point of care.

BACKGROUND

Currently available technologies for manufacturing and formulating polynucleotide therapeutics, particularly mRNA therapeutics, often expose the products to contamination and degradation. Currently available centralized production can be too costly, too slow, and susceptible to contamination for use in therapeutic formulations possibly including multiple polynucleotide species. Development of scalable polynucleotide manufacturing, production of single patient dosages, elimination of touchpoints to limit contamination, input and process tracking for meeting clinical manufacturing requirements, and use in Point-of-Care operations can advance the use of these promising therapeutic modalities. Microfluidic instrumentation and processes can provide major advantages against these goals.

SUMMARY OF THE DISCLOSURE

Described herein are microfluidic apparatuses for manufacturing therapeutics, including in particular mRNA therapeutics. For example, described herein are systems that may form therapeutic materials (including both drug substance and drug product) within a dedicated, single-use, disposable microfluidic path device (e.g., microfluidic path plate device, chip, biochip, plate, etc.). Microfluidic path devices and control systems for operating microfluidic path devices are described.

For example described herein are control systems ("apparatuses") for operating a microfluidic path device. These apparatuses may be referred to herein as microfluidic apparatuses, microfluidic control apparatuses, microfluidic control systems, or microfluidic systems.

A microfluidic apparatus may include: a seating mount (e.g., seat) for a microfluidic path device; a plurality of fluid vials, wherein each fluid vial either comprises a fluidic line or is configured to couple with a fluidic line, to form a closed fluid path; and a controller configured to drive fluidic movement in the microfluidic path device when the microfluidic path device is seated in the seating mount. In any of these microfluidic apparatuses, each fluidic line may be configured to be sealed against the microfluidic path device seated in the seating mount to form a closed fluid path. The microfluidic apparatuses described herein may advantageously include any (or any combination of) the features described herein.

For example, a microfluidic apparatus may include: a seating mount for a microfluidic path device; a reagent storage frame comprising a plurality of holders each configured to hold a fluid vial, wherein each fluid vial either comprises a fluidic line or is configured to couple with a fluidic line, further wherein each fluidic line is configured to be biased against the microfluidic path device seated in the seating mount with a bias force; and a controller configured to drive fluidic movement in the microfluidic path device when the microfluidic path device is seated in the seating mount.

A microfluidic apparatus may include: a seating mount for a microfluidic path device; a fluid interface assembly comprising a plurality of fluidic lines, wherein each fluidic line is configured to be separately biased against the microfluidic path device seated in the seating mount with a bias force; a reagent storage frame comprising a plurality of fluid sample holders each configured to hold a fluid vial and each configured to couple to the fluid interface assembly through one of the fluidic lines of the fluid interface assembly; and a controller configured to drive fluidic movement in the microfluidic path device when the microfluidic path device is seated in the seating mount.

A microfluidic apparatus may include a seating mount for a microfluidic path device; a plurality of pressure lines; a reagent storage frame comprising a plurality of holders each configured to hold a fluid vial, wherein each fluid vial either comprises a fluidic line or is configured to couple with a fluidic line, further wherein each fluidic line and each pressure line is configured to be biased against the microfluidic path device seated in the seating mount with a bias force; and a controller configured to control the application of pressure through the pressure lines to drive fluidic movement in the microfluidic path device when the microfluidic path device is seated in the seating mount.

A microfluidic apparatus may include a seating mount for a microfluidic path device; a fluid interface assembly comprising a plurality of fluidic lines and pressure lines, wherein each fluidic line and each pressure line is configured to be biased against the microfluidic path device seated in the seating mount with a bias force; a reagent storage frame comprising a plurality of fluid sample holders each configured to hold a fluid vial and each configured to couple to the fluid interface assembly through one of the fluidic lines of the fluid interface assembly; and a controller configured to control the application of pressure through the pressure lines to drive fluidic movement in the microfluidic path device when the microfluidic path device is seated in the seating mount.

A microfluidic apparatus may include a seating mount for a microfluidic path device; a plurality of pressure lines; a plurality of fluid vials, wherein each fluid vial either comprises a fluidic line or is configured to couple with a fluidic line, further wherein each fluidic line and each pressure line is configured to be seal against the microfluidic path device seated in the seating mount to form a closed fluid path; and a controller configured to control the application of pressure through the pressure lines to drive fluidic movement in the microfluidic path device when the microfluidic path device is seated in the seating mount.

A microfluidic apparatus may include a seating mount for a microfluidic path device; a plurality of fluid vials, wherein each fluid vial either comprises a fluidic line or is configured to couple with a fluidic line, further wherein each fluidic line is configured to be seal against the microfluidic path device seated in the seating mount to form a closed fluid path; at least one optical sensor configured to monitor fluid within the microfluidic path device seated in the seating mount; and a controller configured to drive fluidic movement in the microfluidic path device when the microfluidic path device is seated in the seating mount and to record and/or transmit optical data showing fluid within the microfluidic path during operation of the apparatus.

A microfluidic apparatus may include: a seating mount for a microfluidic path device; a fluid interface assembly comprising a plurality of fluidic lines and pressure lines, wherein each fluidic line and each pressure line is configured to be biased (e.g., spring-loaded) against the microfluidic path device seated in the seating mount; a reagent storage frame comprising a plurality of fluid sample holders each configured to hold a fluid vial and each configured to couple to the fluid interface assembly through one of the fluidic lines of the fluid interface assembly; and a controller configured to control the application of pressure through the pressure lines to drive fluidic movement in the microfluidic path device when the microfluidic path device is seated in the seating mount.

In some variations a microfluidic apparatus for processing therapeutic polynucleotides at a point of care and configured to operate as a closed path, may include: a seating mount for a microfluidic path device; a fluid interface assembly comprising a plurality of fluidic lines and pressure lines, wherein each fluidic line and each pressure line is configured to independently be driven against the microfluidic path device seated in the seating mount to make a sealing connection thereto; a reagent storage frame comprising a plurality of fluid sample holders each configured to hold a fluid and each configured to couple to the fluid interface assembly through one of the fluidic lines of the fluid interface assembly; a controller configured to control the application of pressure through the pressure lines to drive fluidic movement in the microfluidic path device when the microfluidic path device is seated in the seating mount; wherein the fluid interface assembly comprises a plurality of spring biases configured to independently urge each fluidic line against the microfluidic path device seated in the seating mount to make a sealing connection thereto.

For example, an apparatus, (e.g., a microfluidic apparatus for forming a therapeutic polynucleotide) may include: a seating mount for removably holding a microfluidic path device; a plurality of pressure lines; a plurality of fluid vials that are each pressurized by one or more pressure lines from the plurality of pressure lines, further wherein each fluid vial either comprises a fluidic line or is configured to couple with the fluidic line, wherein each fluidic line and at least a subset of the pressure lines are configured to be independently biased against the microfluidic path device seated in the seating mount to form a sealed closed fluid path; and a controller configured to control the application of pressure through the pressure lines to drive fluidic movement in the microfluidic path device when the microfluidic path device is seated in the seating mount and to apply pressure to one or more of the pressure lines to open or close valves in the microfluidic path device during operation.

As mentioned, in general, the controller may be configured to control the apparatus to perform an in vitro transcription (IVT) reaction in the microfluidic path device.

For example, an apparatus (e.g., a microfluidic apparatus for forming a therapeutic polynucleotide, such as a therapeutic mRNA) may include: a seating mount for a microfluidic path device; a plurality of pressure lines; a fluid interface assembly comprising a plurality of fluidic lines; a plurality of fluid vials configured to be pressurized; a reagent storage frame comprising a plurality of holders each configured to hold a fluid vial of the plurality of fluid vials, wherein each fluid vial either comprises a fluidic line of the plurality of fluidic lines, or is configured to couple with a fluidic line of the plurality of fluidic lines, further wherein each fluidic line and at least some of the pressure lines are configured to be separately biased against the microfluidic path device seated in the seating mount with a bias force; and a controller configured to control the application of pressure through the pressure lines to drive fluidic movement in the microfluidic path device when the microfluidic path device is seated in the seating mount.

In some variations, the microfluidic apparatus (e.g., microfluidic apparatus for forming a therapeutic polynucleotide, such as a therapeutic mRNA) may include: a seating mount for removably holding a microfluidic path device; a plurality of pressure lines wherein at least a subset of the pressure lines are configured to be independently biased against a pressure input on the microfluidic path device seated in the seating mount; a plurality of fluid vials configured to be pressurized, further wherein each fluid vial either comprises a fluidic output configured to seal against an input on the microfluidic path device or is configured to couple with a fluidic line that is configured to be independently biased against the microfluidic path device to form a sealed closed fluid path; a first optical detector configured to monitor fluid within the fluid vials; a second optical detector configured to monitor fluid within the microfluidic path device seated in the seating mount; a controller configured to receive input from the first optical detector and the second optical detector and to control the application of pressure through the pressure lines to apply pressure from the plurality of pressure lines to open and/or close valves and to drive fluidic movement in the microfluidic path device based at least in part on the received input.

A microfluidic apparatus for processing therapeutic polynucleotides at a point of care and configured to operate as a closed path may include: a seating mount for a microfluidic path device; a fluid interface assembly comprising a plurality of fluidic lines and pressure lines, wherein each fluidic line and each pressure line is configured to be independently driven against the microfluidic path device seated in the seating mount to make a sealing connection thereto; a reagent storage frame comprising a plurality of pressurized fluid sample holders each configured to hold a fluid vial and each configured to couple to the fluid interface assembly through one of the fluidic lines of the fluid interface assembly; a plurality of optical sensors arranged around the seating mount and reagent storage frame to monitor fluid levels within the fluid vials held by the reagent storage frame and fluidic movement in the microfluidic path device when the microfluidic path device is seated in the seating mount;

and a controller in communication with the optical sensors and configured to control the application of pressure through the pressure lines to drive fluidic movement in the microfluidic path device when the microfluidic path device is seated in the seating mount; wherein the fluid interface assembly comprises a plurality of collets configured to independently urge each fluidic line against the microfluidic path device seated in the seating mount to make a sealing connection thereto, further wherein each of the seating mount, fluid interface assembly and fluid sample holders are configured to be removable for sterilization.

In some variations, these microfluidic apparatuses may be microfluidic apparatuses for forming a therapeutic polynucleotide (e.g., an mRNA therapeutic). The apparatus may include: a seating mount for removably holding a microfluidic path plate device, a plurality of pressure lines; a plurality of fluid vials, wherein each fluid vial either comprises a fluidic line or is configured to couple with the fluidic line, wherein each fluidic line and at least a subset of the pressure lines are configured to be biased against the microfluidic path plate device held in the seating mount to form a closed fluid path; and a controller configured to control the application of pressure through the pressure lines to drive fluidic movement in the microfluidic path plate device when the microfluidic path plate device is held in the seating mount, wherein the controller is configured to direct the synthesis of a synthetic template, direct an in vitro transcription (IVT) reaction using the template to form a therapeutic polynucleotide, and direct purification of the therapeutic polynucleotide in one or more microfluidic path plate devices held in the seating mount.

A microfluidic apparatus (e.g., a microfluidic apparatus for forming a therapeutic polynucleotide, such as a therapeutic mRNA) may include: a seating mount for removably holding a microfluidic path plate device; a plurality of pressure lines; a plurality of fluid vials, wherein each fluid vial either comprises a fluidic line or is configured to couple with the fluidic line, wherein each fluidic line and at least a subset of the pressure lines are configured to be biased against the microfluidic path plate device held in the seating mount to form a closed fluid path; and a controller configured to control the application of pressure through the pressure lines to drive fluidic movement in the microfluidic path plate device when the microfluidic path plate device is held in the seating mount, wherein the controller is configured to determine the contents of the fluid vials, transfer sub-microliter amounts of material from the fluid vials to one or more reactors in the microfluidic path plate device held in the seating mount, direct the synthesis of a synthetic template, direct an in vitro transcription (IVT) reaction using the template to form a therapeutic polynucleotide, and direct purification of the therapeutic polynucleotide in one or more microfluidic path devices held in the seating mount.

The controller be configured to perform any of the method described herein, an in particular may be configured to receive inputs (e.g., optical input, pressure input, temperature/thermal input, etc.) and process the input to control movement of fluid in the microfluidic path device, temperature (including thermocycling) of various regions of the microfluidic path device, rinsing/combining, opening/closing of valve of the microfluidic device, detection of the microfluidic device, etc. The controller may include one or more microprocessors, communication circuitry, memory, etc. The controller may comprise firmware, hardware and/or software.

Any of these apparatuses may include a one or more (e.g., a plurality) of optical sensors arranged around the seating mount and reagent storage frame to monitor fluid levels within the reagent storage frame and fluidic movement in the microfluidic path device when the microfluidic path device is seated in the seating mount. Alternatively or additionally, the optical sensor(s) may be present on the bottom of the apparatus (e.g., beneath the seating mount) and may be directed upwards to detect fluid amounts, movement, etc.). The apparatus may include a seating mount release control configured to release the seating mount from the apparatus so that it can be separately sterilized. Any of these apparatuses may include a fluid interface assembly release control configured to release the fluid interface assembly from the apparatus so that it can be separately sterilized, and/or a fluid sample holder release control configured to release the fluid sample holder from the apparatus so that it can be separately sterilized.

Any of these apparatuses may include a thermal control configured to modulate the temperature of at least one region of the microfluidic path device when the microfluidic path device is seated in the seating mount. In some apparatuses, there may be more than one thermal control configured to modulate the temperature of differing regions of the microfluidic path device. The thermal control may comprise a Peltier device and/or may be configured to control the temperature of the at least one region of the microfluidic path device to between 4° C. to 105° C. (e.g., between 4° C. to 99° C., between 4° C. to 98° C., between 4° C. to 95° C., between 4° C. to 90° C., between 4° C. to 85° C., between 4° C. to 80° C., between 4° C. to 75° C., between 4° C. to 70° C., between 4° C. to 65° C., between 4° C. to 60° C., etc.).

Any of these apparatuses may include a magnetic field applicator configured to apply a magnetic field to at least one region of the microfluidic path device when the microfluidic path device is seated in the seating mount. The magnetic field applicator may comprise a control arm mounted to the reagent storage frame.

In general, the controller may be configured to detect an identifying code on the fluid vial held by the fluid sample holders; in some variations, the identifying code comprises a barcode, RFID, or other way to identify (particularly in a non-contact manner) the contents of components of the fluid sample holder. The controller may be configured to determine a level of a reagent held by the reagent storage frame.

Any of these apparatuses may include an optical sensor drive configured to move one or more of the plurality of optical sensors around the seating mount and reagent storage frame, and/or one or more electroluminescent panels or other backlighting devices configured to provide illumination to a region underlying a portion of the reagent storage frame.

The methods and apparatuses described generally include one or more fluid power circuits to move material (liquid material) between the fluid chambers (depots, fluid-contacting sides, reactors, etc.) and channels of the microfluidic path device or within the microfluidic path device. A fluid power circuit may be a hydraulic or pneumatic circuit that may include the microfluidic device, and in particular one or more pressure channels and pressure-receiving sides of the chambers in a microfluidic device. The fluid power circuits may also be referred to as microfluidic power circuits. A single microfluidic chip may include multiple fluid power circuits; the fluid power circuits may also include one or more pressure lines and the interface between the pressure lines of the microfluidic control apparatus and the one or more microfluidic chips within the microfluidic path device. One or more fluid power circuits may share components (valves, pressure lines, vacuum caps, etc.) with other, overlapping fluid power circuits. Furthermore, for the same of convenience, it should be understood that where the term “pneumatic” is used, a general fluid power circuit (e.g., hydraulic and/or pneumatic) may be used instead or additionally. The fluid material being driven by the fluid power line may be any appropriate fluid (e.g., gas or liquid, such as air, water, oil, etc.).

Also described herein are microfluidic path devices for processing therapeutic polynucleotides in a closed path (e.g., closed-path microfluidic path devices). As mentioned, these microfluidic path devices may be referred to herein as microfluidic chips, microfluidic path plate, process chip, biochip, process plate, etc. In general, the microfluidic path device may be microfluidic path plate devices, which may be substantially flat plate-like structures; these structures may be relatively thin (e.g., less than a few mm thick, e.g., between 0.5-20 mm thick, between 0.5-15 mm thick, between 0.5-10 mm thick, etc.). The microfluidic path devices described herein may generally be at least partially transparent, and in particular, may be transparent on the top of the microfluidic path device, so that one or more optical sensors (cameras, CCD, fiber optics, etc.) may be used to sense, detect, monitor, record, etc. action, including fluid movement and/or movement of the elastic layer, with the microfluidic path device as it is used by the microfluidic apparatuses described herein.

Any of these microfluidic path devices may be configured to operate, as described herein, as closed-path devices, in which the chambers (and particularly the fluid-contacting chambers and fluid channels are sealed to the fluid input/output lines (e.g., fluid line) by a sealing connection that prevents exposure to the environment (e.g., air). This may be particularly critical in the manufacture of therapeutic mRNAs which may be degraded by exposure to RNAses and other contaminants in the environment.

For example a microfluidic path device may include: an elastic layer sandwiched between a first surface and a second surface; a plurality of chambers formed between the first surface and the second surface, wherein a portion of the elastic layer divides each chamber into a fluid-contacting side in the second surface and a pressure-receiving side in the first surface; a plurality of fluid channels each extending from a fluid port, the elastic membrane and through the first surface, and into the second surface to fluidly connect with the fluid-contacting sides of the plurality of chambers; and a plurality of pressure channels each extending from a one or more pressure port, through the first surface and the elastic layer, into the second surface and back through the elastic layer into the first surface, wherein each pressure channel of the plurality of pressure channels fluidly connects with one or more pressure-receiving sides of the plurality of chambers, further wherein the volumes of the fluid-contacting sides of each chamber may be adjusted by applying pressure from the one or more of the pressure ports.

A microfluidic path device (e.g., for forming a therapeutic polynucleotide, such as a therapeutic mRNA) may include: an elastic layer sandwiched between a first plate region having a first surface and a second plate region having a second surface; a plurality of chambers each having a fixed volume and formed between the first surface and the second surface, wherein a portion of the elastic layer divides each chamber into a fluid-contacting side in the second surface and a pressure-receiving side in the first surface; a plurality of fluid channels each extending from a fluid port through the first plate region and into the second plate region to fluidly connect with the fluid-contacting side of one or more of the plurality of chambers; and a plurality of pressure channels each extending from one or more pressure ports, through the first plate region and elastic layer, into the second plate region, and back through the elastic layer and into the first plate region, wherein each pressure channel of the plurality of pressure channels extends within the first plate region and fluidly connects with one or more pressure-receiving sides of one or more of the plurality of chambers, wherein the plurality fluid-contacting sides of the plurality of chambers are interconnected, further wherein the fluid-contacting side of each chamber is concave so that the elastic layer seats flush and without gaps to the fluid-contacting side in the second surface when a positive pressure in the pressure-receiving side drives the elastic layer against the fluid-contacting side.

Any of these microfluidic devices may be configured to form a secure seal with one or more fluid and/or pressure lines. In some variations the ports (fluid ports, pressure ports, etc.) may be formed as channels into the body of the microfluidic device (e.g., cylindrical channels) down to an opening through the elastic layer of the device; the underside of this elastic layer may be supported by the second plate region (e.g., the second surface of the second plate region) with a passage into the second plate region that has a narrow diameter than the port channel diameter, so that an input line (fluid line and/or pressure line) may be supported against the elastic layer when driven against the elastic layer to form a seal.

For example, a microfluidic path device (e.g., for forming a therapeutic polynucleotide) may generally be configured to operate in a closed path. The microfluidic path device may include: an elastic layer sandwiched between a first plate region having a first surface and a second plate region having a second surface; a plurality of chambers each having a fixed volume and formed between the first surface and the second surface, wherein a portion of the elastic layer divides each chamber into a fluid-contacting side in the second surface and a pressure-receiving side in the first surface; a plurality of fluid channels each extending from a fluid port through the first plate region and into the second plate region to fluidly connect with the fluid-contacting side of one or more of the plurality of chambers; and a plurality of pressure channels each extending from one or more pressure ports, through the first plate region and elastic layer, into the second plate region, and back through the elastic layer and into the first plate region, wherein each pressure channel of the plurality of pressure channels extends within the first plate region and fluidly connects with one or more pressure-receiving sides of one or more of the plurality of chambers, wherein each fluid port comprises a port channel that extends extending transversely through the first plate region, and opens onto an opening through the elastic layer having an opening diameter that is smaller than a diameter of the port channel, further wherein a diameter of the fluid channel second plate region is smaller than the diameter of the port channel.

Any of these device may be configured to reduce or eliminate bubbles that may form within the fluidic pathways, e.g., by include one or more vacuum cap within the fluidic circuit(s) of the device. For example, a microfluidic path device (e.g., for processing therapeutic polynucleotides in a closed path) may include: an elastic layer sandwiched between a first plate region having a first surface and a second plate region having a second surface; a plurality of chambers each having a fixed volume and formed between the first surface and the second surface, wherein a portion of the elastic layer divides each chamber into a fluid-contacting side in the second surface and a pressure-receiving side in the first surface; a plurality of fluid channels each extending from a fluid port through the first plate region and into the second plate region to fluidly connect with the fluid-contacting side of one or more of the plurality of chambers; and a plurality of pressure channels each extending from one or more pressure ports, through the first plate region and elastic layer, into the second plate region, and back through the elastic layer and into the first plate region, wherein each pressure channel of the plurality of pressure channels extends within the first plate region and fluidly connects with one or more pressure-receiving sides of one or more of the plurality of chambers, at least one vacuum cap between at least some of the plurality chambers, wherein the at least one vacuum caps comprises a bubble-removing chamber formed between the first surface and the second surface, wherein the elastic layer divides the bubble-removing chamber into a fluid-contacting side of the bubble-removing chamber in the second surface and a vacuum receiving side in the first surface, further wherein the fluid-contacting side of the bubble-removing chamber is in fluid communication with at least two of the fluid-contacting sides of the plurality of chambers and wherein at least the portion of the elastic layer between the fluid-contacting side of the bubble-removing chamber and the vacuum receiving side is gas permeable.

Thus, any of these microfluidic path devices may include at least one vacuum cap between at least some of the plurality chambers, wherein the at least one vacuum caps comprises a bubble-removing chamber formed between the first surface and the second surface, wherein a gas-permeable elastic layer divides the bubble-removing chamber into a fluid-contacting side of the bubble-removing chamber in the second surface and a vacuum receiving side in the first surface, further wherein the fluid-contacting side of the bubble-removing chamber is in fluid communication with at least two of the fluid-contacting sides of the plurality of chambers.

Any of these microfluidic path devices may be configured to prevent dead space regions within even the smallest chambers of the microfluidics path device. For example, the fluid-contacting side in the second surface and the pressure-receiving side are concave and configured so that the elastic layer seats flush and without gaps to the fluid-contacting side in the second surface when a positive pressure in the pressure-receiving side drives the elastic layer against the fluid-contacting side.

In general, these device may be formed of one plate or multiple plates. For example, a single plate may include multiple surfaces, including internal surfaces. Alternatively, the device may include two or more plates that may be stacked onto each other and/or laminated together, including with an elastic layer and/or membrane between then. In some variations of the microfluidic path device the first surface and the second surface may be part of at least one plate or plate region. For example, the first surface may be part of a first plate and the second surface is part of a second plate. Alternatively the first surface may be part of a first plate region and the second surface may be part of a second plate region; in some variations the first plate region and second plate region may be part of the same plate; alternatively the first plate region and the second plate region may be part of different plates forming the microfluidic path device.

The one or more pressure ports and fluid ports may be disposed adjacent to a periphery of the microfluidic path device. The pressure ports and fluid ports may be arranged in groups and/or interspaced. In general, the pressure ports and fluid ports may be arranged around the periphery of the microfluidic path device along the top of the device, and/or may be arranged to that the central region of the microfluidic path device is open and exposed for visualization (by one or more optical sensors) that may monitor fluid movement and/or processing of the microfluidic path device.

In some variations, the chambers of the microfluidic path devices may be paired chambers, wherein a first chamber (e.g., the fluid-contacting portion) of each paired chamber of the plurality is fluidically connected to a second chamber (e.g., the fluid contacting portion) of each paired chamber. The pressure-receiving sides of each chamber may be separately controlled by coupling with separate (or separable and/or joinable) pressure lines, or fluid power circuits on the microfluidic path device. In some variations, a first chamber of a paired chamber may be connected to any of the other paired chamber via a valved fluidic connection. The valve may be part of a fluid power circuit and may be opened/closed by the controller applying fluid pressure (e.g., pneumatic, hydraulic, etc.) to deflect the elastic layer within the small chamber formed between the first and second surfaces.

As mentioned above, the microfluidic path device may be a sealed path device. The operation of the device may be monitored and controlled by the controller apparatus without contacting the liquids (e.g., containing the therapeutic polynucleotide, e.g., mRNA). In some variations the microfluidic path device may be at least substantially translucent to visible or ultraviolet light. For example, the microfluidic path device is substantially transparent to visible or ultraviolet light.

Any of these methods and apparatuses may be configured to purify the polynucleotide (e.g., the mRNA) on in the microfluidic path device. For example, the microfluidic path device may include a material inserted into the fluid-contacting side of the channel; e.g., the material may comprise a cellulose material configured to selectively absorb double-stranded mRNA.

Any of these microfluidic path devices may be configured to remove impurities from the therapeutic material (e.g., a "drug particle"), such as the therapeutic mRNA material (e.g., a therapeutic mRNA encapsulated in a delivery vehicle). For example, any of the microfluidic path devices described herein may include one or more chambers configured for buffer adjustment and/or drug particle concentration. In some cases, the apparatus is configured to tangentially flow a solution of drug particles through a chamber having one or more ultrafiltration membranes to separate nanoparticles from the solvents, thereby purifying and/or concentrating drug particles in a retentate. Smaller particles, such as solvents and ions, can be pass through the membrane as a permeate material, to waste, while drug particles (e.g., mRNA encapsulated in delivery vehicle) in the same solvent can be collected downstream as retentate. In some variations this may concentrate the drug particles. In some cases, a biocompatible and stable buffer can be used for downstream processing for injection to patients. Buffer adjustment may be accomplished by adding diluent with appropriate composition of water, salt, excipients, and/or other constituents. The concentration of certain chemicals may be increased by adding a buffer with higher chemical concentration and vice versa. For example, in some cases, ethanol concentration can be reduced by half by adding the same volume of water. The methods and apparatuses described herein can allow for the formulation of the biomolecule-containing product, buffer adjustment and concentration to be performed in one microfluidic path device. The formulation buffer may be adjusted to a more biocompatible and stable buffer for downstream processing and injection to patients. The drug concentration may be also adjusted to an acceptable volume for the drug administration method after formulation and buffer adjustment process. Thus, any of these apparatuses may include one or more chambers having a membrane, such as an ultrafiltration membrane. A microfluidic path device may therefore include a concentrator. In some variations, the microfluidic path includes a dialysis chamber (e.g., within the thickness of the second surface, e.g., second layer portion).

Any of these microfluidic path devices may include a delivery reservoir configured to deliver a pre-selected volume of a fluid to the at least one chamber; for example, a pre-selected volume of the chambers may be, e.g., between about 20 nanoliters and 5 mL (e.g., 25 nL and 5 mL, about 50 nL and 5 mL, between about 50 nL and 2 mL, greater than about 25 nL, about 30 nL, about 50 nL, about 75 nL, etc.).

The first layer portion and/or the second layer portion may be formed from a rigid material. Any of these microfluidic path device may include a third layer portion (e.g., a third surface) that may be formed from a rigid material, e.g., laminated to an elastic material. The rigid material may be a polymer, e.g., cycloolefin copolymer, or glass.

For example, a microfluidic path device may include: an elastic layer between (e.g., sandwiched between) a first plate and a second plate; a plurality of chambers each having a fixed volume, each chamber formed between the first plate and the second plate, wherein a portion of the elastic layer divides each chamber into a fluid-contacting side and a pressure-receiving side; a plurality of fluid ports through the first plate each comprising an exposed portion of the elastic layer that is supported by the second plate, wherein each fluid port comprises an opening through the elastic layer and into the second plate that fluidly connect with the fluid-contacting side of one of the plurality of chambers; a plurality of pressure ports through the first plate each comprising an exposed portion of the elastic layer that is supported by the second plate, wherein each fluid port comprises an opening through the elastic layer and into the second plate that fluidly connect with the pressure-receiving side of one of the plurality of chambers.

A microfluidic path device may include: an elastic layer sandwiched between a first plate and a second plate; a plurality of chambers each having a fixed volume, each chamber formed between the first plate and the second plate, wherein a portion of the elastic layer divides each chamber into a fluid-contacting side and a pressure-receiving side; a plurality of fluid ports each passing through the first plate and through the elastic layer and into the second plate to fluidly connect with the fluid-contacting side of one of the plurality of chambers; a plurality of pressure ports each passing through the first plate and through the elastic layer and into the second plate, then back through the elastic layer and into the first layer to fluidly connect with the pressure-receiving side of one of the plurality of chambers.

For example, a microfluidic path device may include: a first plate having a first surface and a second surface and a thickness therebetween; a second plate having a first surface and a second surface and a thickness therebetween; an elastic layer sandwiched between the second surface of the first plate and the first surface of the second plate; a third plate coupled to the second plate on the second surface of the second plate, the third plate having a first surface and a second surface; at least one chamber having a fixed volume, the at least one chamber formed in the second surface of the first plate and the first surface of the second plate, wherein a portion of the elastic layer divides the at least one chamber into a fluid-contacting side and a pressure-receiving side; a fluid channel extending from a fluid port passing through the thickness of the first plate, to a fluid channel opening through the elastic layer and through the thickness of the second plate to fluidly connect with a connecting channel formed in the second surface of the second plate, wherein the fluid channel connects to the fluid-contacting side of the at least one chamber; wherein the diameter of the fluid port through the thickness of the first plate is larger than the diameter of the fluid channel opening through the elastic layer; and an exit channel extending from the fluid-contacting side through the second surface of the second plate, wherein a port (e.g., valve) formed by the elastic layer is between the fluid-contacting side and the exit channel.

For example, a microfluidic path device for processing therapeutic polynucleotides in a closed path may include: a first plate having a first surface and a second surface and a thickness therebetween; a second plate having a first surface and a second surface and a thickness therebetween; an elastic layer sandwiched between the second surface of the first plate and the first surface of the second plate; a third plate coupled to the second plate on the second surface of the second plate; at least one chamber having a fixed volume, the at least one chamber formed in the second surface of the first plate and the first surface of the second plate, wherein a portion of the elastic layer divides the at least one chamber into a fluid-contacting side and a pressure-receiving side; a fluid channel extending from a fluid port passing through the thickness of the first plate, to a fluid channel opening through the elastic layer and through the thickness of the second plate to fluidly connect with a connecting channel formed in the second surface of the second plate and bounded by the third plate, wherein the fluid channel connects to the fluid-contacting side of the at least one chamber; a pressure channel extending from a pressure port passing through the thickness of the first plate, to a pressure channel opening through the elastic layer and into the thickness of the second plate to fluidly connect with a connecting pressure channel formed in the second surface of the first plate and bounded by the elastic layer, wherein the pressure channel connects to the pressure-receiving side of the at least one chamber; wherein the diameter of the fluid port passing through the thickness of the first plate is larger than the fluid channel opening through the elastic layer, further wherein the diameter of the pressure port passing through the thickness of the first plate is larger than the pressure channel opening through the elastic layer; and an exit channel extending from the fluid-contacting side through the second surface of the second plate, wherein a valve (e.g., port) formed by the elastic layer is between the fluid-contacting side and the exit channel.

A microfluidic path device may include a pressure channel extending from a pressure port passing through the thickness of the first plate, to a pressure channel opening through the elastic layer and into the thickness of the second plate to fluidly connect with a connecting pressure channel formed in the second surface of the first plate and bounded by the elastic layer, wherein the pressure channel connects to the pressure-receiving side of the at least one chamber.

The microfluidic path devices described herein may include a plurality of pressure ports and fluid ports are disposed adjacent to a periphery of the microfluidic path device.

For example, a microfluidic path device for processing therapeutic polynucleotides in a closed path may include: a first plate having a first surface and a second surface and a thickness therebetween, the first surface forming an exposed outer surface; a second plate having a first surface and a second surface and a thickness therebetween; an elastic layer sandwiched between the second surface of the first plate and the first surface of the second plate; a third plate coupled to the second plate on the second surface of the second plate, the third plate having a first surface and a second surface and a thickness therebetween, the second surface forming an exposed bottom surface on the bottom of the device; at least one pair of chambers, each having a fixed volume, the at least one pair of chambers formed in the second surface of the first plate and the first surface of the second plate, wherein a portion of the elastic layer bifurcates each of the at least one pair of chambers into a fluid-contacting side and a pressure-receiving side, wherein the each least one pair of chambers is fluidically connected therebetween; a fluid channel extending from a fluid port passing through the thickness of the first plate, to a fluid channel opening through the elastic layer and through the thickness of the second plate to fluidly connect with a connecting channel formed in the second surface of the second plate and bounded by the third plate, wherein the fluid channel connects to the fluid-contacting side of the at least one chamber; a pressure channel extending from a pressure port passing through the thickness of the first plate, to a pressure channel opening through the elastic layer and into the thickness of the second plate to fluidly connect with a connecting pressure channel formed in the second surface of the first plate and bounded by the elastic layer, wherein the pressure channel connects to the pressure-receiving side of the at least one chamber; and an exit channel extending from the fluid-contacting side through the second surface of the second plate, wherein a valve (e.g., port) formed by the elastic layer is between the fluid-contacting side and the exit channel.

Also described herein are apparatuses (e.g., systems) that include both any of the microfluidic apparatuses (e.g., microfluidic path device control systems) and one or more microfluidic path devices. For example, a system may include: a microfluidic apparatus, wherein the apparatus comprises: a seating mount for a microfluidic path device; a fluid interface assembly comprising a plurality of fluidic lines and pressure lines, wherein each fluidic line and each pressure line is configured to be driven against the microfluidic path device seated in the seating mount; a reagent storage frame comprising a plurality of fluid sample holders each configured to hold a fluid vial and each configured to couple to the fluid interface assembly through one of the fluidic lines of the fluid interface assembly. As described in greater detail below, in some variations, the fluid sample holders may be adapted to be driven directly against the microfluidic path device, even without a separate fluidic line; the sample holder may form the fluidic line. The fluidic line, or separately the sample holder (e.g., vial, container, etc.) may be configured to be held by pressure against an elastomeric seat that is formed in the microfluidic path device, e.g., at the port.

The apparatus may also include a plurality of optical sensors arranged around the seating mount and reagent storage frame to monitor fluid levels within the reagent storage frame and fluidic movement in the microfluidic path device when the microfluidic path device is seated in the seating mount; and a controller configured to control the application of pressure through the pressure lines to drive fluidic movement in the microfluidic path device when the microfluidic path device is seated in the seating mount; and the microfluidic path device, the microfluidic path device comprising: a first plate having a first surface and a second surface and a thickness therebetween, the first surface forming an exposed outer surface; a second plate having a first surface and a second surface and a thickness therebetween; an elastic layer sandwiched between the second surface of the first plate and the first surface of the second plate; a third plate coupled to the second plate on the second surface of the second plate, the third plate having a first surface and a second surface and a thickness therebetween, the second surface forming an exposed bottom surface on the bottom of the device; at least one chamber having a fixed volume, the at least one chamber formed in the second surface of the first plate and the first surface of the second plate, wherein a portion of the elastic layer bifurcates the at least one chamber into a fluid-contacting side and a pressure-receiving side; a fluid channel extending from a fluid port passing through the thickness of the first plate, to a fluid channel opening through the elastic layer and through the thickness of the second plate to fluidly connect with a connecting channel formed in the second surface of the second plate and bounded by the third plate, wherein the fluid channel connects to the fluid-contacting side of the at least one chamber; a pressure channel extending from a pressure port passing through the thickness of the first plate, to a pressure channel opening through the elastic layer and into the thickness of the second plate to fluidly connect with a connecting pressure channel formed in the second surface of the first plate and bounded by the elastic layer, wherein the pressure channel connects to the pressure-receiving side of the at least one chamber; wherein the diameter of the fluid port passing through the thickness of the first plate is larger than the fluid channel opening through the elastic layer, further wherein the diameter of the pressure port passing through the thickness of the first plate is larger than the pressure channel opening through the elastic layer; and an exit channel extending from the fluid-contacting side through the second surface of the second plate, wherein a valve formed by the elastic layer is between the fluid-contacting side and the exit channel.

Also described herein are methods of using any of these apparatus and devices. For example, a method of processing a fluid in a microfluidic path device to form a therapeutic polynucleotide (e.g., therapeutic mRNA) may include: sealingly and independently coupling a distal end of each of a plurality of fluid lines and a plurality of pressure lines to plurality of fluid ports or pressure ports on a surface of a microfluidic path device, wherein each distal end is biased to be driven against an elastic layer between a first surface and a second surface, wherein the microfluidic path device comprises a plurality of chambers each divided into a fluid-contacting side formed in the second surface and a pressure-receiving side formed in the first surface; and driving fluid through the fluid-contacting sides of the plurality of chambers by the application of positive and negative pressure within the pressure-receiving sides of the chambers to change the sizes of the plurality of fluid-contacting sides.

A method of processing a fluid in a microfluidic path device may include: sealingly and independently coupling a distal end of each of a plurality of fluid lines and a plurality of pressure lines to plurality of fluid ports or pressure ports on a surface of a microfluidic path device, wherein each distal end is biased to be driven against an elastic layer between a first plate and a second plate, wherein the microfluidic path device comprises a plurality of chambers each divided into a fluid-contacting side formed in the second plate and a pressure-receiving side formed in the first plate, wherein the fluid-contacting sides are interconnected; and driving fluid through the interconnected fluid-contacting sides and operating a valve to meter the movement of fluid between the fluid-contacting sides of the plurality of chambers by the application of positive and negative pressure within the pressure-receiving sides of the chambers to change the sizes of the plurality of fluid-contacting sides.

Driving fluid through the fluid-contacting sides may include deflecting an elastic layer sandwiched between the first surface and the second surface.

As mentioned above, any of these methods may include optical feedback from the microfluidic path device to control the application of positive and negative pressure.

These method may include controlling valves by deflecting an elastic layer between the first surface and the second surface. For example, the controller may control fluid power (e.g., pneumatic, hydraulic) via a fluid power circuit (e.g., fluid line, valve(s), etc.) to control processing of the microfluidic path device.

In general, driving may comprise driving fluid through interconnected fluid-contacting sides and operating a valve to meter the movement of fluid between the fluid-contacting sides of the plurality of chambers by the application of positive and negative pressure. The fluid-contacting sides may be interconnected.

For example described herein are methods of processing a fluid in a microfluidic path device, the method comprising: sealingly and independently coupling a distal end of each of a plurality of fluid lines and a plurality of pressure lines to plurality of fluid ports or pressure ports on a surface of a microfluidic path device, wherein each distal end is biased (e.g., spring-loaded) to drive the distal ends against an elastic layer between a first plate and a second plate, wherein the microfluidic path device comprises a plurality of chambers each chamber divided into a fluid-contacting side formed in the second plate and a pressure-receiving side formed in the first plate; and pneumatically driving fluid through a plurality of fluid-contacting sides of a plurality of chambers by coordinating the application of positive and negative pressure within the pressure-receiving sides of the chambers to change the sizes of the plurality of fluid-contacting sides.

In some variations, a method of processing a fluid in a microfluidic path device may include: sealingly (and independently) coupling a distal end of each of a plurality of fluid lines and a plurality of pressure lines to plurality of fluid ports or pressure ports on a surface of a microfluidic path device, wherein each distal end is biased to drive the distal ends against an elastic layer between a first plate and a second plate of the microfluidic path device, wherein the microfluidic path device comprises a plurality of chambers each chamber divided into a fluid-contacting side formed in the second plate and a pressure-receiving side formed in the first plate; and driving fluid through a plurality of fluid-contacting sides of a plurality of chambers.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 7E shows an enlarged view of the port interface region.

DETAILED DESCRIPTION

Figure 1:
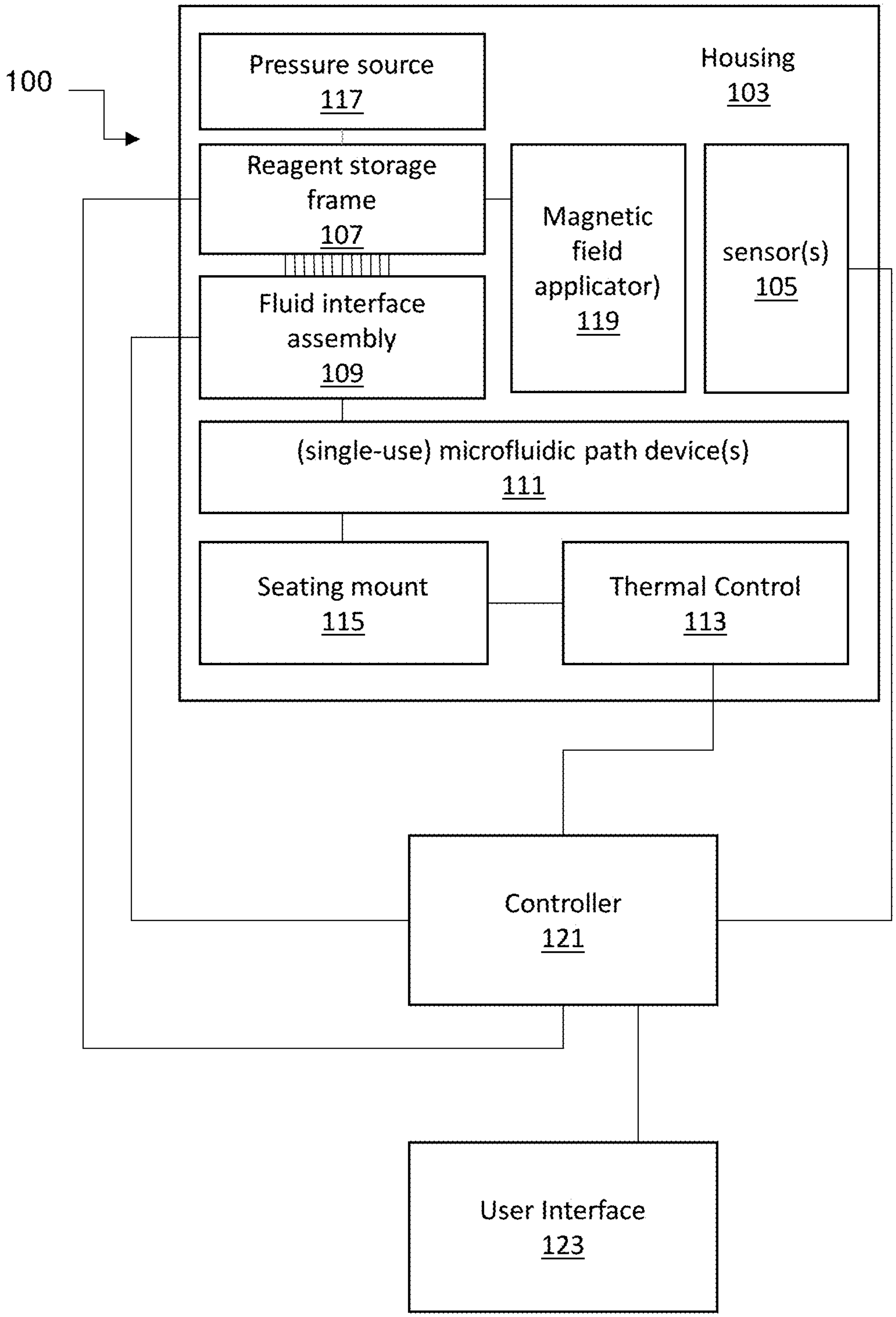
FIG. 1 is a schematic of one variation of a system including a microfluidic apparatus and a microfluidic path device as described herein.

In general, described herein are apparatuses (e.g., systems, devices, etc.) and methods for processing therapeutic polynucleotides. In particular, these apparatuses and methods may be closed path apparatuses and methods that are configured to minimize or eliminate manual handling during operation. The closed path apparatus and methods may provide a nearly entirely aseptic environment, and the components may provide a sterile path for processing from initial input (e.g., template) to output (compounded therapeutic). Material inputs (nucleotides, and any chemical components) into the apparatus may be sterile, and may be input into the system without requiring virtually any manual interaction.

The methods and apparatuses described herein may generate therapeutics at very rapid cycle times at very high degree of reproducibility. The apparatuses described herein are configured to provide, in a single integrated apparatus, synthesis, purification, dialysis, compounding and concentration of one or more therapeutic composition (including, but not limited to therapeutic polynucleotides). All or some of these processing steps may be performed in an unbroken fluid processing pathway, which may be configured as one or a series of consumable microfluidic path device(s) (which may also be referred to as a microfluidic path chip, microfluidic path plate, process chip, biochip, or process plate). This may allow for patient-specific therapeutics to be synthesized, including compounding, at a point of care (e.g. hospital, clinic, pharmacy, etc.).

During operation of the apparatus the fluid path may remain substantially unbroken, and contamination may be substantially eliminated by non-contact monitoring (e.g., optically monitoring), including fluid flow measurement, mixing monitoring, etc. and by manipulating precise microfluidic amounts (metering, mixing, etc.) using pressure applied from a deflectable membrane on an opposite side of the fluidic chambers and channels.

These apparatuses and methods may be configured for use at a point of care. For example, the methods and apparatuses described herein may be configured for manufacturing customized therapeutic compositions including one or more therapeutic polynucleotide (e.g., mRNA, microRNA, DNA, etc.).

Thus, the methods and apparatuses described herein may provide scalable polynucleotide manufacturing, production of single patient dosages, elimination of touchpoints to limit contamination, input and process tracking for meeting clinical manufacturing requirements, and use in point-of-care operations for therapeutics. The microfluidic instrumentation and processes described herein can provide major advantages.

Apparatus

In general, the apparatuses described herein may be microfluidic apparatuses (e.g., microfluidic control apparatuses). In some variations, these microfluidic apparatuses may include closed path microfluidic apparatus for processing therapeutic polynucleotides at a point of care. These apparatuses may be configured to operate on one or more microfluidic path device. The microfluidic apparatus may include one or more microfluidic path device (e.g. process chip, formulation chip, etc.) or it may be configured for use with the microfluidic path device, and thus, the microfluidic apparatus may not include the microfluidic path device. In some variation the microfluidic apparatus (either with or without a microfluidic path device) may be referred to as a system.

In general, a microfluidic apparatus as described herein may include a seating mount for a microfluidic device, a fluid interface assembly comprising a plurality of fluidic lines and pressure lines, a reagent storage frame comprising a plurality of fluid sample holders each configured to hold a fluid vial and each configured to couple to the fluid interface assembly through one of the fluidic lines of the fluid interface assembly, a plurality of optical sensors arranged around the seating mount and reagent storage frame to monitor fluid levels within the reagent storage frame and fluidic movement in the microfluidic path device, and a controller configured to control the application of pressure through the pressure lines to drive fluidic movement in the microfluidic path device. In any of these apparatuses, each fluidic line and each pressure line may be configured to be driven against the microfluidic path device seated in the seating mount.

The controller may coordinate processing, including moving one or more fluid(s) onto and on the microfluidic path device, mixing one or more fluids on the microfluidic path device, adding one or more components to the microfluidic path device, metering fluid in the microfluidic path device, regulating the temperature of the microfluidic path device, applying a magnetic field (e.g., when using magnetic beads), etc. The controller may include software, firmware and/or hardware. In some variations the controller may receive input from the user and may provide outputs (e.g., via a monitor, touchscreen, etc.). The controller may communicate with a remote server, e.g., to track operation of the apparatus, to re-order materials (e.g., components such as nucleotides, microfluidic path devices, etc.), and/or to download protocols, etc.

FIG. 1 shows a diagrammatic representation of one example of a system for processing polynucleotides, including an apparatus having a housing 103 enclosing a seating mount 115 which can hold one or more microfluidic path devices 111, which may be single use devices. The housing may be a chamber, enclosure, or the like, which may include a lid or opening; when closed it may be sealed. The housing may enclose a thermal regulator and/or may be configured to be enclosed in a thermally-regulated environment (such as a refrigeration unit, etc.). The housing may form an aseptic barrier. In some variations the housing may form a humidified or humidity-controlled environment.

The seating mount 115 may be configured to secure the microfluidic path device using one or more pins or other components configured to hold the microfluidic path device in a fixed and predefined orientation.

In some variations, a thermal control 113 may be located adjacent to the seating mount 115, to modulate temperature to the one or more microfluidic path devices 111. The thermal control may include a thermoelectric component (e.g. Peltier device) and/or one or more heat sinks for controlling the temperature of all or a portion of the microfluidic path device. In some variations, more than one thermal control may be included, for separately regulating the temperature of different ones of one or more regions of the microfluidic path device. The thermal control may include one or more thermal sensors (e.g., thermocouples, etc.) that may be used for feedback control of the microfluidic path device and/or thermal control.

In FIG. 1, a fluidic interface assembly 109 couples the liquid reagents and/or pressure (e.g., gas) with a microfluidic path device 111 held in the seating mount 115, and may assist in delivery of fluidic materials as well as positive/negative gaseous pressure, from the pressure source 117, to the interior of the microfluidic path device 111. The fluid interface assembly may optionally assists in securing the microfluidic path device(s), as described in greater detail below. The fluid interface assembly may be removable coupled to the apparatus (and may be removed or a portion may be removed) for sterilization between uses.

A reagent storage frame 107 is configured to contain a plurality of fluid sample holders, each of which may hold a fluid vial configured to hold a reagent (e.g., nucleotides, solvent, water, etc.) for delivery to the microfluidic device 111 or, alternatively, a fluid vial may be configured to receive a product from the interior of the microfluidic path device 111. The reagent storage frame may be referred to as a reagent rack. In some variations, the reagent rack includes a plurality of pressure lines and/or a manifold configured to divide one or more pressure sources 117 into a plurality of pressure lines that may be applied to the microfluidic path device an may be independently or collectively (in sub-combinations) controlled.

The fluid interface assembly may include a plurality of fluid lines and/or pressure lines and may include a biased (e.g., spring-loaded) holder or tip that individually and independently drives each fluid and/or pressure line to the microfluidic path device when it is held in the seating mount 115. The tubing (e.g., the fluid lines and/or the pressure lines) may be part of the fluid interface assembly and or may connect to the fluid interface assembly. In some variation the fluid lines comprise a flexible tubing that connects between the reagent storage frame, via a connector that couples the vial to the tubing in a locking engagement (e.g., ferrule) and the microfluidic path device. The ends of the fluid paths, in some variations the ends of the fluid lines/pressure lines, may be configured to seal against the microfluidic path device, e.g., at a sealing port formed in the microfluidic path device, as described herein. For example, the ends of the fluid lines may cut or formed to be flat (perpendicular in side view). The vials may be pressurized (e.g., >1 atm pressure, such as 2 atm, 3 atm, 5 atm, etc.) to via the connector which may also connect to the pressure source. For example, the fluid vials may be pressurized to between 1-20 psig (e.g., 5 psig/20 psia, 10 psig, etc.). Negative or positive pressure may be applied; for example, a vacuum (e.g., −7 psig or 7 psia) may be applied to draw fluids back into the vials (e.g., the depots) at the end of the process. In general the fluid vials may be driven at lower pressure than the pneumatic valves, which may prevent or reduce leakage. In some variations the difference in pressure between the fluid and pneumatic valves may be between about 1 psi and about 25 psi (e.g., about 3 psi, about 5 psi, 7 psi, 10 psi, 12 psi, 15 psi, 20 psi, etc.).

As described in greater detail below, the fluid lines (or in some variations the fluid vials directly) and pressure lines may be driven against the ports (pressure port or fluid port) formed in the microfluidic path device to form a seal. Each pressure line and/or fluid line (or fluid vial) may be individually driven against the valve seat in the microfluidic path with a bias force that may form a seal at the port. The bias force (which may be pressure due to a spring or other force-applying element) may be configured to be greater than the pressure within the fluid vial (and/or fluid line) and within the pressure line to maintain the seal without leaking. For example, the difference in pressure between the fluid vial and the bias force may be greater than about 5 psi (e.g., greater than about 2 psi, greater than about 3 psi, greater than about 5 psi, greater than about 7 psi, greater than about 10 psi, etc.), and may be referred to as the valve closing pressure. In general, this bias force (valve closing pressure) may exceed the fluid driving pressure, e.g., by an amount that may be design dependent (e.g., 3 psi, 5 psi, 7 psi, 10 psi, etc.). The bias force may be constant or may be adjustable. The bias force may be applied to maintain the seal with the port on the microfluidic path assembly. In some variations the bias force may be adjusted based on the pressure within the fluid line (e.g., fluid vial) or the pressure line. The bias force for each fluid line (or fluid vial) and pressure line may be individually adjustable.

Each vial may be coded (e.g., by an identifier that may be read by one or more sensors, as described below). The controller may monitor the fluid level and therefore the amount of each material in the fluid interface assembly.

The apparatus may also include a magnetic field applicator 119, which may be configured to create a magnetic field at a region of the microfluidic path device 111. One or more sensors 105, which may be optical sensors, may be part of the apparatus, and may sense one or more of a barcode, a fluid level within a fluid vial held within the reagent storage frame, and fluidic movement within the microfluidic path device 111 when the device is mounted within the mounting seat 115.

The sensors may make measurements of the process on the device, e.g., by measuring an optical indicator. In some variations visual/optical markers may be used to estimate yield. For example, fluorescence may be used to detect process yield or residual material by tagging with fluorophores. Alternatively or in addition, dynamic light scattering may be used to measure particle size distributions within a portion of the microfluidic path device (e.g., such as a mixing portion). In some variations, the sensor measurements may be done using one or two optical fibers to convey light (e.g., laser light) in and detect an optical signal coming out. An instrument package may be mounted remotely from the device. Such non-contact sensing may be preferred.

In any of the methods and apparatuses described herein, the sensors (e.g., video sensors) may records all activity on the microfluidic path device (e.g., chip or cartridge). For example, an entire run for synthesizing and/or processing a material (such as a therapeutic RNA) may be recorded by one or more video sensors, including a video sensor that may visualize the microfluidic path device, e.g., from above. Processing on the microfluidics path device may be visually tracked and this record may be retained for later quality control and/or processing. Thus, the video record of the processing may be saved, stored and/or transmitted for subsequent review and/or analysis.

The internal portion of the apparatus, e.g., within the housing 103, may be further configured to be sterilizable. In particular, portions of the apparatus may be removed and individually sterilized. Sterilization may be performed, e.g., by UV irradiation, or any other method of sterilization that may be required to limit contamination or to meet regulatory requirements. The apparatus including the housing may be housed within a High Efficiency Particulate Air (HEPA) filtered environment. The apparatus including the housing may be housed within a temperature controlled enclosure.

As mentioned above, the apparatus may be controlled by controller 121, including to apply pressure through the microfluidic path device 111 to at least drive fluidic movement, amongst other tasks. The controller may be completely or partially outside of the housing. The controller may be configured to include user inputs/outputs. For example, the user interface 123 of the system may permit easy operation and direction of the apparatus and microfluidic path device(s).

Any of the apparatuses described herein may include all or some of the components shown in FIG. 1; not all components may be necessary. In FIG. 1, only some of the connections between components are shown; additional (or alternative) connections may be used.

Figure 2A:
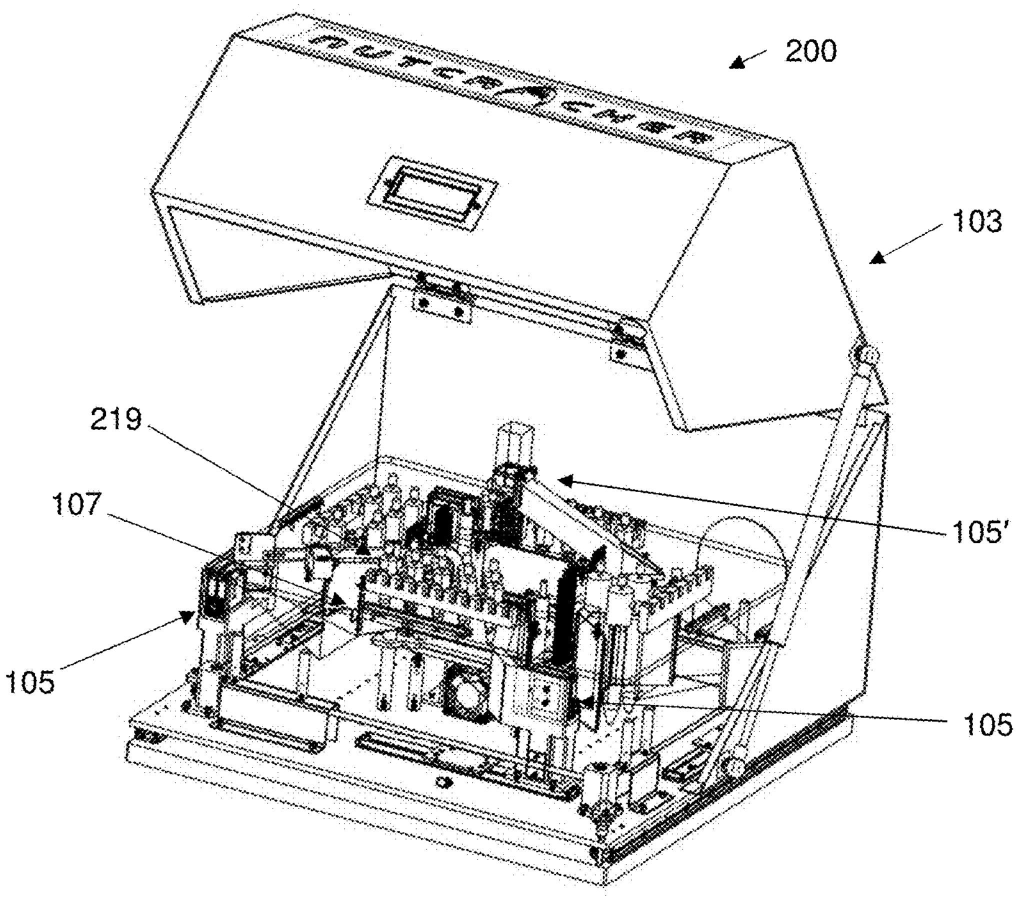
FIGS. 2A-2B show one example of a front and the back of a closed path microfluidic apparatus for processing therapeutic polynucleotides at a point of care.

FIG. 2A shows the front side of an apparatus 200, which may have any of the features of the apparatus of system 100. In FIG. 2A, housing 103 (e.g., cover) is shown in an open position displaying the reagent storage frame 107, sensors 105 (configured as cameras or optical sensors in this example), which may monitor fill levels and detect barcodes in a region below the horizontal plane of reagent storage frame 107, and control arm 219 for magnetic field applicator 119. Another sensor (camera) 105' is configured to be positioned over the upper surface of the microfluidic path device (not visible in FIG. 2A). In FIG. 2A, the control arm for the magnet and the upper sensor, which may each separately include one or more actuator that may be connected and controlled by the controller, not shown, may be mounted to the reagent storage frame. The apparatus also includes a gantry on which the side sensors (cameras) may move to visualize the reagent containers and/or other components of the apparatus. The upper sensor may be configured to view the microfluidic path device when mounted in the apparatus and this information may be used in operating the apparatus, e.g., by the controller.

Figure 2B:
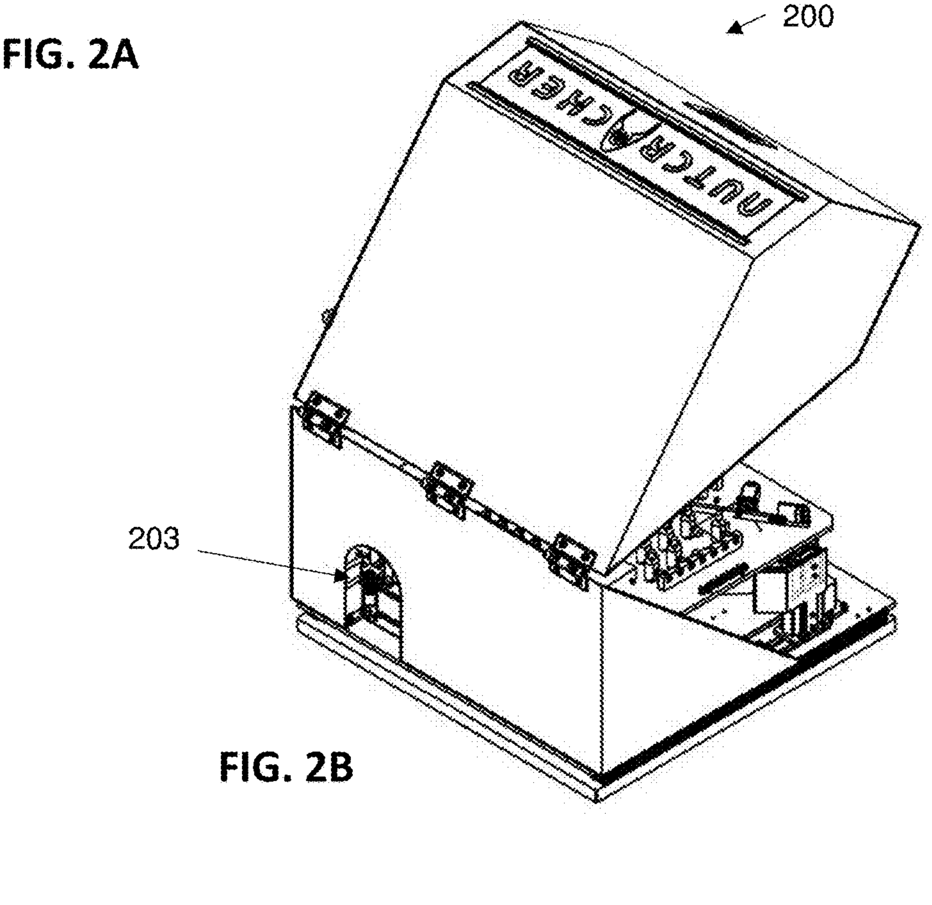
Figure 2C:
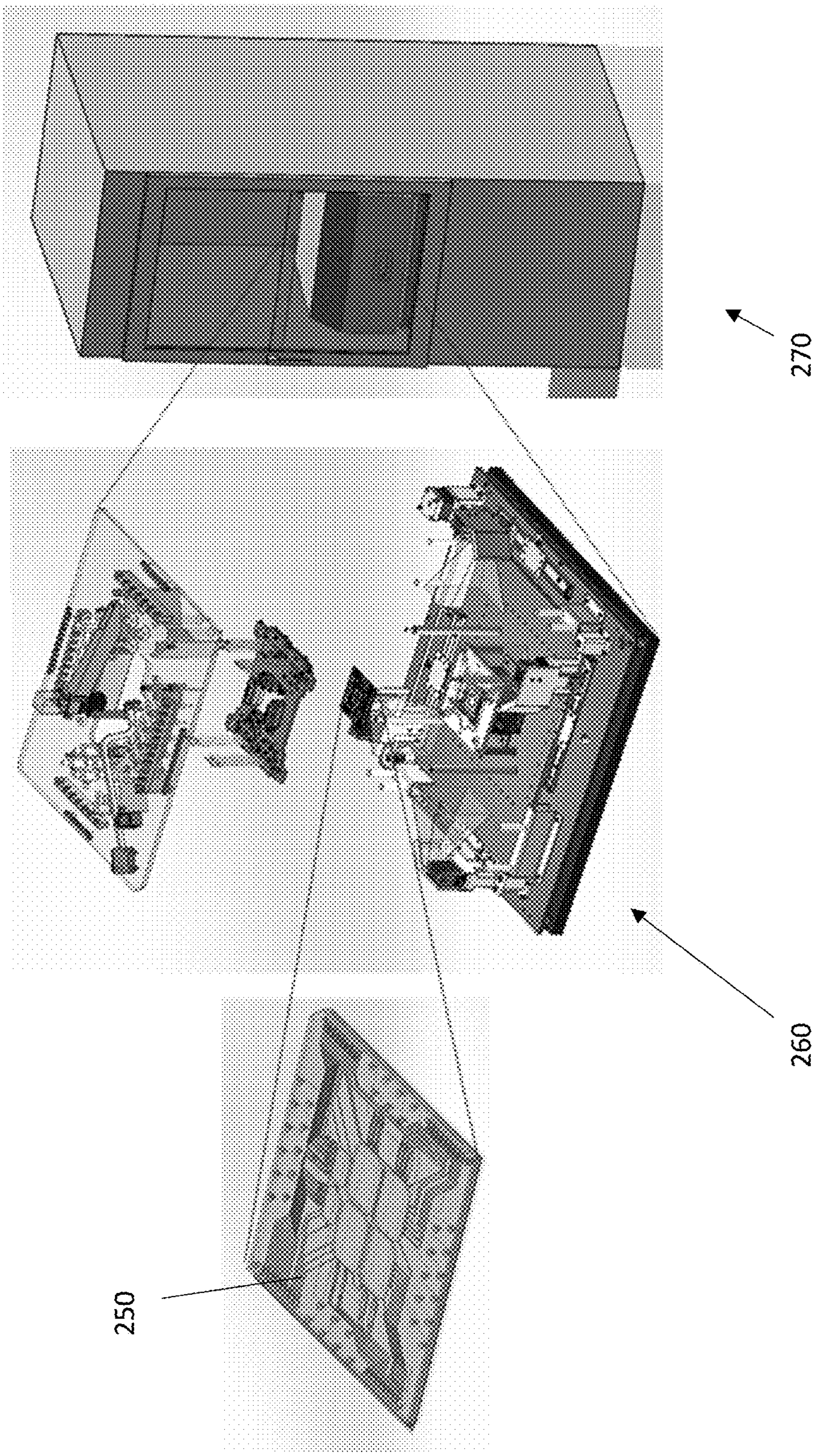
FIG. 2C is an example of an apparatus as described herein.

FIG. 2B shows the rear side of apparatus 200, where electrical power and pressure may be connected through access region 203. FIG. 2C illustrates another example of a system including a microfluidic path device.

The housing 103 may be made of any suitable material such as polymers, metals, or composites. The housing may be resistant to moisture and protects the sterility of the enclosed components during operation of the apparatus. The housing may be designed to be contained within a refrigerator to preserve reagents at low temperature when the reagents are stored on the reagent storage frame for the course of a batch or continuous run of the apparatus 200.

Figure 3:
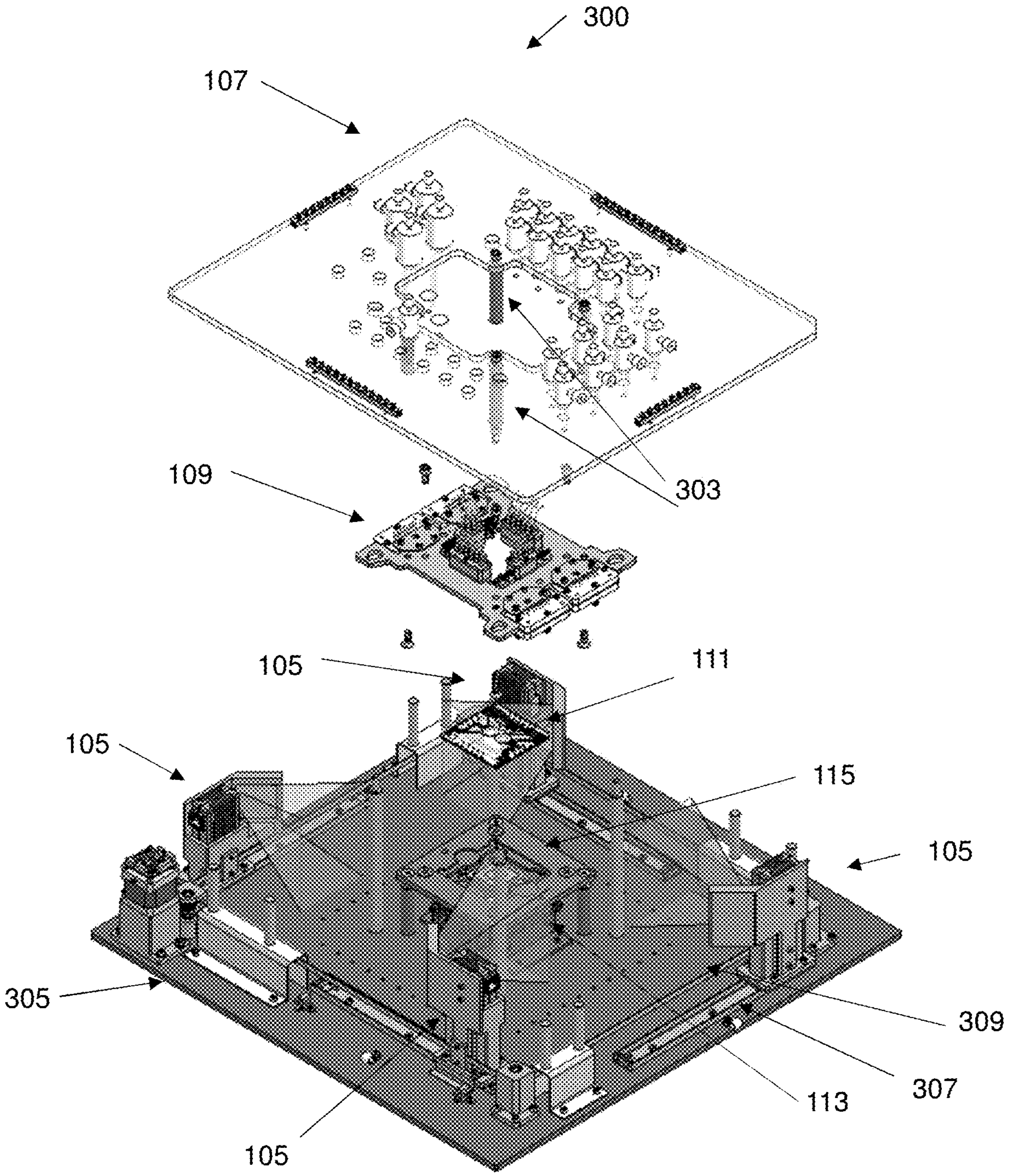
FIG. 3 is a partial exploded view of one example of a closed path microfluidic apparatus for processing therapeutic polynucleotides at a point of care, as described herein, including a reagent storage frame, fluid interface assembly, thermal control and sensor assembly, and a microfluidic path device.

In FIG. 3, an exploded view is provided of a portion of an apparatus, including a seating mount 115, microfluidic path device 111, fluid interface assembly 109, and reagent storage frame 107, showing how these portions fit together and align to provide functionality to the microfluidic path device 111 in apparatus 300, which may be like the apparatuses of FIG. 1 or 2, and have any of the features thereof. In FIG. 3, the reagent storage frame 107 is shown with some reagent vials and connectors (similar to FIG. 2A). Rods 303 are shown that connect the reagent frame 107 to the fluidic interface assembly 109 and can attach (e.g., by screws) to frame 107 and assembly 109 at receiving holes adjacent to the seating mount 115. The seating mount 115 may itself include a frame into which the microfluidic path device 111 may be placed, and aligning pins (not visible in FIG. 3) may securely orient each of these vertically arranged components to the microfluidic path device 111.

Two or more sets of pins may be used for alignment. For example, the seating mount 115 (also referred to as a lower nest) may have two or more short (e.g., 1.5 mm) pins that the microfluidics path device 111 may be aligned to when placed in the lower nest and may protrude upwards above the device. There may also be two long (e.g., 6 mm) pins that are pressed into the upper nest (e.g., fluidic interface assembly) and that protrude downward that mate to holes (visible) in the lower nest. These may act to guide the upper nest into position so the smaller (e.g., 1.5 mm) pins can then find the pin and slot features, also in the fluidic interface assembly 109 that produce the final alignment.

The seating mount 115 may be secured to a base 305 and may permit or limit (e.g., restrict) adjustment of the horizontal arrangement of the microfluidic path device 111. In some variations, the microfluidic path device 111 may be supported in a substantially horizontal plane, which may be useful to minimize pressures needed to drive fluidic movement throughout the microfluidic path device 111. In some other variations, the microfluidic path device may be supported in an orientation that is within about 1, 2, 3, 4, 5, 7, 9, 10, 11, 13, or about 15 degrees of a horizontal plane. Small deviations from a horizontal orientation may assist in removing bubbles from the fluids within the chamber(s) and lines running through the microfluidic path device 111. In yet other variations, the microfluidic path device may be supported in a substantially vertical orientation with respect to a base 305, or may be supported in an orientation that is within about 1, 2, 3, 4, 5, 7, 9, 10, 11, 13, or about 15 degrees of a vertical plane.

The seating mount 115, fluid interface assembly 109, and/or fluid sample holders may be formed from any suitable materials, such as for example, polymers, glass, metal or composites. The seating mount 115, fluid interface assembly 109, and/or fluid sample holders may be configured to be sterilized, such as by autoclaving or gamma radiation exposure. The apparatus 300 may further include one or more of: a seating mount release control configured to release the fluid interface assembly from the apparatus, a fluid assembly release control configured to release the fluid interface assembly from the apparatus, and/or a fluid sample holder release control configured to release the fluid sample holder from the apparatus. These release controls may be engaged so that each of the reagent storage frame, fluid interface assembly, and/or a fluid sample holder can be released from the apparatus so that they can be separately sterilized. These components may be released and/or reinserted separately and/or collectively.

A thermal control 113 may be disposed under the seating mount 115, adjacent to the microfluidic path device 111. The thermal control 113 may be configured to control the temperature in at least one region of the microfluidic path device 111 to between about 4° C. to about 105° C., or any selected temperature (or range of temperatures) therebetween. The thermal control may be any suitable temperature control such as, in one non-limiting example, a Peltier device, and/or a plurality of Peltier devices. In general the thermal control may be configured to allow for controlling the temperature independently at different thermal regions simultaneously.

Optical sensors 105 may be disposed upon the base 305 and may be oriented to sense fluid fill levels within fluidic vials disposed within the reagent storage frame reducing probability of disrupted process runs within the microfluidic path device 111. The optical sensors 105 may also sense a barcode on a fluidic vial to positively identify the identity and/or lot number of a reagent or product vial. The optical sensors may send the information about a fill level or a barcode to the controller 121, where the information may be stored or acted upon. This can assist in providing chain-of-custody data crucial to regulatory controls of personalized therapeutics.

The optical sensors 105 may be moveably disposed within a rail 307 (e.g., as part of a gantry) on the base 305 and may further be operably connected to an optical sensor drive. The optical sensor drive may be configured to move one or more of a plurality of optical sensors 105 around seating mount 115 and/or reagent storage frame 107. The plurality of optical sensors 105 may be moved in unison by coordinating movement with optical drive belt (e.g., drive chain) 309.

Figure 4A:
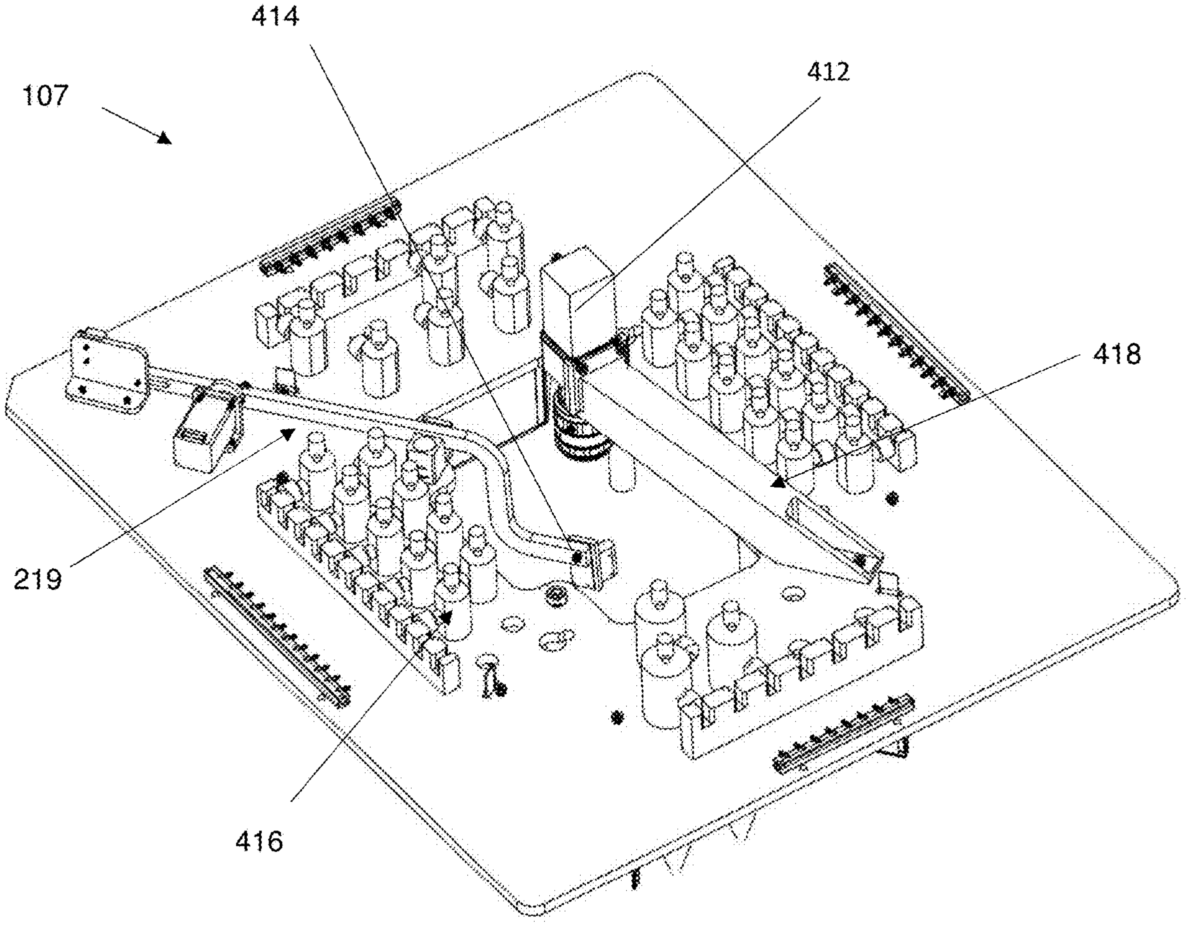
FIG. 4A is an isometric view of one example of a reagent storage frame.

FIG. 4A shows the upper surface of reagent storage frame 107, which may be used in any of the apparatuses described herein. Reagent storage frame 107 may support a magnetic field applicator 119 which may further include a control arm 219 which can control positioning of magnet 414 to be adjacent at least one region of microfluidic path device 111 when in use. One or more fluid sample holders 416 are disposed on the reagent storage frame 107. In some variations, a reagent storage frame 107 may include a plurality of fluid sample holders 416, each of which may have a same size or may have one or more different sizes. A fluid sample holder 416 includes a cap that may be pressurized (e.g., to about 1 PSI, 2 PSI, 3 PSI, 4 PSI, 5 PSI or more) above ambient atmospheric pressure, so that fluid from within a fluid vial contained by the fluid sample holder may be driven into the microfluidic path device 111. Alternatively, the fluid sample holder may not be pressurized at all, but may operate at ambient atmospheric pressure. In yet another variation, the fluid sample holder cap may permit reduced pressure to be applied to draw fluid or accept fluid being driven from the microfluidic path device 111. A plurality of fluid sample holders may distribute applied pressure to a plurality of fluid vials. The applied pressure may be distributed down to the fluid interface assembly. The fluid sample holder cap may include, for one non-limiting example, a Luer connection or the like, which can provide leak free connections under pressure. Fluid sample holder 416 may be connected via fluidic lines to the fluid interface assembly 109 for delivery into the microfluidic path device 111. The fluidic lines connecting the fluid sample holder (and fluid vial held therein) and the fluid interface assembly may be configured to have a length that is the shortest length possible to prevent wastage and lag.

The connections between the fluid sample holders, fluidic lines, and microfluidic path device can form a sealed and closed path that is isolated when the microfluidic path device is seated in the seating mount. The closed path provides useful protection from contamination when processing therapeutic polynucleotides.

The reagent storage frame may also provide a support to which a sensor/camera support arm 418 is connected. The support arm 418 supports an overhead sensor/camera 412 which is configured to image and detect signals from the microfluidic path device 111. The sensor/camera 412 may be a camera configured to record fluidic motion within the microfluidic path device 111 and/or detect a signal emitted from within one or more chamber of the microfluidic path device.

The signal detected by the sensor operating as a signal detector may be a visible, a fluorescent, a UV absorbance, or an IR absorbance signal. The signal detector is a non-contact signal detector, e.g., it does not touch the material emitting the signal directly. In some variations, the signal detector is configured to measure a nanoparticle size distribution. The signal detector may be configured to measure dynamic light scattering (DLS).

Figure 4B:
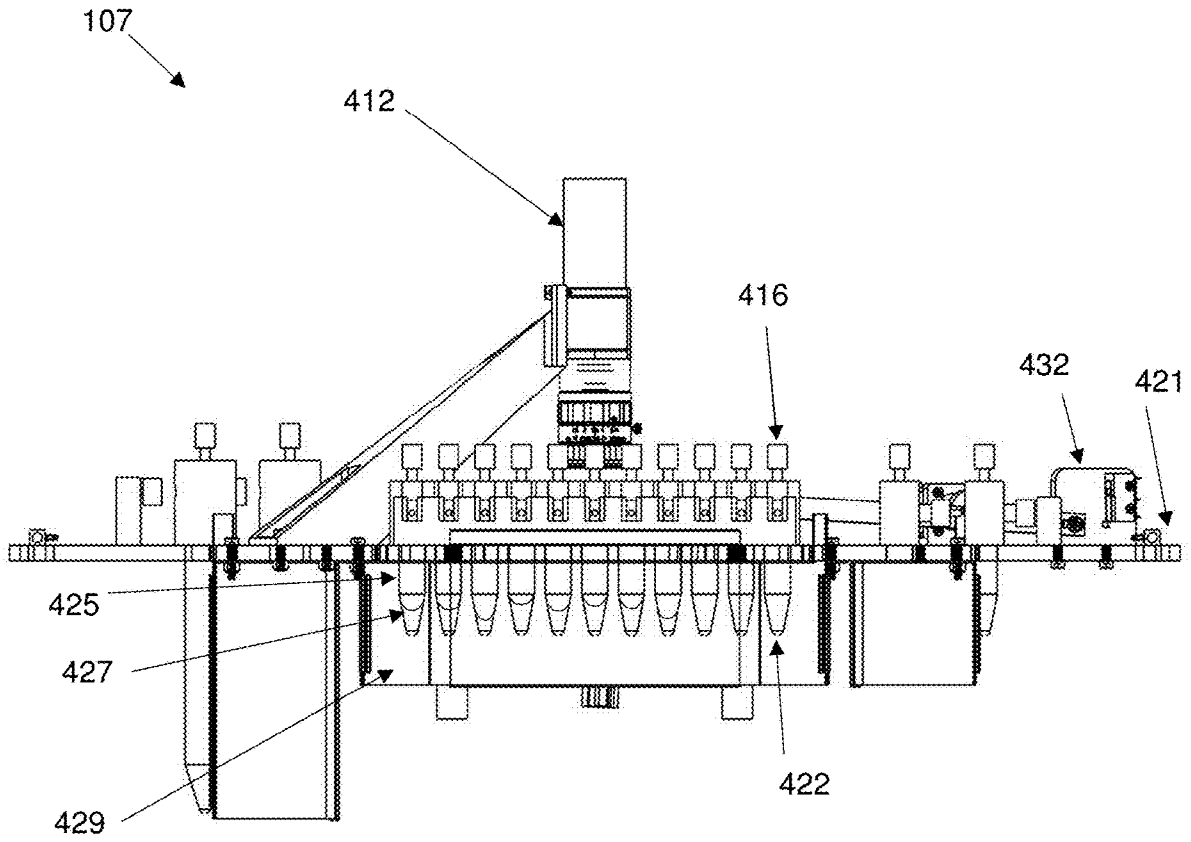
FIG. 4B is a side view of the reagent storage frame of FIG. 4A.

FIG. 4B shows a side view of the reagent storage frame 107, having a horizontal surface 421 in which the fluid vials 422 contained by fluid sample holders 416 may be disposed. The reservoir portion of the fluid vials 422 project below the horizontal surface 421, permitting the optical sensors to visualize an identity code 425, e.g. a barcode or RFID tag of a fluid vial as well as to sense the fluid level 427 of fluid within the fluid vial (e.g., meniscus). In some variations, electroluminescent panels 429 may be positioned below the horizontal surface 421 of the reagent storage frame 107 to provide additional illumination to aid sensing. Also visible in FIG. 4B is the magnetic arm controller 432 of the magnetic field applicator 119.

Figure 5A:
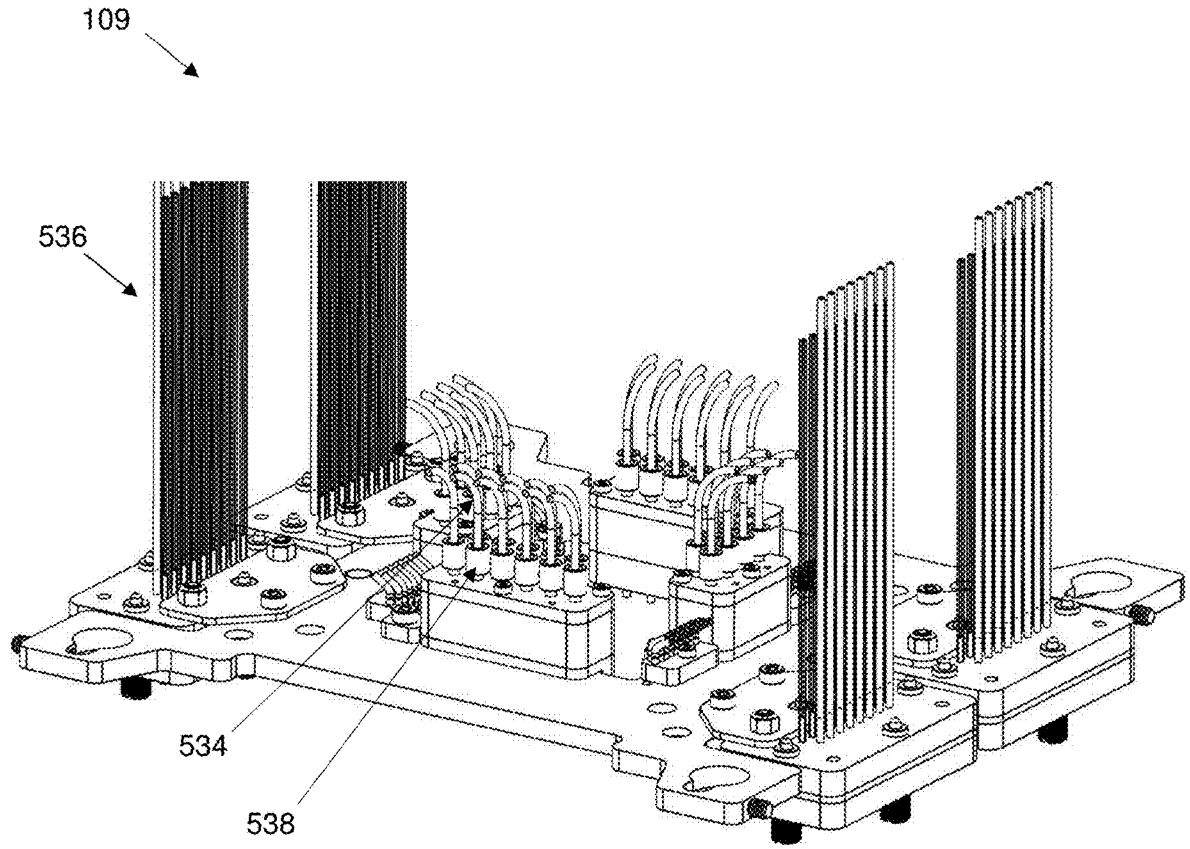
FIG. 5A is an isometric view of one example of an upper surface (e.g., top) of a reagent storage frame.
Figure 5B:
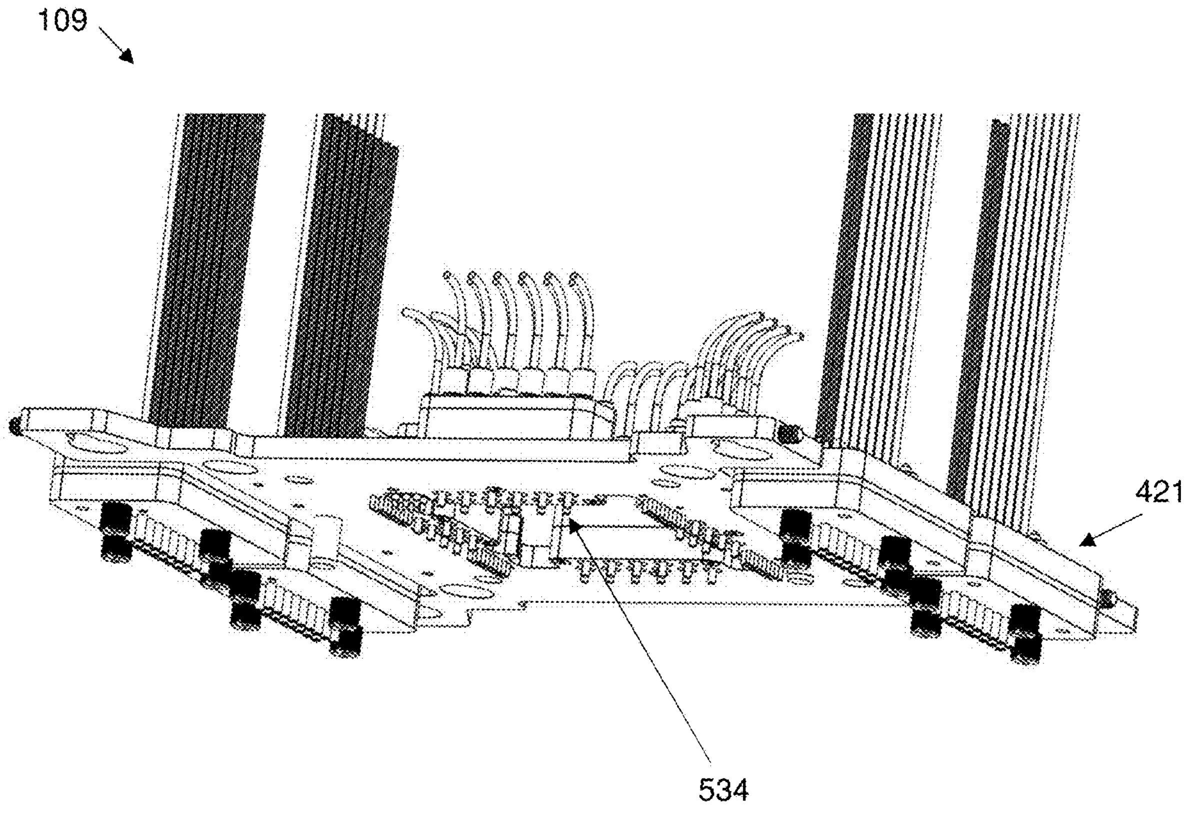
FIG. 5B is an isometric view of the lower surface (e.g., bottom) of the reagent storage frame of FIG. 5A.

FIG. 5A shows a perspective view of the top surface of a fluid interface assembly 109 of apparatus 100, 200, 300. The fluid interface assembly 109 may include a plurality of fluidic lines 534 and pressure lines 536, wherein each fluidic line and each pressure line is configured to independently be driven against a microfluidic path device 111 seated in the seating mount 115 to make a sealing connection thereto. For fluidic lines 534, a biased spring within fitting 538 may provide the force to keep the fluidic line engaged against the microfluidic path device 111. FIG. 5B is a perspective view of the underside of the fluidic interface assembly 109, showing the fluidic lines 534 exiting from the underside of the horizontal surface 421 of the fluid interface assembly 109, to be engaged with the microfluidic path device 111. The fluid lines and the pressure lines may have a distal end for engaging with the microfluidic path device that is substantially flat, so as to form a good seal with the microfluidics path device.

Figure 6A:
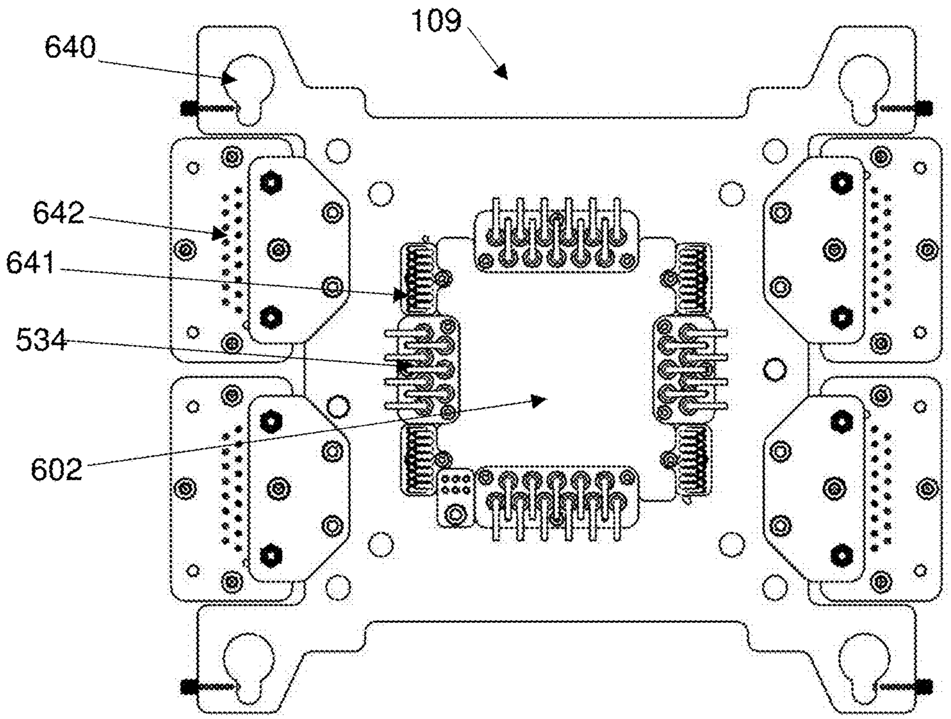
FIG. 6A is a top view of an example of a fluid interface assembly.
Figure 6B:
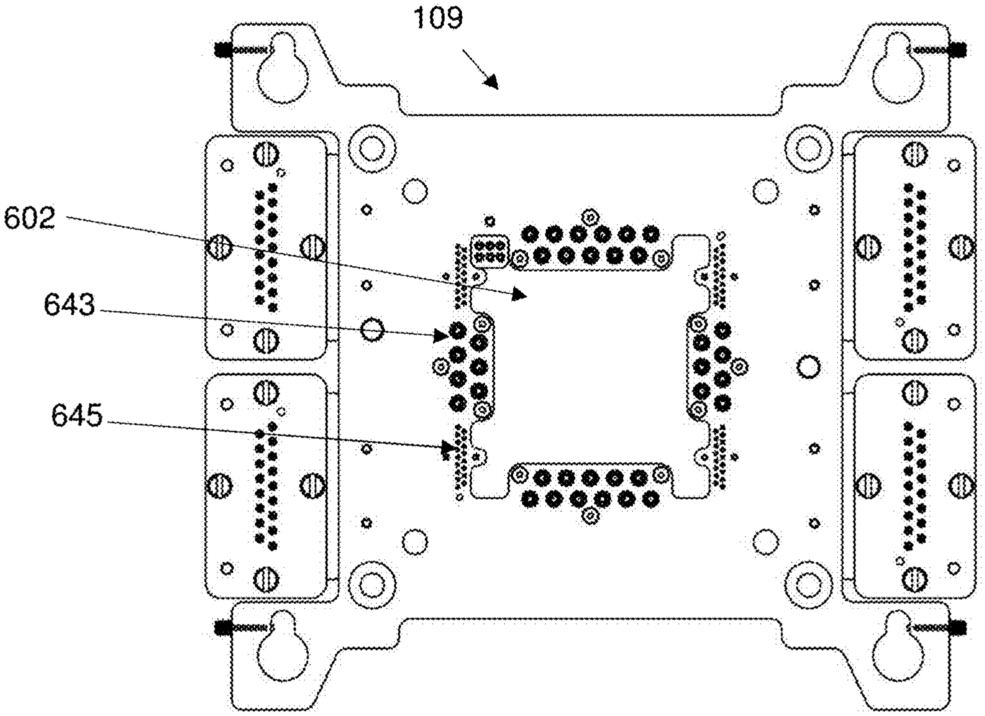
FIG. 6B is a bottom view of the fluid interface assembly of FIG. 6A.

FIG. 6A shows the top surface of a fluid interface assembly 109. The fluid interface assembly has a central opening 602 through which the microfluidic path device 111 may be imaged by one or more of the plurality of optical sensors. Pressure lines may pass through 642 may be located at the periphery of the fluid interface assembly (pressure lines not shown) and fluidic lines 534 and pressure lines 641 are arranged for input to the microfluidic path device 111 around the periphery of the central opening 602. FIG. 6B shows the bottom surface of the fluid interface assembly which shows the sealing end exit points 643 for fluidic lines 534 and sealing end 645 of pressure line 536 are arranged around a periphery of the central opening 602.

Figure 7A:
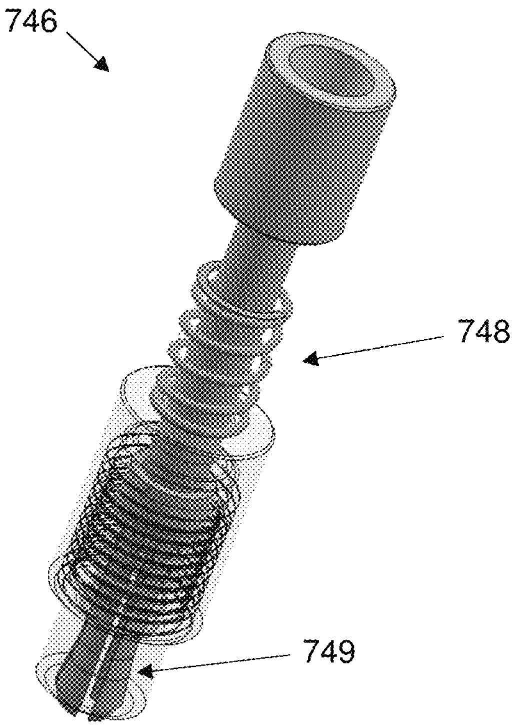
FIGS. 7A-7B are perspective and side views, respectively of a tubing compression connector assembly configured as a bias (e.g., a spring bias) that is configured to urge a fluidic line against a microfluidic path device to make a sealing connection thereto.
Figure 7B:
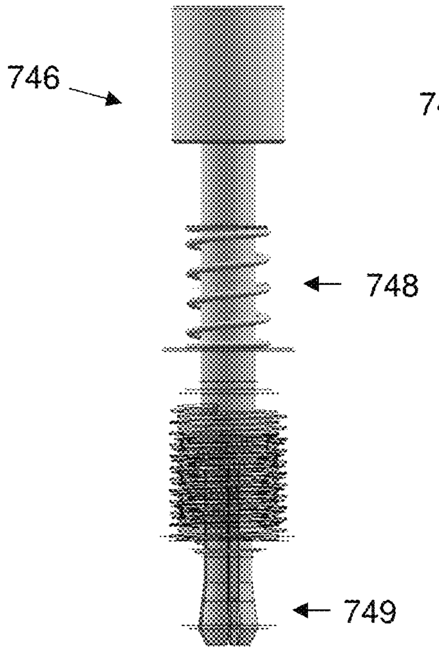
Figure 7C:
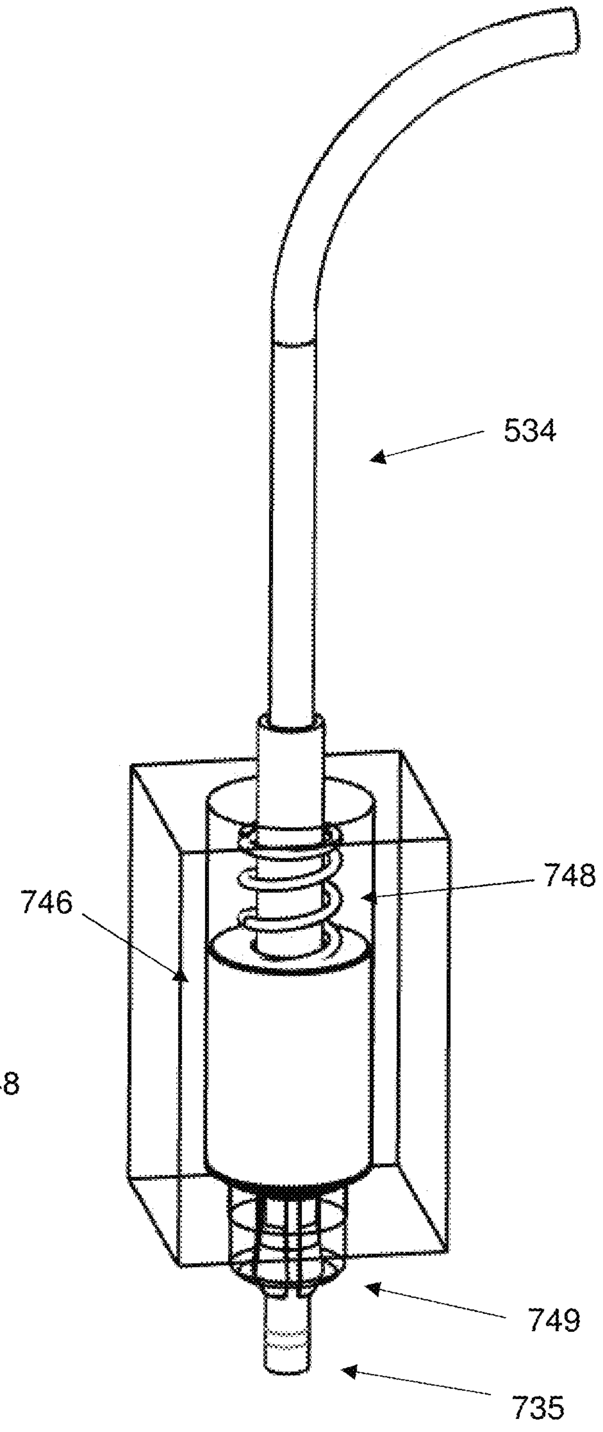
FIG. 7C is a graphical representation of tubing held engaged within a tubing compression connector (e.g., collet) similar to that shown in FIGS. 7A-7B.

FIG. 7A shows a fitting 746 that may be used to engage a fluidic line 534 against the microfluidic path device 111 seated in the seating mount, in order to make a sealing connection within the microfluidic path device 111. The fitting 746 includes two mechanisms to provide a robust sealing connection that minimizes leaks while providing flexibility for the fluidic line 534 secured therein, which minimizes fluidic line stress during setup and operation of the apparatus. A spring bias 748 may be employed to urge the fluidic line against the microfluidic path device. Additionally, a collet 749 may be employed to urge the fluidic line 534 against the microfluidic path device 111. The microfluidic line 534 may be terminated in a flat cut to engage cleanly against the microfluidic path device 111. In some variations, both of these mechanisms may be used to secure the fluidic lines. In other variations, the spring bias 748 may be used. A collet 749 may be used to enhance gripping (e.g., in one direction), so that even as the fluid and/or pressure line is driven against the microfluidic path device, the fluid and/or pressure line may be prevented from backing out of the microfluidic path device and breaking the seal with the microfluidic path device. In yet other variations, other suitable connectors may be used to engage the fluidic lines against the microfluidic path device such as a gasket or other kind of compression seal. FIG. 7B shows a side view of the fitting including spring bias 748 and collet 749. FIG. 7C shows a graphical representation of the fitting 746 having a fluidic line 534 engaged. Spring bias 748 is engaged against the fitting base and collet 749 grips fluidic line 534. The flat cut end 735 is pushed past the collet 749 in order to engage against the microfluidic path device 111.

Figure 7D:
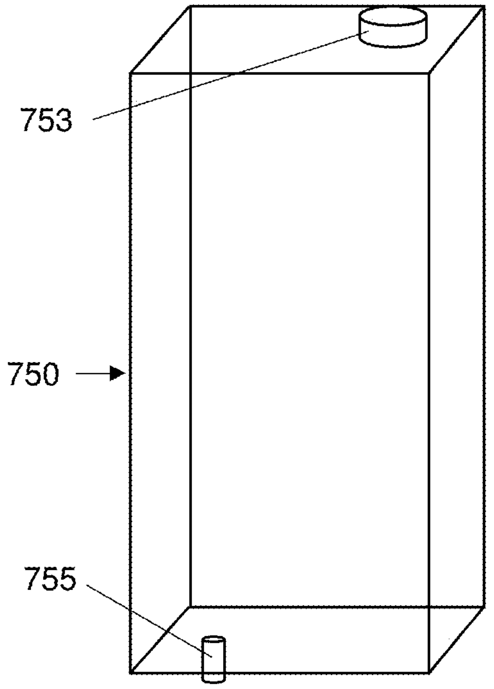
FIGS. 7D-7E illustrate an example of a fluid cartridge that may be held in spring contact with port (e.g., fluid port) of a microfluidic path device.
Figure 7E:
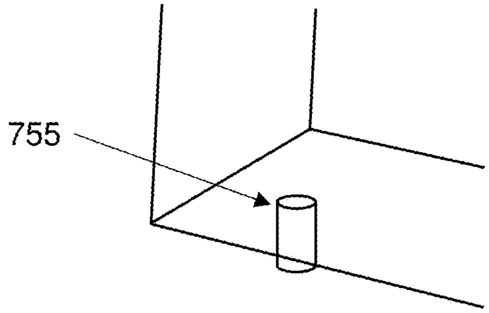

In some variations, all or some of the fluidic lines and fluid vials may instead or additionally be configured as fluid cassettes that connect to the microfluidic path device 111. Any of these fluid vials (e.g., fluid depots) may be configured so that the fluidic depot comprises a fluidic line integrated as part of the fluidic depot. One example is shown in FIGS. 7D-7E, where fluid cassette 750 may have a pressure port 753 and a flat cut or flat molded fluidic input port 755. This fluidic input port is configured as a channel that comprises a fluidic line 755 integrated into the rest of the fluid depot/fluid vial 750. The fluidic input port 755 (shown as an integrated fluid line in FIGS. 7D and 7E) may be held with bias (e.g., in some variations, spring loaded) against the microfluidic path device 111, to contact and seal against the elastomeric layer (e.g., elastic layer) within the microfluidic path device 111 at the port. As mentioned above, the bias force (also referred to as the valve closing pressure) may be greater than the pressure within the fluid vial/fluid line and pressure line, to prevent leaking (e.g., greater than 2 psi, 5 psi, 7 psi, 10 psi, etc.) than the pressure in the fluid line/fluid vial or pressure line. For example, the port of the microfluidic path device may be configured to receive a pressure of to about 5 psig (e.g., 5 psig, 7 psig, 10 psig, 12 psig, 15 psig, etc.), which may be slightly higher than the pressurization for a fluid vial 422 as described herein. In some variations the fluid vial (e.g., fluid cassette) 750 may not require mounting on a separate reagent storage frame but could be spring mounted upon the device 111 directly or on the fluid interface assembly 109, which could reduce or eliminate tubing. The bias contact with the elastic layer of the microfluidic path device 111 could initiate a seal opening for the fluid cassette for use. The fluid cassette 750 could facilitate barcoding and identification thereof. Use of a plurality of fluid cassettes 750 could simplify the structures needed to supply reagents within the microfluidic path device 111. This design may enable the use of an isolating sterile inner liner within the fluid cassette 750, which could eliminate exposure of a reagent stored therein from the gas used to pressurize the fluid cassette. Alternatively, other fluid cassette designs could achieve the same isolation from exposure to the gas, by use of a low sliding force piston or other structural features which could separate the reagent held within the fluid cassette 750 from the gas used to drive the fluid into the microfluidic path device. FIG. 7E shows an enlargement of the fluidic input port 755, which engages the microfluidic path device directly. In any of the variations, unless the context makes it clear otherwise, the phrase "fluidic lines" may include either or both a fluid cassette (also referred to as a fluid vial) and/or tubing connected to a fluidic source (e.g., depot, such a bottle, vial, tube, etc.).

Figure 8A:
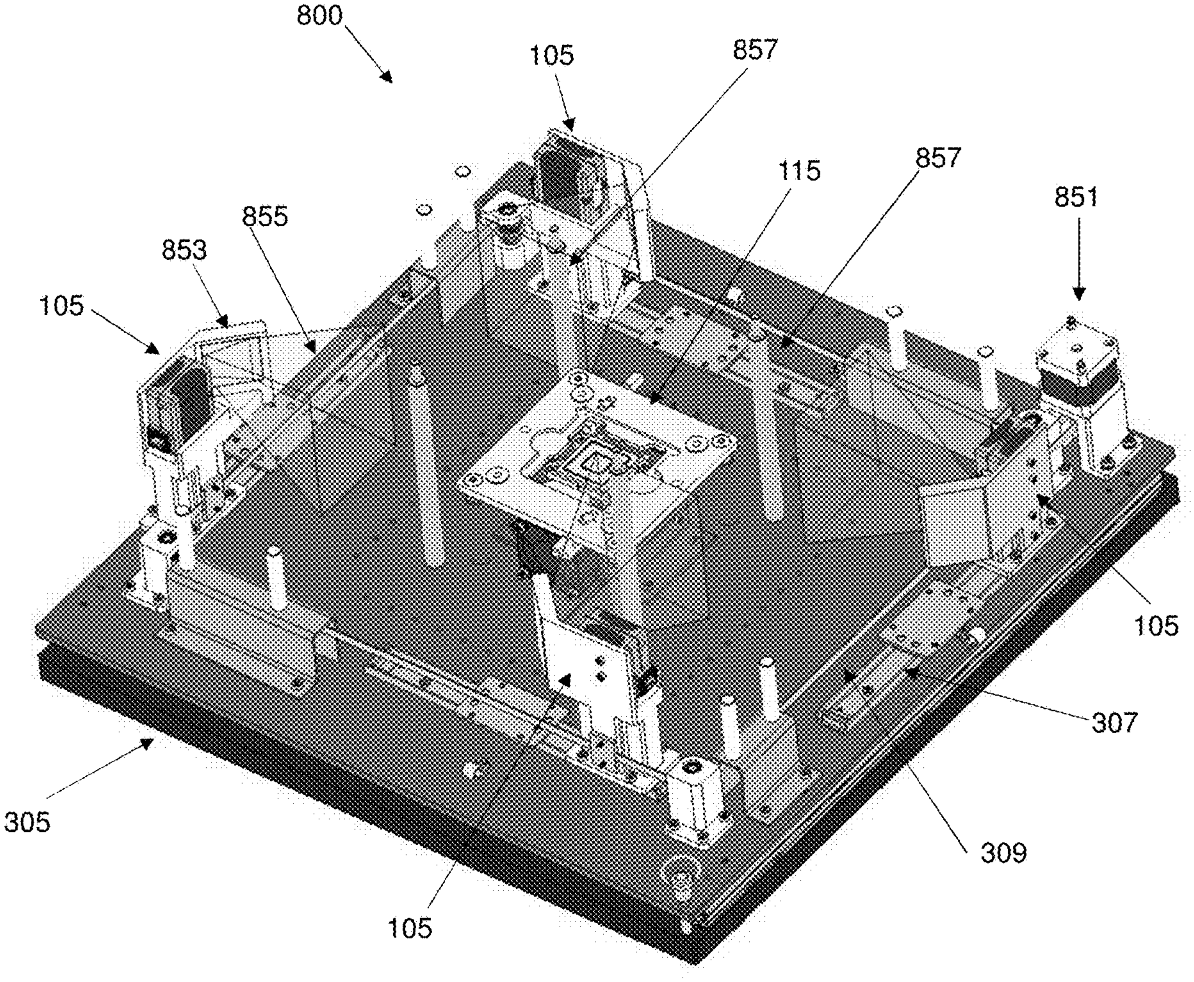
FIG. 8A is an isometric top view of one example of a seating mount, a plurality of optical sensors arranged around the seating mount on a gantry, and a thermal control beneath the seating mount, as described herein.
Figure 8B:
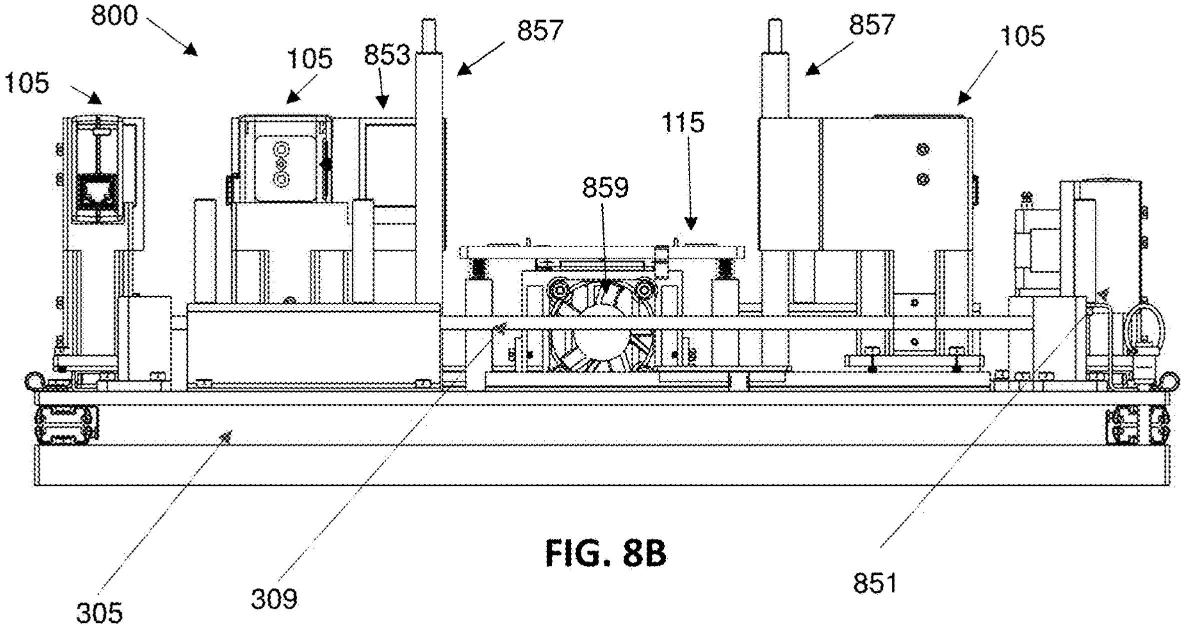
FIG. 8B is a side view of the sub-assembly (including the seating mount, optical sensors, and thermal control) of FIG. 8A.
Figure 8C:
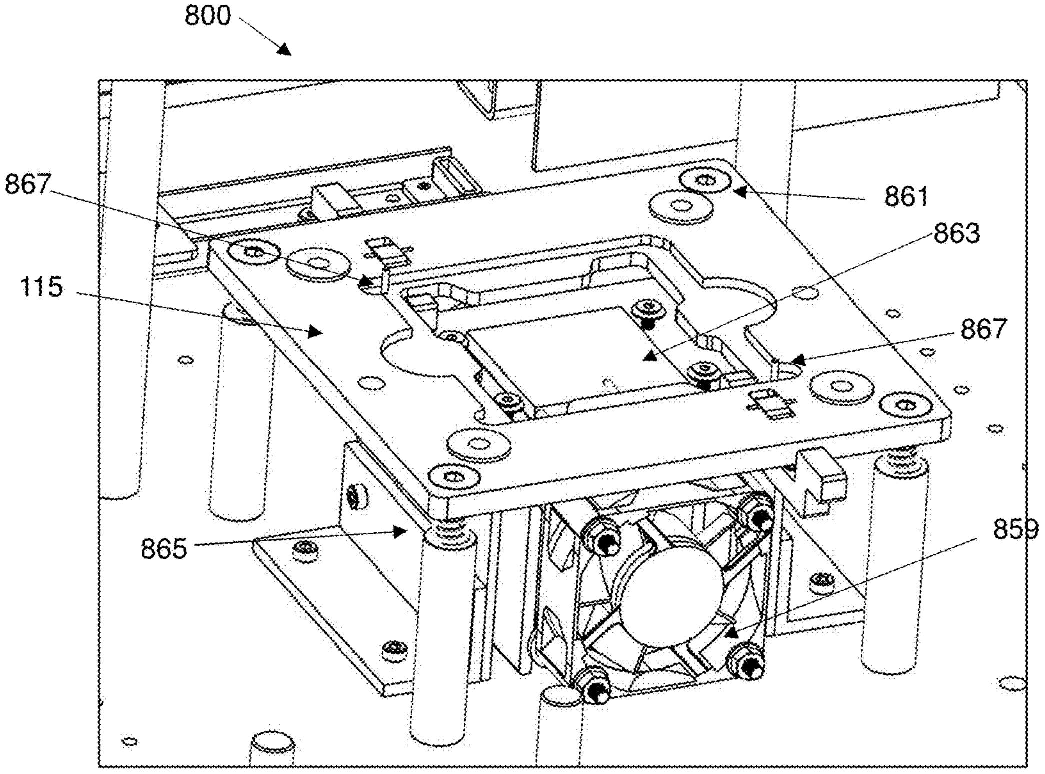
FIG. 8C is a detail view of the seating mount according of FIG. 8A.

FIG. 8A is a perspective view of a bottom substrate 800 of the apparatus of FIG. 1, 2, or 3, showing the base 305 to which seating mount 115 and a plurality of optical sensors 105 are connected. In this view, four optical sensors 105 may be positioned around each edge of the base, and may be configured to move along a gantry including one or more rails 307 to image along a region surrounding the seating mount and reagent storage frame, when in place. The optical sensors 105 may be driven along rail 307 by optical sensor drive 851. The optical sensors may be driven in unison by optical sensor drive belt 309. Each of the optical sensors 105 has an angled mirror assembly 853, which permits imaging of a field of view 855, while minimizing the space taken up by the optical sensor 105 itself. The bottom substrate 800 in this example also includes a second set of aligning pins 857, which may help to align the fluid interface assembly and the reagent storage frame with the seating mount. FIG. 8B is a side view showing the arrangement of the base 305, optical sensors 105 (three visible in this view), optical sensor drive belt 309, and optical sensor drive 851. The second set of aligning pins 857 frame the area around the seating mount 115, and cooling fan 859 of the thermal control 113 is visible beneath the seating mount 115. FIG. 8C shows a detail view of components arranged on the bottom substrate 800. Seating mount 115 is secured by mounting springs 865 to be supported at a desired orientation and to place the opening where the microfluidic path device will be lodged at the level of the thermal control, e.g., Peltier surface (thermal control surface) 863. Seating mount 115 may be secured to the mounting springs 865 releasably, having release levers or connectors (not shown) which will permit the seating mount 115 and fluidic interface assembly 109 (e.g., upper nest) to be removed and sterilized between uses, for example by autoclaving. Aligning holes 861 may be present on the seating mount 115 for aligning the microfluidic path device 111 for proper seating within the seating mount 115. The aligning holes may be near to the outer edge of the seating mount 115. Alignment dowel pins may also be included. The thermal control surface 863 may also include or be configured to include a vacuum chuck; vacuum grooves may be present in the upper surface so that vacuum may be applied to suck a microfluidic path device down in good thermal contact with the thermal control surface 863.

In general, a seating mount may be referred to as simply a 'seat' and is configured to seat one or more microfluidic path devices, either secured or unsecured within the apparatus.

The microfluidic path device 111 may, in some variations, be supported at a substantially horizontal orientation or may be supported at an orientation within about 1, 2, 3, 4, 5, 7, 9, 10, 11, 13, or about 15 degrees of a horizontal plane, to assist with control of bubbles. Fan 859 is visible below the seating mount 115.

As mentioned above, the apparatus (e.g., system, apparatus or device) may include a controller. The controller may be configured to control the application of pressure through the pressure lines to drive fluidic movement in the microfluidic path device when the microfluidic path device is seated in the seating mount. The controller may be configured to be in communication with the optical sensors and may sense the identity of a code on a fluid vial or may sense the identity of a code on the microfluidic path device. The code on the fluid vial and/or the microfluidic device may be an optical code or may be a RFID code. The controller may be configured to be in communication with the optical sensors and may sense a level of reagent in a fluid vial. The controller may be configured to send instructions to the optical sensor drive to position the optical sensors selectively for sensing a code or for sensing a fluid level within a fluid vial disposed on the reagent storage frame. The controller may be configured to control a time of introduction of a reagent within the microfluidic path device. The controller may be configured to control a volume of the reagent to be driven within the microfluidic path device. The controller may be configured to control positive pressure of a gas to at least one fluidic input of the microfluidic path device. The controller may be configured to sequester at least a portion of a product within a sub-region of the microfluidic device for export. In some variations, the controller may be configured to perform an in vitro transcription (IVT) reaction in the microfluidic path device. The controller may also include memory, one or more datastores.

The apparatus may include one or more processors configured to instruct and/or control the apparatus. The one or more processors may also analyze information from the apparatus and/or microfluidic path device.

The apparatus may include a user interface for at least one of inputting/exporting instructions and information about the status of the apparatus, identity of reagents within the apparatus, workflow being performed. In some variations, the apparatus may include a graphic user interface configured to provide input to the processor.

The apparatus may also include a remote database for storage and retrieval of data and images. The identity codes, visual log and other information may be stored in any format suitable for operation of the apparatus and/or for fulfilling regulatory requirements for manufacturing and formulating personalized therapeutics.

In general, the apparatus described herein may include one or more single-use microfluidic path device(s), as well as reusable components or sub-systems; selected portions of these sub-systems may be sterilized. For example, one or more of the fluid sample holders (all or a portion thereof, such as the fluid container holder(s), tubing, etc.), fluid interface assemble (all or a portion thereof), and/or the seating mount for a microfluidic path device (all or a portion thereof, such as the seating portion) maybe removable, sterilizable and replaceable. The apparatus may be configured to allow these one or more regions to be released and removed from the apparatus. For example, the apparatus may include a seating mount release control configured to release the seating mount from the apparatus so that it can be separately sterilized and/or a fluid interface assembly release control configured to release the fluid interface assembly from the apparatus so that it can be separately sterilized, and/or a fluid sample holder release control configured to release the fluid sample holder from the apparatus so that it can be separately sterilized. The release mechanism may be a locking release, one or more screws, pins, hinges, etc. Any of these apparatuses may be configured to allow portions to lift away from other regions of the apparatus (either automatically, manually or semi-manually, including an integrated guide or mount that supports the various portions of the apparatus, allowing access and removal/replacement of certain components such as all or part of the seating mount, fluid interface assembly and/or fluid sample holder.

Microfluidic Path Device

The apparatuses described above are configured to support and control operations in a microfluidic path device to perform processing of polynucleotides. The polynucleotides may be any kind of polynucleotides, including but not limited to ribonucleic acids, deoxyribonucleic acids and the like. The polynucleotides may include only natural nucleotide units or may include any kind of synthetic or semi-synthetic nucleotide units. Processing may include, but is not limited to in-vitro synthesis, purification, concentration, formulation and analysis.

Figure 9A:
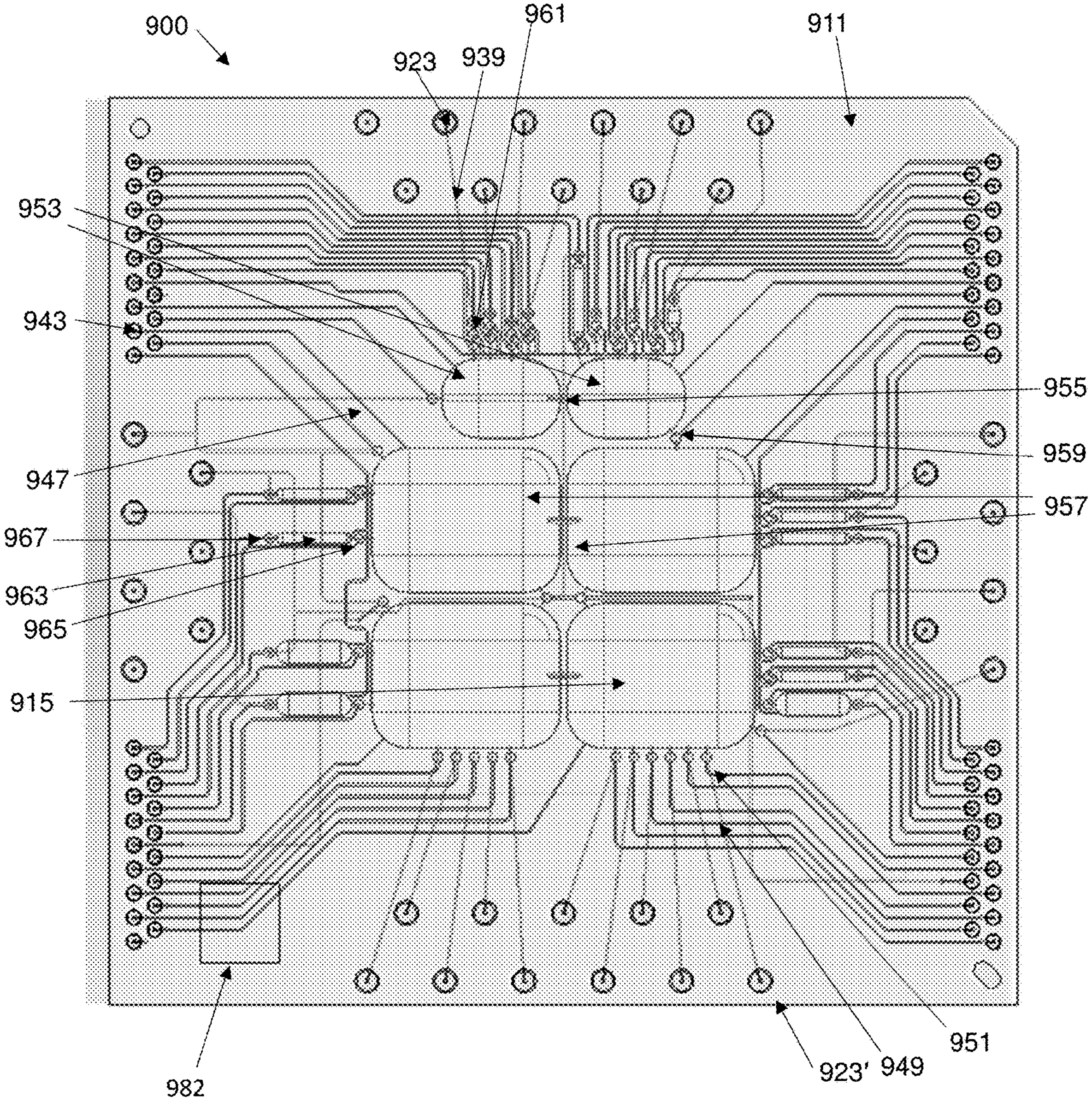
FIG. 9A is a top view of one example of a microfluidic path device.
Figure 9B:
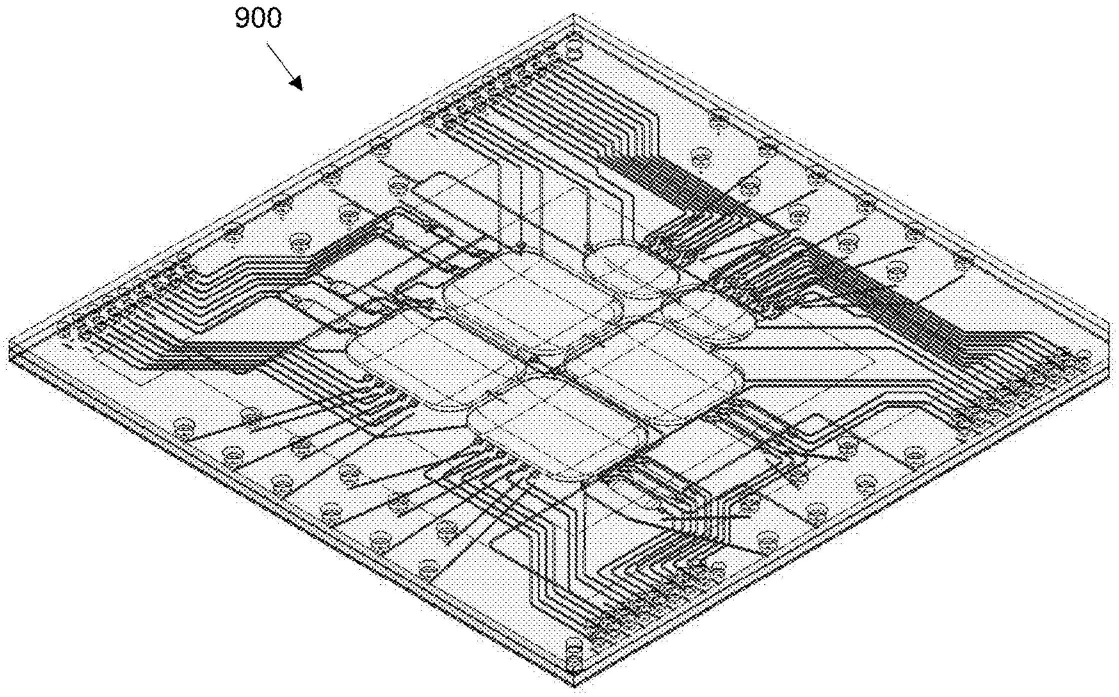
FIG. 9B is an isometric view of the microfluidic path device of FIG. 9A.

An example of a microfluidic path device for synthesizing therapeutic polynucleotides in a closed path is shown in FIGS. 9A-9B, 9F, 10A-E, and 11, where FIG. 9A is a view of an upper surface 911 of the device 900, looking down through the multiple layers forming the device 900, and FIG. 9B is a perspective view of the device 900. FIGS. 10A and 10C-10H are side views through the layers of the device 900, illustrating one example of an arrangement of the layers and channels, chambers and ports formed therethrough.

Figure 10A:
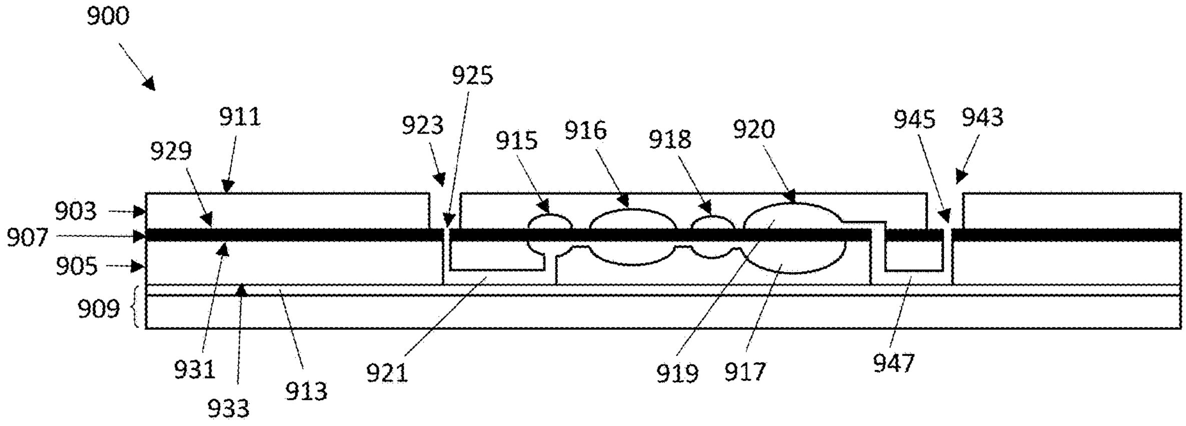
FIG. 10A is a side sectional view through one example of a microfluidic path device.

FIG. 10A illustrates one example of an arrangement of the layers of a microfluidic path that form the seals, channels, valves, and chambers, including pumping chambers. In general, these apparatuses may advantageously be formed of a rigid or semi-rigid plates and at least one elastic layer. The elastic layer may be a sheet of elastic material that is liquid-impermeable. The elastic layer maybe somewhat gas permeable, or may be treated to be more or less gas permeable in various regions. Although a single continuous sheet of elastic material may be used, in some variations multiple elastic materials sheets may be used, or the 'sheet' may be formed of sections of multiple sheets. The layers and the elastic sheet may be laminated together. In general, chambers for holding, valving and/or pumping fluid may be formed in the plates on either side of the elastic layer so that the elastic layer bisects the chambers into a liquid containing side and a pressure (e.g., gas) applying side. The overall volume of chamber(s) may be constant, and may be formed into both the first (e.g., upper) plate and the second (e.g., lower) plate, but this volume may be divided into the pressure side and the liquid side. By applying positive or negative pressure into the pressure side, the elastic sheet may be deformed to make reduce (down to zero, closing the chamber off) the volume of the liquid containing side or to increase the volume of the liquid containing side (to a predetermined maximum). The pressure applying side of the chamber may be connected, e.g., via a pressure channel in the upper plate (or between the upper plate and the elastic layer) to a pressure port, e.g., for applying negative or positive pressure. The liquid containing side may be connected via a fluid channel to a fluid port, as described herein. As will be described in greater detail herein, both the fluid port and the pressure port may be formed by an opening into the upper plate and the elastic layer, allowing a sealed connection that is isolated from the atmosphere even when there are multiple different input lines.

In FIG. 10A, the microfluidic path device 900 includes a first (e.g., upper) surface formed on one side of a first plate 903. The first plate includes a first (e.g., top or upper) surface 911 and a second (bottom or lower) surface 929 and a thickness between the two. The first surface 911 may form an exposed outer surface. The microfluidic path device also includes a second plate 905 having a first (e.g., upper or top) surface 931 and a second (e.g., lower or bottom) surface 933 and a thickness therebetween. An elastic layer 907 is sandwiched between the second surface 929 of the first plate 903 and the first surface 931 of the second plate 905. A third plate 909 is coupled to the second plate on the second surface 933 of the second plate, either directly or indirectly. The third plate 909 also has a first (e.g., upper or top) surface and a second (lower or bottom) surface and a thickness therebetween. The second surface of the third plate may form a bottom surface of the microfluidic path device. Any of the plates may be formed of multiple layers, which may be laminated or otherwise connected together. For example, in FIG. 10A, the third plate 909 includes an optional second elastic layer 913 which may help couple the third plate to the second plate; the second elastic layer 913 in this example forms the first surface 935 of the third plate 909. The layers and plates shown in FIG. 10A may not be to scale (e.g., the elastic layer 907 may be thinner relative to the plates).

The microfluidic path device 900 shown in FIG. 10A may also include a plurality of chambers 915, 916, 918, 920 each having a fixed volume. These chambers are formed by cut-out regions (e.g., rounded/curved cuts) into the second (bottom) surface 929 of the first plate 903 and the first (upper) surface 931 of the second plate 905; the elastic layer 907 bifurcates these chambers 915 so that each includes a liquid containing side 917 and a pressure (e.g., gas containing) side 919. The microfluidic path device 900 may also include multiple liquid (e.g., fluid) channels. In FIG. 10A, a single fluid channel 921 is shown extending from a fluid port 923 passing through the thickness of the first plate 903, to a fluid channel opening 925 through the elastic layer 907 and through much of the thickness of the second plate 905 down to the bottom surface 933 of the second plate where a length of the liquid channel 921 running parallel to the bottom surface of the third plate is formed in the bottom surface 933 of the second plate, and bounded by the upper surface of the third plate 909.

In regard to the fluid port 923, the diameter of the opening into the first plate 903 forming the fluid port 923, which extends through the thickness of the first plate, may be larger than the diameter of the fluid channel opening 925 which extends through the elastic layer 907 and into the liquid (e.g., fluid) channel 921. The fluid channel opening 925 may be centered relative to the bottom of the fluid port opening, and may be offset from the walls of the fluid port opening by at least the expected wall thickness of the fluid line or fluid line coupling interface that will connect to the fluid port.

The fluid channel 921 connects to the liquid containing side 917 of a first chamber 915. This first chamber may be configured as a valve, which has a relatively low retaining volume (fixed volume), but can be fully opened or closed by the movement of the elastic layer 907.

The microfluidic path device 900 also includes a plurality of pressure channels that may be independently controlled to apply positive and/or negative pressure. In FIG. 10A, a single pressure port 943 is shown, connected to the fourth chamber 920, although each of the chambers 915, 916, 918 may be connected to a separate pressure port and pressure channel for independently operating and controlling the movement of the portion of the elastic layer 907 bifurcating these chambers, to valve, and/or pump each chamber independently. In some variations the pressure ports may be shared between multiple chambers. In FIG. 10A the pressure (e.g., gas) port 943 is similar to the fluid (e.g., liquid) port 925, and includes an opening completely through the first plate 903, down to the exposed elastic layer 907, to an opening through the elastic layer forming a pressure (e.g., gas) channel opening 945. The pressure channel opening 945 is continuous with a pressure (e.g., gas) channel 947 that extends from the pressure port 943, passing through much of the thickness of the first plate 903, and in a cut-out channel along the bottom of the second plate (or alternatively into a cut-out region in the top of the third plate) and back up through the second plate and the elastic layer 907, to a region of the pressure channel within the first plate that connects to the pressure (e.g., gas) containing portion 919 of the fourth chamber 920. As described for the similar fluid (e.g., liquid) port, the diameter of the pressure port 943 passing through the thickness of the first plate 903 may be larger than the diameter of the pressure channel opening 945 through the elastic layer 907, and may be centered or offset by greater than the wall thickness of a pressure line or pressure line coupling interface that will connect to the pressure port.

In the section through a microfluidic path device 900 shown in FIG. 10A, there are multiple connections to other fluid (e.g., liquid) lines, fluid ports, pressure lines and pressure ports that are not shown, as they may be out of the plane shown. For example, in FIG. 10A the liquid containing side or portion 917 of the fourth chamber may be connected to additional valves (chambers) and/or channels, including, e.g., an exit channel extending from the liquid containing side 917. An additional chamber (e.g. configured as a valve), no shown may be formed as described above. In some variations, an exit channel may deliver fluid from the one or more chamber through another fluid port (not shown) to a fluid receiving depot, e.g., a vial, tube, etc. This receiving depot may be held in the reagent storage frame.

In general, this configuration of the microfluidic path device and the microfluidic apparatus is configured so that multiple, complex steps may be executed by the apparatus on the microfluidics path device in a fully enclosed (sealed and protected from atmosphere) manner, without requiring any manual intervention. Fluid may be metered using the fixed-volume chambers and moved, mixed, filtered, etc. by applying pneumatic pressure to deflect regions of the elastic layer.

Returning to FIG. 9A, a microfluidic path device 900 may include at least one pair of chambers 953, each of which may be like clamber 920, including liquid (fluid) side 917, a pressure (e.g., gas) side 919, fluidic connections, pressure connections and fluidic/pressure lines as described above. Further each of the pair may be connected to each other by a fluidic connector 955. The fluidic connector 955 may be used in coordination with positive and/or negative pressure applied to the pressure side of the chamber(s) to drive liquid in the liquid side between the two chambers to mix this liquid within each of the chambers. Deflecting the elastic layer between the fixed volume of a chamber bifurcated by the elastic layer may drive any liquid within the liquid between the two chambers.

Any of the microfluidic path devices described herein may include one or more connections for an electronics, including electrical sensors, on the device. For example, in FIG. 9A, the microfluidic path device may include a region 982 that is configured to include one or more electrical contacts for communication with one or more sensors (or other electronics) on the microfluidic path device. In some variations the electronics may include electrical circuits or the like. The electrically active region 982 may include one or more conductors for making electrical contact with the apparatus; the electrical contacts may provide power, data, etc. For example, the electrically active region may be configured as one or more contact pads for connecting to one or more connector pins (e.g., spring-loaded or otherwise biased connector pins) that may be attached to or part of the upper nest (e.g., the fluidic interface assembly).

The microfluidic path device 900 may include more than one pair of chambers, wherein each pair of chambers may be used for different processes applied to polynucleotides. For example a first pair of chambers 953 may be used for synthesis of the polynucleotides. A second pair of chambers 955 may be used for purification of the synthesized polynucleotides. Fluid from a first pair of chambers 953 may be driven to a second pair of chambers upon application of pressure to the pressure-receiving side 919 of the respective chambers and opening a valve 959 between the first pair of chambers 953 and the second pair of chambers 955. The valve chamber 959 may be formed by the elastic layer 907 within a connector channel between the two pairs of chambers.

A microfluidic path device 900 as shown in FIGS. 9A and 9B may have a plurality of pressure ports 943 and fluid ports 923. The plurality of pressure ports and fluid ports may be disposed adjacent to a periphery of the microfluidic path device, and are configured to be connected to the fluid interface assembly 109 as described above.

Ports (e.g., sealing valves) may be formed from the elastic layer as described above, along the length of a connecting channel 939 (either pressure channel or fluid channel), such as is shown in FIG. 9A, for valve 961, which may control timing of delivery of a reagent driven from fluidic port 923, but when placed in series with one or more similarly constructed valves, may also permit metering to the chambers of the device. For example, in FIG. 9A, three valve chambers are shown (described in greater detail below); the first of these three valves may act as a peristaltic pump, while the middle valve may be a metering chamber that meters small (e.g., having a metering volume of about 10 nL, 20 nL, 25 nL, 50 nL, 75 nL, 100 nL, etc.). The structure of the port and channel is illustrated in FIG. 10A, described above. The size of the channels, and particularly the size of the chambers connected to the channels) can meter out the volume dispensed along fluidic connecting channel 939, 921 and delivered into the chamber 953 that is connected to the fluidic connecting channel 939, 921. In some variations, a metered volume may be as little as 50 nL. Metered volumes of about 100 nL, 1 microliter, 5 microliters or more may be imported. A variety of valve sizes may be pre-selected for incorporation with in the microfluidic path device 900, and reagents may be connected to appropriate metering sizes by user choice.

Additionally, more than one valve body 961 may be included in a row along fluidic connecting channel 939. A series of valves 961 may act as a peristaltic pump to move fluid, including (but not limited to) viscus fluids. The ability to function as a peristaltic pump for fluids generally, may have particular advantage for moving fluid that may be viscous or contain suspended particles such as purification or capture beads.

As mentioned, a microfluidic path device 900 may also include a delivery or export reservoir or depot 963. In FIG. 9A, a pre-selected volume may be formed similarly to the chamber construction described above, or may contain only a metering side, as desired. In either case, valves may be used to meter desired volumes into the reservoir 963. Valve 965 can control delivery of fluid from reservoir 963. If larger volumes are desired, the delivery may be repeated. Alternatively, if reservoir 963 was pre-selected to be an export reservoir, valve 965 may open, and deliver fluid from chamber 957, while retaining valve 967 shut, which permits only the measured volume of fluid to be exported to reservoir 963. This fluid may then be exported to a fluid vial on the reagent storage frame for further processing or testing. In some variations, a chamber, reservoir or depot (e.g., 963) may be configured as a metering section of, e.g., a 1 μL pump formed by three valve structures (967, 965, 967). A chamber may be configured for export of waste, for example, from a mixing chamber 957.

An advantage of the microfluidic path device 900 can be the sealed path nature of its construction. While fluid vials, fluidic lines and the microfluidic path device are connected, operation of the apparatus may be performed without any exchange of materials in or out of the system, and in particularly in/out of the fluid path of the microfluidic path device for processing, including synthesizing a polynucleotide and preparing it for biological delivery (as a therapeutic, such as drug, vaccine, etc.). Thus the entire system may operate as a closed path and/or individual microfluidic path devices may operate in the system as a closed path (protected from the atmosphere).

Some variations of the processing that may be performed within the microfluidic path device 900 may include purification. One variation of purification can include incorporating a material within the fluid side 917 of a chamber or channel. The material may be configured to absorb selected moieties from the fluidic mixture in a chamber or channel. In one variation, the material may include a cellulose material, which can selectively absorb double-stranded mRNA from a mixture. The cellulose material may be inserted in only one chamber of a pair of chambers, such that upon mixing the fluid from the first chamber of the pair to the second chamber, double-stranded mRNA may be effectively removed from the fluidic mixture, which can then be transferred to another pair of chambers further downstream for further processing or export.

Some variations of the microfluidic device 900 may further include a concentrator within a chamber, which may be disposed within the thickness of the second plate and may be in fluid communication with an exit channel such as 949. The polynucleotides may be concentrated by driving off excess fluidic medium, and the concentrated polynucleotide mixture exported out of the microfluidic path device 900 for further handling or use. In some variations, the concentrator may be a dialysis chamber. For example, a dialysis membrane may be present within or between the plates of a microfluidic path device.

The microfluidic path device 900 may be formed of materials that are at least substantially translucent to visible and/or ultraviolet light. By substantially translucent is meant that at least 90% of light is transmitted through the material compared to a translucent material. In some variations, the microfluidic path device 900 may be formed of materials that are substantially transparent to visible and/or ultraviolet light. By substantially translucent is meant that at least 90% of light is transmitted through the material compared to a completely transparent material.

As mentioned above, the first plate and/or the second plate may be formed from a rigid material. The third plate may be formed from a rigid material. In some variations, the third plate may be formed from a rigid material laminated to an elastic material. The plates may be formed of the same material, or a different material(s). For example, the rigid material may be a polymer or glass. The polymer or glass may be biocompatible, e.g., does not leach any monomers or soluble small molecules that are toxic to living cells. The polynucleotide products processed within the microfluidic path device may be administered to an animal, so toxic contaminants are preferably reduced or eliminated by choice of materials. Any suitable biocompatible polymer may be used, including medical grade polycarbonate-urethane, silicone polycarbonate urethane, polyether urethane, amongst others. In some variations, the polymer may be a cycloolefin copolymer.

Figure 9C:
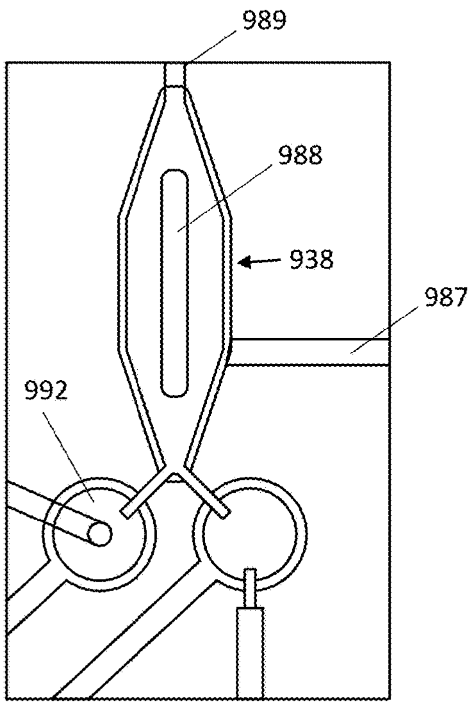
FIG. 9C illustrates an enlarged example of a portion of a microfluidic path device such as that shown in FIGS. 9A-9B, including a vacuum cap for bubble removal.
Figure 9D:
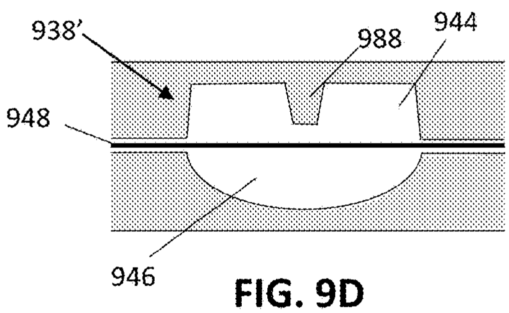
FIGS. 9D and 9E illustrate one example of a vacuum cap as descried herein.
Figure 9E:
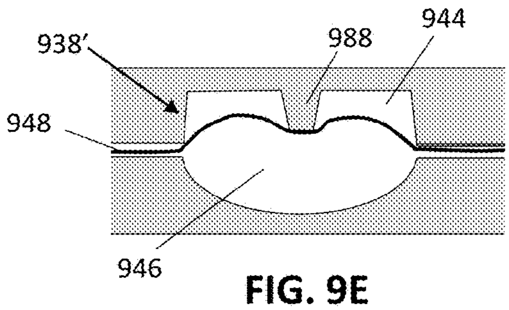
Figure 9F:
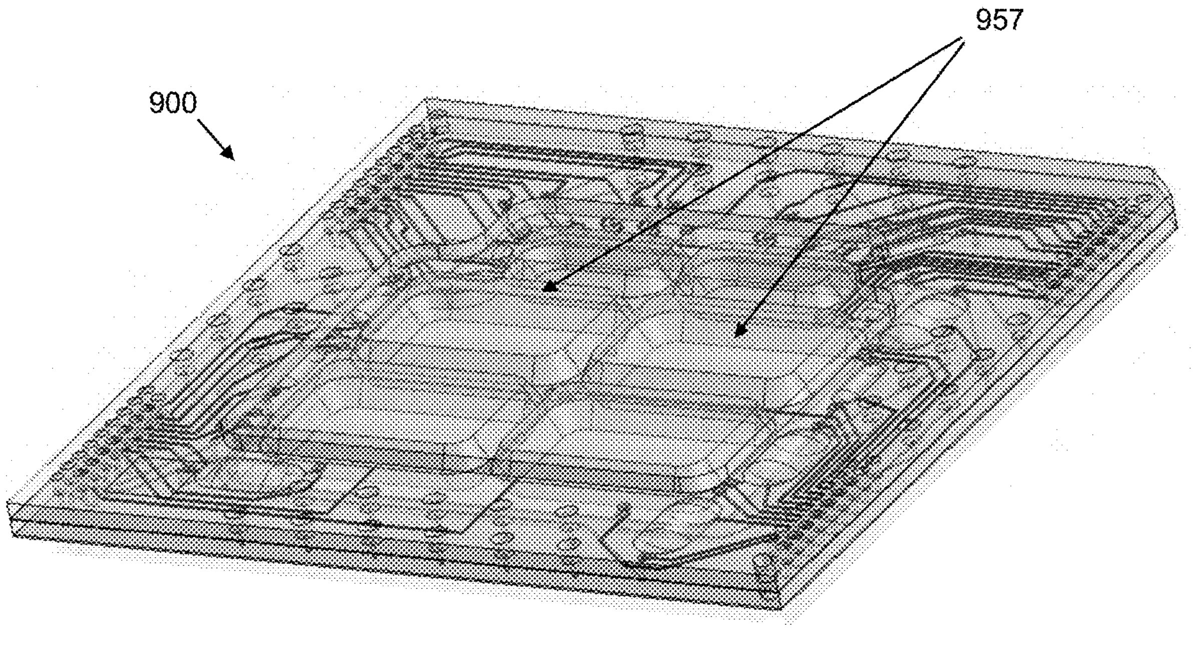
FIG. 9F shows another example of a microfluidic path device, configured as a high-volume device (e.g., "a 10× device").

FIG. 9F illustrates another example of a microfluidic path device 900 similar to that shown in FIG. 9A, but configured to process larger volumes. For example the device shown in FIGS. 9A-9B may be configured to process a particular amount per cycle of the device (e.g., 500 μg per IVT cycle), while the variation shown in FIG. 9F may be configured to process up to 5× this amount (e.g., 5 mg per IVT cycle). The larger-volume microfluidic path device shown in FIG. 9F may include chambers 953, 915 that extend slightly out of the device, so that the chambers, which are still divided up by an elastic layer into fluid-contacting sides and pressure-receiving sides, may be significantly larger. In FIG. 9F the area is approximately the same footprint, and may therefore be retained in the same seating mount as the device of FIGS. 9A-9B, but may hold and process significantly more fluid volume. The controller may be adapted to automatically determine the size(s) of the microfluidic path device chambers, and/or the type of microfluidic path device (e.g., template forming, IVT processing, etc.).

As mentioned above, the microfluidic path devices may be configured so that the chambers are formed of the upper and lower surfaces of one or more plates that extend somewhat out of the plane of the microfluidic path device, as compared to the variation shown in FIGS. 9A-9B. Any of the microfluidic path devices may be referred to herein as microfluidic path plate devices, as mentioned above. As used herein a plate may be generally planar, but may include one or more regions that extend up and out of the device, as shown in FIG. 9F.

Figure 10B:
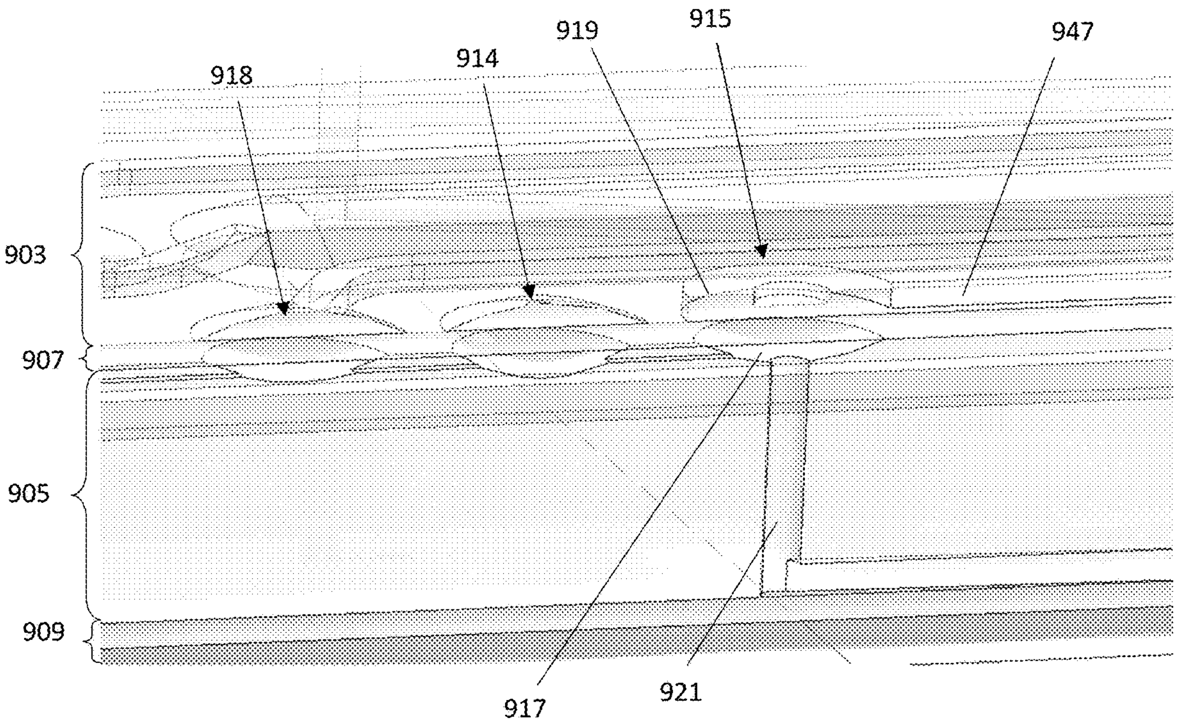
FIG. 10B is an example of section through a portion of one example of a microfluidic path device as described herein.

FIG. 10B illustrates on example of a portion of a microfluidics path device, shown partially transparent and in a perspective view. In this example, the device includes a first plate 903 having a first surface and a second surface and a thickness therebetween, a second plate 905 having a first surface and a second surface and a thickness therebetween, and an elastic layer 907 sandwiched between the second surface of the first plate and the first surface of the second plate. A third plate 909 is coupled to the second plate on the second surface of the second plate.

The portion of the microfluidics path device shown in FIG. 10B also includes sections through three chambers 915, 914 and 918, each having a fixed volume. The chambers are each formed in the second surface of the first plate and the first surface of the second plate, and a portion of the elastic layer bifurcates each chamber into a fluid holding side and a pressure-applying side. A fluid channel extends from a fluid port (not visible in FIG. 10B), and passes through the first plate to the elastic layer 907, to a fluid channel opening through the elastic layer and through most of the thickness of the second plate to fluidly connect with a connecting channel formed in the second surface of the second plate (or between the second plate and the third plate). This connecting channel may be bounded by the third plate. The fluid channel then extends back up through the second plate to connect to the fluid (e.g. liquid) holding portion one of the chambers, and preferably a chamber that is configured as a valve. In FIG. 10B, three chambers configured as valves are connected together, so that fluid may be pumped between them and metered in small volume (e.g., 10 nL). Negative pressure (or in some variations, zero pressure) may be applied to the pressure holding side 919 of the chamber 915 to open the valve, pulling the elastic layer up and into the upper (pressure holding) side of the chamber. Positive pressure may be applied to close the valve, deflecting the elastic layer bifurcating the chamber against the lower, curving, wall of the liquid-holding side of the chamber.

A pressure channel 947 may extend from a pressure port (not visible in FIG. 10B) that is formed as a channel through the thickness of the first plate down to the elastic layer 907. A pressure channel opening may be formed through the elastic layer and into the thickness of the second plate to fluidly connect with a connecting pressure channel formed in the second surface of the first plate (not visible in FIG. 10B) or between the second and third plate; the pressure channel may then extend back up (in a U-shaped path) through the second plate to a channel formed in the first plate (or between the first and second plate) to connect to the pressure-holding side of one or more chambers. The diameter of the fluid port passing through the thickness of the first plate is typically larger than the fluid channel opening through the elastic layer, and the diameter of the pressure port passing through the thickness of the first plate may be larger than the pressure channel opening through the elastic layer. Any of the microfluidic path devices may also include an exit channel extending from the fluid-holding side of a chamber or channel through the second surface of the second plate and/or through a chamber configured as a valve that can open to permit fluid within the channel or chamber to be pumped into a depot (e.g., a holder, bottle, container, vial, tube, etc.) that may be, e.g., in the rack of the reagent storage frame.

In any of the microfluidic path devices described herein, the fluid may pass from the top, though the first plate, through the seal formed by the elastic layer and through the second plate, then along the second plate and back up into a chamber (e.g., in some cases a chamber configured as a valve) bifurcated by the elastic. Similarly, the pressure flow (positive or negative) may pass from the top, though the first plate, though a seal formed by the elastic layer and through the second plate, along the bottom of the second plate, then back up through the second plate and elastic layer then along the bottom of the first plate to connect to a pressure-holding side of a chamber that is bifurcated by the elastic layer. In general the elastic layer may bifurcate a chamber by driving it equally or unequally; for example, the upper (pressure) chamber may be larger or smaller than the lower (liquid-holding) chamber. The application of positive or negative pressure to control the valves and/or pump or meter fluid within the chambers may be referred to herein as pneumatic or as pneumatic barrier deflection ("pneumodeflective").

Figure 10C:
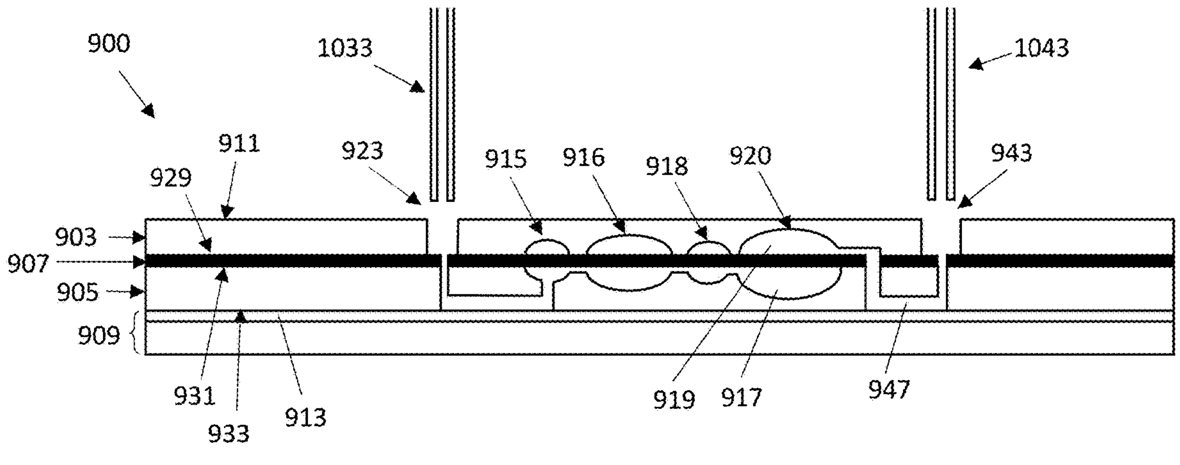
FIGS. 10C-10I illustrate operation of a portion of one example of a microfluidic path device interacting with a closed path microfluidic apparatus as described herein, shown in a side sectional view. In this example, a fluidic line and a pressure line engage with the microfluidic path device which may precisely control fluid movement in the microfluidic path device.

FIGS. 10C-10H illustrate the operation of a microfluidic path device (similar to the exemplary device shown in cross-section in FIG. 10A) engaging with a microfluidics apparatus, and in particular with a plurality of fluid 1033 and/or pressure lines 1043. In FIG. 10C, the microfluidic path device 900 is shown in cross-section; a plurality of fluid 1033 and/or pressure 1043 lines (two are visible in FIG. 10B) are shown approaching the microfluidic path device, each independently aligned with a pair of ports, including a fluid port 923 (to which the fluid line 1033 is aligned) and a pressure port 943 (to which a pressure line 1043 is aligned). In any of the variations described herein, the pressure and fluid lines may extend from a fluid interface assembly, as described above. Each pressure and fluid line may be coupled to an independently biased (e.g., biased towards the microfluidic path device) by a compression connector, as described above and illustrated in FIGS. 7A-7C. Because each fluid and pressure connection may be independently biased (e.g., is separately driven towards the microfluidic path device), but can be deflected up/down to push and seal against the exposed elastic layer that supported on one side by the rigid second plate, the pressure connection may form a highly tolerant seal between the pressure or fluid line, as shown in FIG. 10C. Thus, the apparatus is highly tolerant to alignment an orientation, allowing the device to be slightly displaced and/or angled relative to the fluid and/or pressure lines. The compression connector may also apply force against the supported elastic layer to hold the seal and prevent contamination or exposure to the outside environment. A bias element (such as a spring) may push the end of the fluid line or pressure line against the microfluidic path device. The closer the pressure line or fluid line is to the microfluidic path device, the more force is applied, however, each fluid or pressure line may be pushed back, e.g., up, at least slightly. Finally, the apparatus may be configured to mate with the microfluidic path device around the periphery of the microfluidic path device, which may distribute the forces and make a balanced and supported contact with the microfluidic path device all from the same side of the device.

Figure 10D:
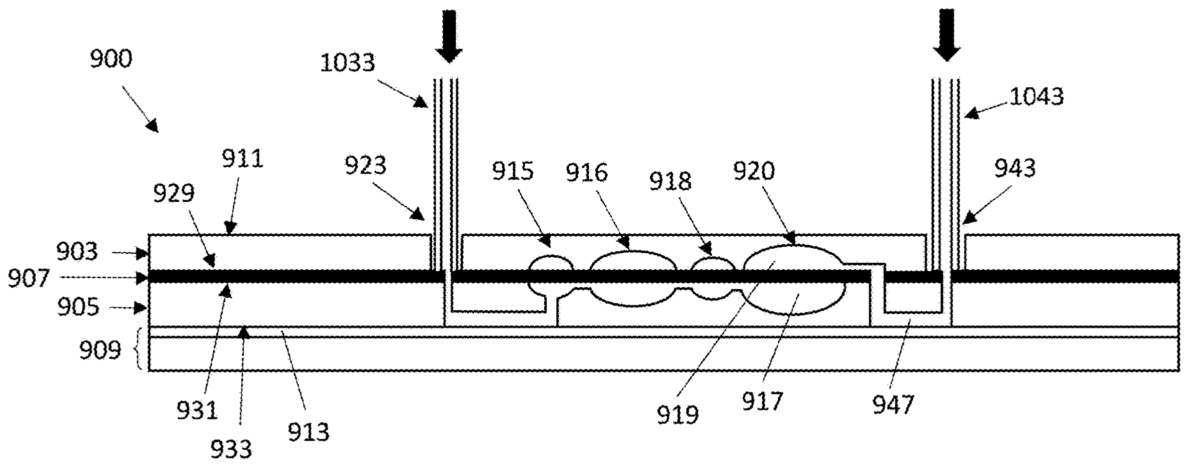
Figure 10E:
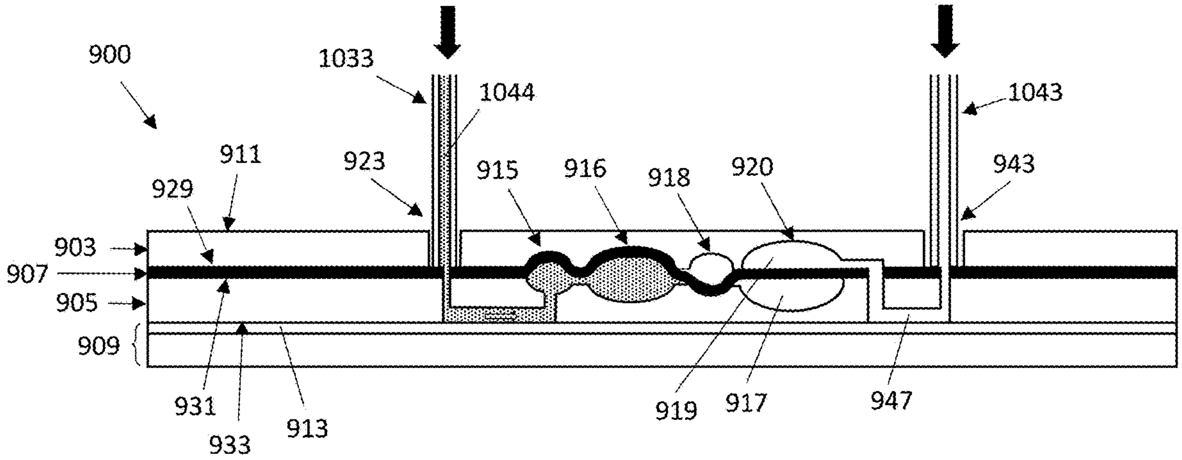

In FIG. 10D the fluid line 1033 and pressure line 1043 shown are driven against the fluid and pressure ports of the microfluidic path device with a spring bias, similar to that shown in FIGS. 7A-7D, so that the distal open ends are driven against the flat surface of the first elastic layer 907 of the microfluidic path device, that is supported beneath the elastic layer by the second layer. Each pressure and fluid line may therefore be separately driven (shown by arrows), e.g., by a spring or other biasing element, against the elastic layer, forming a seal against the elastic layer 907. Thereafter, the separate pressure and fluid lines may be independently controlled to apply fluid through the fluid line 939, and to valve and/or meter fluid within the microfluidic path device. For example, in FIG. 10E, a fluid 1044 may be driven through the fluid line 1033, though the first plate 903, through an opening in the elastic layer 907 and into a channel through the second plate 905, until it reaches the first chamber 915, configured as a valve 919. The first chamber 915 includes an upper, rounded portion (pressure portion) formed in the first plate and a lower, rounded portion (fluid portion) formed in the second plate and bifurcated by a portion of the elastic layer 907. The upper and lower portions of any chamber may be rounded in shape, as described here or may be cylindrical or straight walled. In this example, the valve is opened by applying negative pressure through a pressure line (not shown). The first chamber 915 is fluidly connected to a second chamber 916 that is configured as a metering chamber. In FIG. 10E the metering chamber 916 is opened by applying a negative pressure in the upper pressure-receiving portion of the bifurcated chamber. Thus, the chamber is open maximally, and the volume is known (e.g., 50 nL, 100 nL, 150 nL, 200 nL, 250 nL, 300 nL, 500 nL, etc.). An adjacent chamber 918 may also be configured as a valve, similar to 915, and may be held closed to allow the metering chamber to fill completely. In some variations the elastic layer may be partially permeable to air, removing bubbles and allowing complete filling by the fluid 1044.

As mentioned above, in some variations the microfluidic path apparatus includes one or more bubble removal chambers, and/or any of the chambers of the fluid-contacting side of the chamber may be configured as a bubble removal chamber, in which bubbles within the fluid of the fluid-containing side may be removed. A bubble removal chamber may be referred to as a vacuum cap, and may generally be configured to apply negative pressure on the opposite side of the membrane while fluid is held within the fluid-contacting side of the chamber. The membrane may be at least partially gas-permeable, as mentioned. Any of the pressure-receiving sides of the chambers within the microfluidic path devices described herein may be configured with one or more projections 988 into the upper (pressure-receiving side) of the chamber that prevent the elastic layer separating the pressure-receiving side of the chamber from the fluid-receiving side of the chamber from seating against the top of the pressure-receiving side. In FIG. 9C, the pressure-receiving side includes the elongate projection 988 into the pressure-receiving side so that the elastic layer cannot seal against the pressure-receiving side, thereby maximizing the surface area through which the vacuum applied into the pressure-receiving side may draw gas (e.g., air) through the gas-permeable elastic layer to remove bubbles from the liquid.

The projection may extend any appropriate depth into the pressure-receiving side. For example, this projection, which may be referred to as a spacer, may extend to the full depth of the pressure-receiving side, or between about 0.3 times and 1 times (e.g., between 0.4 time and 1 times, between about 0.5 times and 1 times, between about 0.6 times and 1 times, etc.) the depth of the pressure-receiving side. In some variations, more than one projection may be used. The projection may be cylindrical or may have multiple arms (e.g., extending from a vertex) in order to maximize the amount of membrane separated from the wall(s) of the pressure-receiving side, even when drawing the vacuum into the pressure-receiving side.

In some variations, the chamber formed by the pressure-receiving side and the fluid-containing side may therefore be slightly unequal in volume, as the projections into the pressure-receiving side may take up some of the volume. Thus, the elastic layer dividing the chamber may be in contact with the vacuum through a vacuum line 987, separated from the upper surface of the pressure-receiving side, as shown in FIGS. 9C, 10B and 10J-10K (described below). In operation, the vacuum cap 938, may remove or reduce a bubble within the line by holding fluid within the fluid-contacting side of the chamber and applying a negative pressure on the upper (pressure-receiving) side of the chamber. As mentioned, the elastic layer dividing the chamber into the fluid-contacting side and the pressure-receiving side may be gas permeable, so that the negative pressure removes gas from the liquid (fluidic) side by drawing gas (e.g., air, nitrogen, etc.) through the membrane overlying the fluid path. For example, the elastic layer (which may be a membrane) in the vacuum cap may be, e.g., PolyDiMethylSilicone (PDMS) elastomer film that is sufficiently gas permeable to allow remove gas from the liquid side of the membrane. Fluid chambers having a fixed volume (e.g., formed between the first plate and the second plate) as described herein may be coupled to one or more bubble removal chambers (e.g., vacuum caps, priming caps, priming valves, etc.) and/or may be configured as bubble removal chambers (e.g., vacuum caps, priming caps, priming valves, etc.). In some variations the portion of the elastic layer disposed between the first and the second surfaces forming the chamber, which divides the fluid-contacting side, e.g., in the second surface (and/or second plate) and a pressure-receiving side in the first surface (and/or first plate) may be only minimally (or not at all) deflected, so that it does not sit flush against the surface or wall of the pressure-receiving side. For example, the upper, pressure-receiving, side may be configured to include corners and/or one or more projections so that the elastic layer is left exposed, rather than seating flush against the upper, pressure-receiving side. However, the fluid-receiving side may still be curved (e.g., concave) so that the elastic layer is driven flush against it, without any holdup regions, to expel all or substantially all of the fluid in the fluid-receiving side when positive pressure is applied in the opposite pressure-receiving side.

To remove air (e.g., bubbles), the controller may hold fluid within the vacuum cap region, e.g., by blocking valves on either or both sides (entrance and exit) of the vacuum cap, e.g., by applying positive pressure to the pressure-receiving side of the valve, and may apply negative pressure to the pressure-receiving side of the vacuum cap. The absolute amount of negative pressure applied (e.g., the magnitude of the negative pressure) may be the same as or different than (e.g., less than) that applied to deflect the membrane in other chambers, and/or when applying positive pressure (e.g., the same as or different than the absolute value of the positive pressure applied to close the valve, and/or pump). Alternatively, in some variations the membrane may be configured to be deflected (e.g., deflected up), against the first surface and/or plate, e.g., to draw fluid into the enlarged fluid-contacting side of the chamber. As mentioned, the negative pressure on the pressure-receiving side of the elastic layer may be held to allow gas (e.g., air bubbles) to be removed through the membrane. The controller may receive input (e.g., from one or more optical sensors) detecting the air in the fluid-contacting side, e.g., by detecting one or more bubbles, and may apply vacuum in the vacuum cap until the air is gone. In some variations, the controller may hold fluid in the vacuum chamber for a period sufficient to remove all or some gas (e.g., 1 second or more, 5 seconds or more, 10 seconds or more, 20 seconds or more, 30 seconds or more, 1 minute or more, 1.5 minutes or more, 2 minutes or more, 5 minutes or more, between 1 second and 5 minutes, between 2 seconds and 5 minutes, between 5 seconds and 5 minutes, etc.). In FIG. 9C, the pressure may be applied through the pressure line 987 in communication with the pressure-receiving sides of the chamber formed between the first and second surface (e.g., first and second plate) of the device. The input(s) and/or output(s) to the vacuum cap 938 may be valved by one or more valves 992. In FIG. 9C, Fluid may exit the fluid-contacting side from a fluid line 989 at an opposite side of the vacuum cap.

The fluid-contacting side of the chamber of the pressure cap (as with the valves and reactors described herein) may be in fluid communication with a fluid port that fluidly connect with the fluid-contacting side of each of the chambers via one or more fluid channels, which may be in the second surface and/or plate. The pressure-receiving side of the vacuum cap may be in fluid communication with a pressure port extending through the first surface/plate (e.g., and into the surface/plate) to fluidly connect with the pressure-receiving port or side via a pressure channel extending through the second plate and along the first plate, as described herein.

FIGS. 9D-9E illustrate another variation of a vacuum cap 938'. In this example the vacuum cap may be configured so that the pressure receiving side 944 of the chamber has corners, as shown. An elastic layer 948 separates the chamber into the pressure receiving side 944 and the fluid-contacting side 946. In FIG. 9B, the elastic layer is in the neutral position. Fluid may be driven into the fluid-contacting side, and air may be removed by drawing a vacuum (negative pressure) into the pressure receiving side 944, as shown in FIG. 9E. The pressure receiving side in this example also includes a projection 988 that prevents the elastic layer 948 from laying against the wall(s) of the pressure receiving side, so that a larger surface area of the elastic layer may remain exposed, as shown in FIG. 9E, permitting more removal of air through the elastic layer. In some variations the device may include a variation of a vacuum cap configured as a priming valve or priming chamber. In this variation, fluid may be drawn into the chamber(s) of the microfluidic path device from one or more fluid depos by drawing the fluid into a channel and one or more chambers and/or a priming chamber or priming valve. FIG. 10B illustrates one example of a priming valve and FIGS. 10J-10K illustrate operation of a priming chamber or priming valve.

Figure 10F:
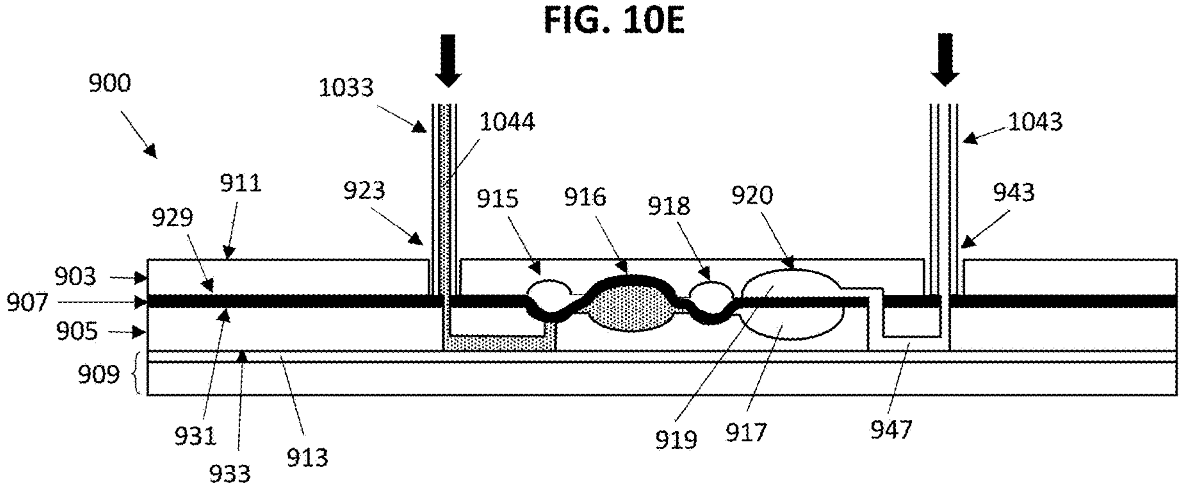
Figure 10G:
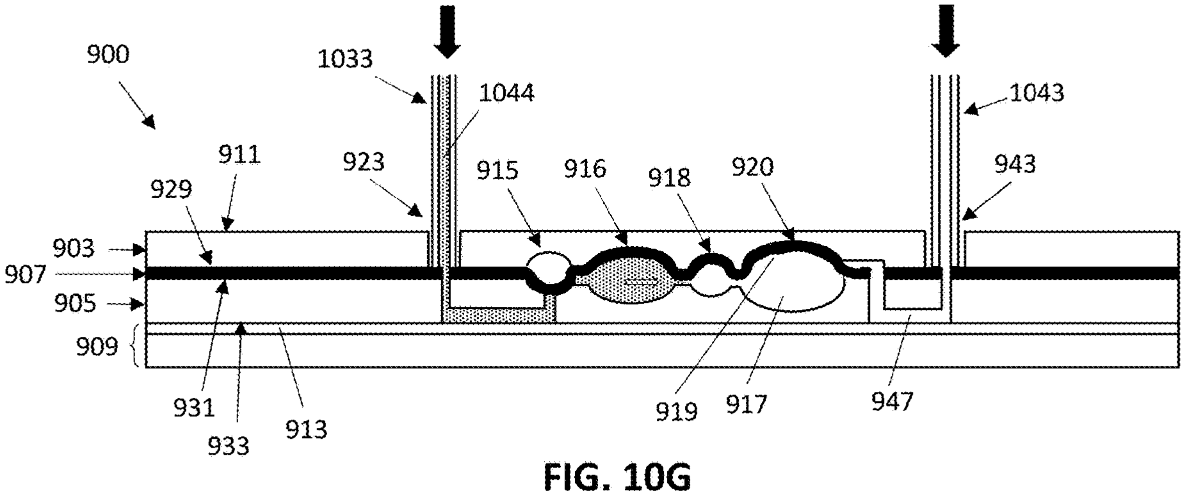
Figure 10H:
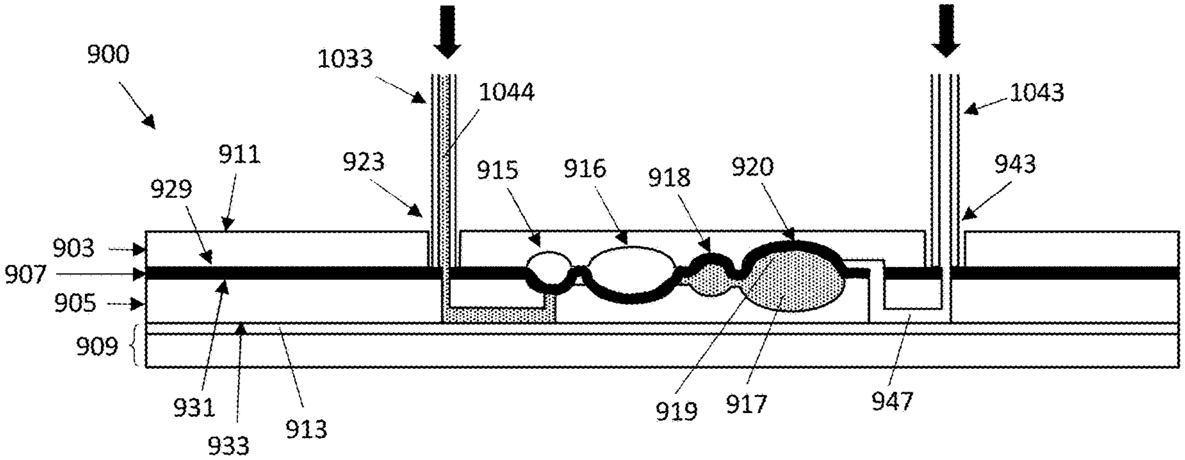
Figure 10I:
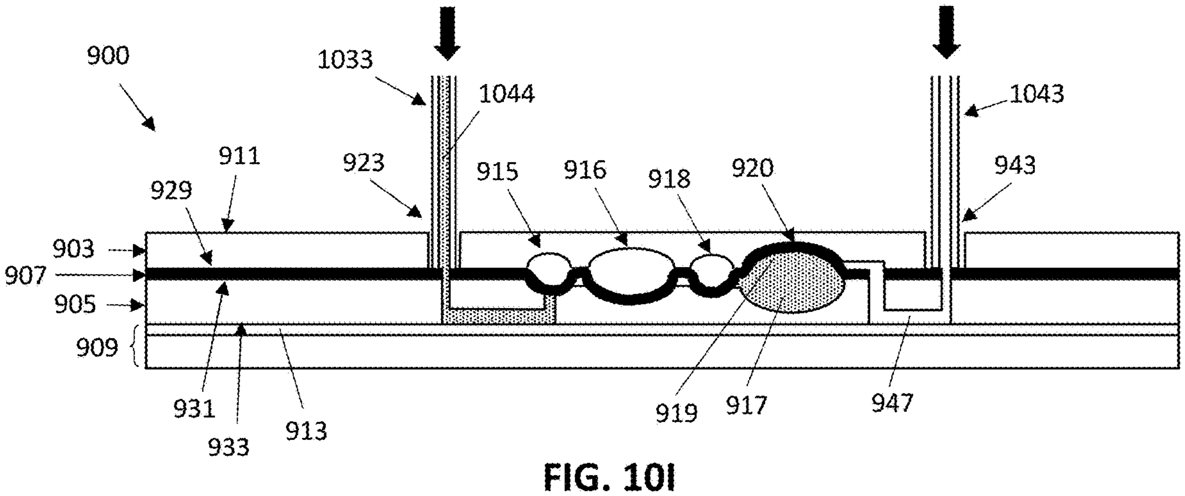
Figure 10J:
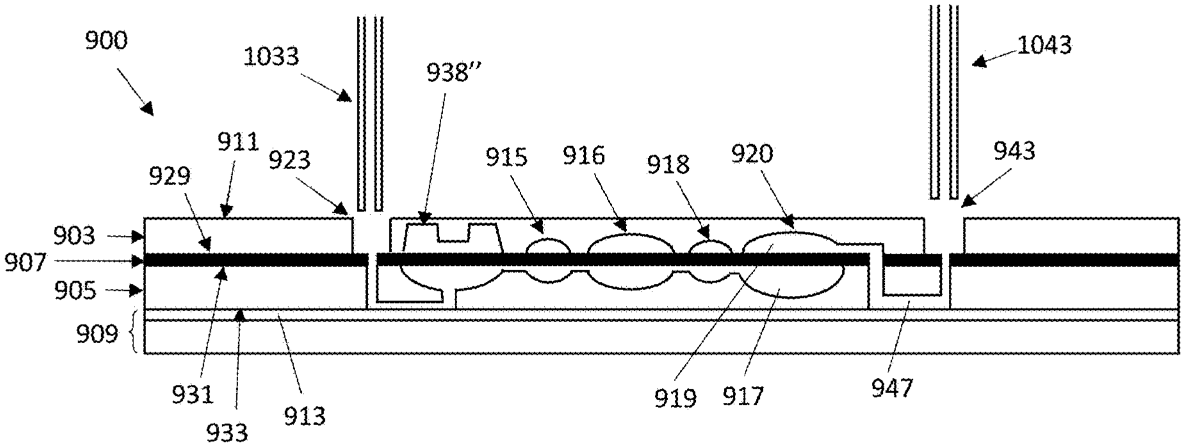
FIGS. 10J-10K illustrate a section through another example of a portion of a microfluidic path device, including a priming valve or priming cap, as described herein.
Figure 10K:
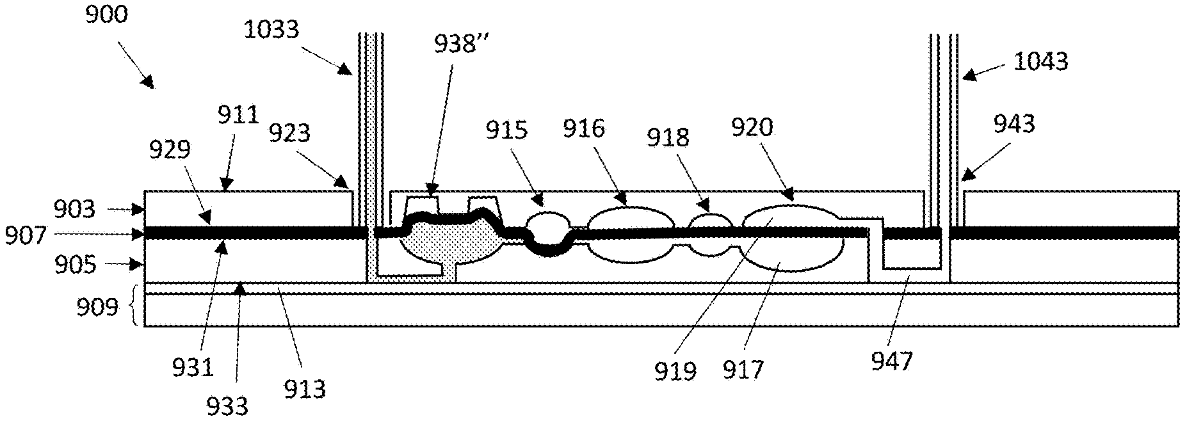
Figure 11:
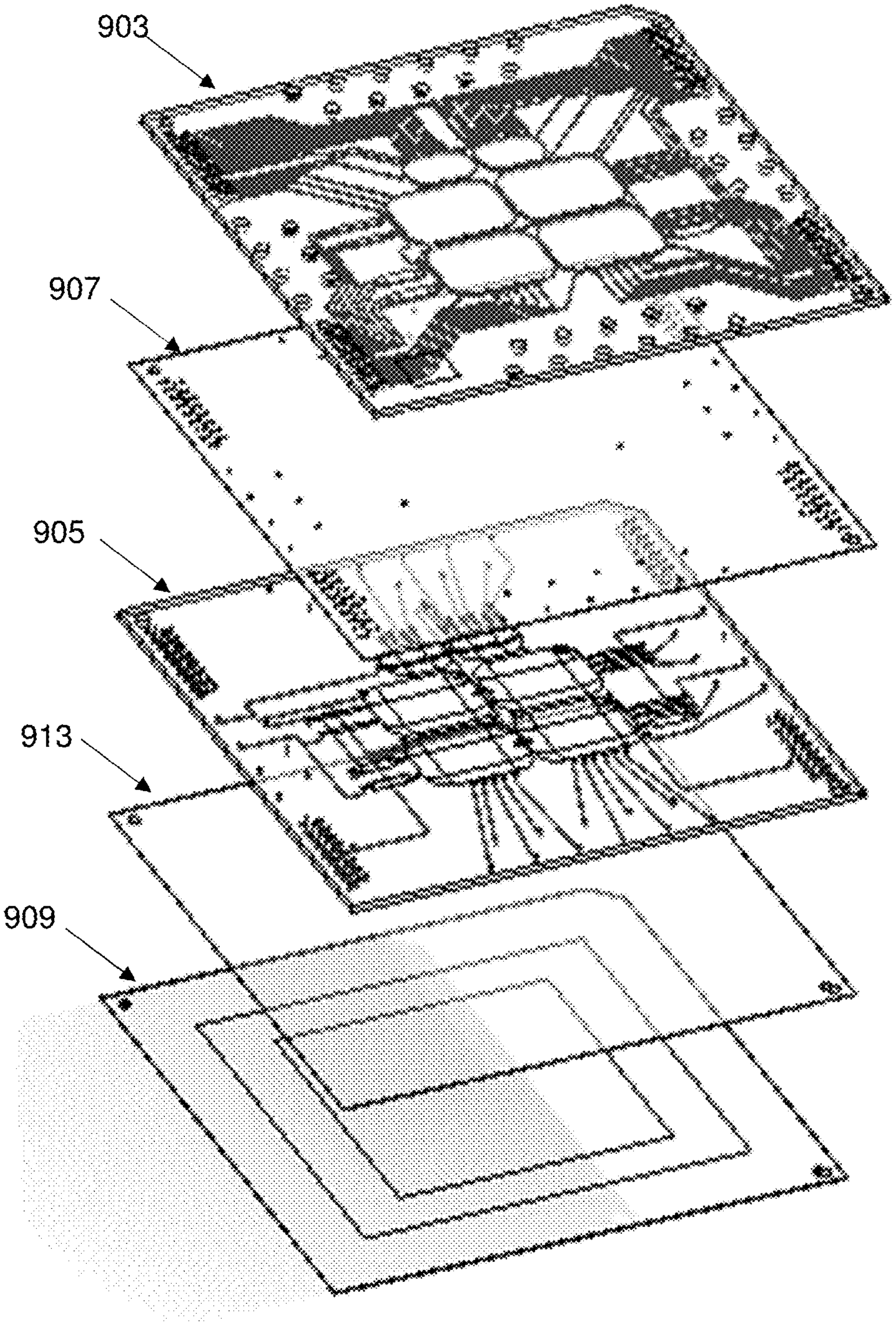
FIG. 11 is an exploded view of layers comprising a microfluidic path device according to one embodiment of the disclosure.

In FIG. 10F, the first chamber (valve 915) may be closed by applying positive pressure in the upper, pressure receiving portion of the first chamber. This limits the amount of fluid within the metering chamber 916 to the precise amount; this metered fluid may then be ejected into another chamber (e.g., a fourth chamber, configured as a mixing chamber, etc.), as shown in FIGS. 10G-10H, by opening the valve and the holding/mixing chambers (FIG. 10G), and applying positive pressure to drive fluid from the metering chamber 916 into the holding/mixing chamber 920 (FIG. 10H). The valve 918 may then be closed, as shown in FIG. 10I. The fluid in the mixing chamber may be combined with additional fluid (e.g., from other parts of the microfluidic path device, or another metered amount of the same fluidic pathway illustrated), mixed or otherwise processed in the chamber.

Any of the microfluidic path devices described herein may be microfluidic path plate devices, in which the device is substantially thin, as described above. Thus processing in/on the plate may be performed in substantially two dimensions (2D), including purification of any polynucleotides (e.g., mRNA). Purification of the polynucleotides in 2D is particularly advantageous compared to prior art techniques, which may require the use of columns and may involve steps that are difficult or impossible to perform in a closed path environment and/or in small volumes as described herein.

In addition, as illustrated in the figures (e.g., FIGS. 10A-10I), the fluid-contacting sides (and/or the pressure-receiving side) of each chamber may be configured to so that the elastic layer seats flush and without gaps to the fluid-contacting side in the second surface when a positive pressure in the pressure-receiving side drives the elastic layer against the fluid-contacting side. In some variations the fluid contacting sides and/or the pressure-receiving sides may be concave. The concavity may have a somewhat shallow, oval cross-section to permit the elastic layer to readily seat flush against the wall of the fluid contacting side (and/or pressure-receiving side). The elastic layer may push (e.g., seat) against the wall of the chamber so that there is no dead retention portion of the chamber (e.g., of the fluid-contacting side).

In addition to valves opening and/or closing channels, the first elastic layer may also be used to pump fluid in/out of a chamber, as illustrated above. For example, in some variations a chamber (e.g., accessible through a fluid channel in which valves on one or both sides are open) may be provided and allowed to fill with fluid from the fluid port. Negative pressure may be applied from a pressure port that is connected to the upper half of the bisected chamber (bisected by the elastic layer). The application of negative pressure may help prime the device by drawing fluid into the channel and removing air through the elastic layer. Thus, in any of the variations described herein, the elastic layer may be gas permeable. Once primed, fluid may be ejected out of the chamber by opening the distal valve and applying positive pressure to the opposite side of the elastic layer to drive fluid out of the chamber.

Any of the chambers 915, 916, 918, 920 in the example shown in FIGS. 10A-10I may be configured as priming chambers or priming valves (typically priming chamber are larger than priming valves; in some variations priming chambers may be metered). The priming valve may be used to draw fluid into the microfluidic path device and remove leading air by introducing the fluid (e.g., driven by positive pressure from within the one or more fluid depots attached to the microfluidic path device) and/or by applying pumping force(s) from one or more chambers (e.g., pump chambers) within the plate. In some variations fluid is moved primarily or initially by the application of positive pressure from the depots.

FIGS. 10J-10K illustrate the operation of a microfluidic device including a priming valve 938". In FIG. 10J, the microfluidic device is similar to that shown in FIGS. 10A-10I, but with the addition of the priming valve in fluid communication with the fluid line 1033 input (fluid port 923). Positive pressure applied in the fluid depot connected to the fluid line may drive fluid into the microfluidic path device, but air in the line may prevent or make it difficult to drive fluid into the device. As shown in FIG. 10K, once the microfluidic device has sealed to the fluid line 1033 and the pressure line 1043 (as described above), the fluid may be driven into the channel connected to the first, priming valve 938". A chamber or valve 915 downstream of the priming valve may be closed by the application of positive pressure within the pressure line connected to the chamber/valve 915 while negative pressure (vacuum) is applied to the priming valve, removing the leading air ahead of the liquid in the channel. The controller may then (e.g., after either allowing sufficient time based on a predetermined time and/or after sensing, e.g., optically, that air has been removed) open the closed chamber or valve 915 and allow the primed fluid to move into the device, as described for FIGS. 10B-10I, above. In some variations, particularly where the elastic layer is air-permeable, air may be removed in each of the chambers/valves, including by the use of negative pressure in the pressure-receiving valves.

Any of the apparatuses described herein may be used as described and illustrated above. For example, the methods and apparatuses described herein may be particularly helpful for use in generating mRNA therapeutics using in vitro transcription (IVT), as mentioned above. For example, the methods and apparatuses may, in a single unbroken fluid path, which provides an RNAse-free environment, synthetize a therapeutic comprising one or more mRNAs. These mRNAs may be customized to an individual patient.

EXAMPLES

Any of the apparatuses described herein may be used, for example, for manufacturing therapeutics, including in particular mRNA therapeutics. For example, a system as described herein may include an integrated hardware-software system, where each batch of therapeutic material (including both drug substance and drug product) may be produced inside dedicated, single-use, disposable microfluidic path devices (which may be referred to as chips or biochips). Therapeutic production may proceed in a sterile, closed-path system, and all the production steps may be automated to achieve a copy-exact process. This may provide a rapid turnaround of 'personalized' production batches whilst providing the high levels of reproducibility, control and quality required for the release of therapeutic material for clinical use.

Any of the apparatuses described herein may be used with one or more microfluidic path devices; in some variations different microfluidic path devices may be used sequentially or in parallel by the same apparatus to perform different portions of the procedure. For example, in one variations in which a therapeutic mRNA is produced a first microfluidic path device may be used for DNA template production as part of a Template microfluidic path device ("template biochip"). The resulting template may be transferred in a closed-path manner by the system to a second microfluidic path device (e.g., transferring from the first microfluidic path device to a depot in the system and/or directly into the second microfluidic path device). In some variations, the second microfluidic path device may be configured to perform in vitro transcription of the mRNA and the purification of that material to generate the drug substance (e.g., on an "IVT biochip" or IVT microfluidic path device). The product(s) from this second microfluidic path device may then be transferred (directly or via an intermediate depot, e.g., on the reagent storage frame) to a third microfluidic path device, such a formulation microfluidic path device (e.g., "formulation biochip"). Drug product formulation may then take place on the formulation microfluidic path device.

Each microfluidic path device may include input ports (fluid ports, pressure ports, etc.), and chambers (e.g., metering valves, reaction chambers, and purification structures) that may perform each step in the manufacturing process in a continuous and closed-path manner.

As illustrated above, the microfluidic path device may be placed into the apparatus (e.g., system), which may include any of the elements described above. For example, returning to FIG. 2C, an apparatus (e.g., system) may include a microfluidic path device 250, a microfluidic path device management system 260 or apparatus, a control panel (e.g., user input, monitoring and analysis), and in some variations a temperature-regulated (e.g., refrigerated) environment, such as a cabinet 270. The system may support all the production activities inside the microfluidic path device(s), such as the supply of reagents, fluid control, temperature control, mixing, purification and process monitoring. Manufacturing activities on the system may be are accessed and controlled through an application software.

The microfluidic path devices and apparatuses (e.g., systems) for operating them described herein may function as reactors for the manufacturing steps which are performed on three distinct microfluidic path device types, as discussed above. For example, template microfluidic path devices, IVT microfluidic path devices and formulation microfluidic path devices may be configured to include features to perform a set of unit operations in a controlled and highly reproducible manner. As described above, the microfluidic path devices are typically multilayered structures.

Figure 12C:
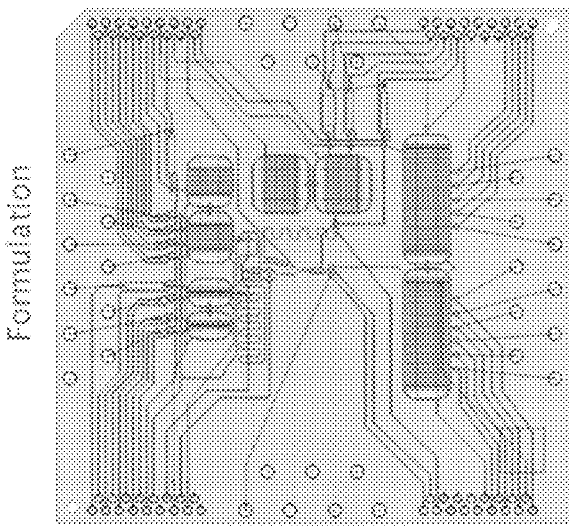
FIGS. 12A-12C illustrate examples of varieties of microfluidic path devices as described herein.
Figure 12B:
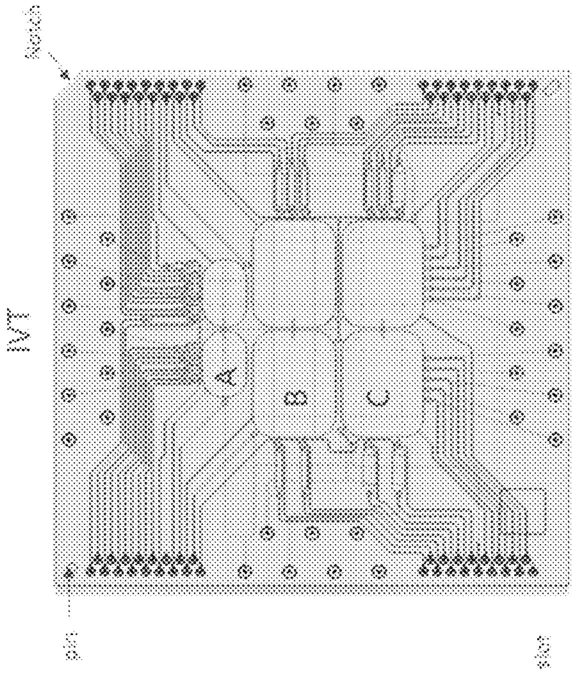
Figure 12A:
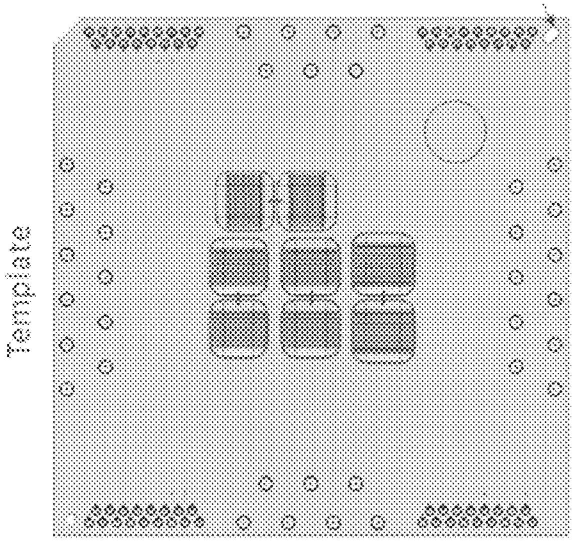

For example, a microfluidic path device may be composed of cyclic olefin copolymer (COC) and silicone. The COC layers may be made of TOPAS 5013L-10 and the silicone layers are made of Wacker Silpuran medical grade silicone. The features for each layer may be generated by machining (prototyping phase) or injection molding (production phase). Fabrication of microfluidic path devices may include: cleaning layers with 100% isopropanol, silicon oxide sputtering, oxygen plasma activation, vacuum bonding, marking (e.g., barcoding and/or RFID labeling) of the microfluidic path device, sterilization of the assembled microfluidic path device (e.g., by UV-C or Gamma Ray sterilization), and microfluidic path device storage in sterile wafer mask handling boxes. Although Oxygen Plasma exposure may sterilize the individual layers prior to assembly, later sterilization may add an additional level of sterility assurance. The different microfluidic path device types may have different designs as shown, e.g., in FIGS. 12A-12C show schematic examples of template (FIG. 12A), IVT (FIG. 12B) and formulation (FIG. 12C) microfluidic path devices. All of these example microfluidic path devices may share a similar basic architecture and number of functional elements that can be used in different configurations to carry out different protocols. Functional elements may include input ports, metering valves, pumps, reaction chambers, mixing structures and purification structures as described above.

Figure 12D:
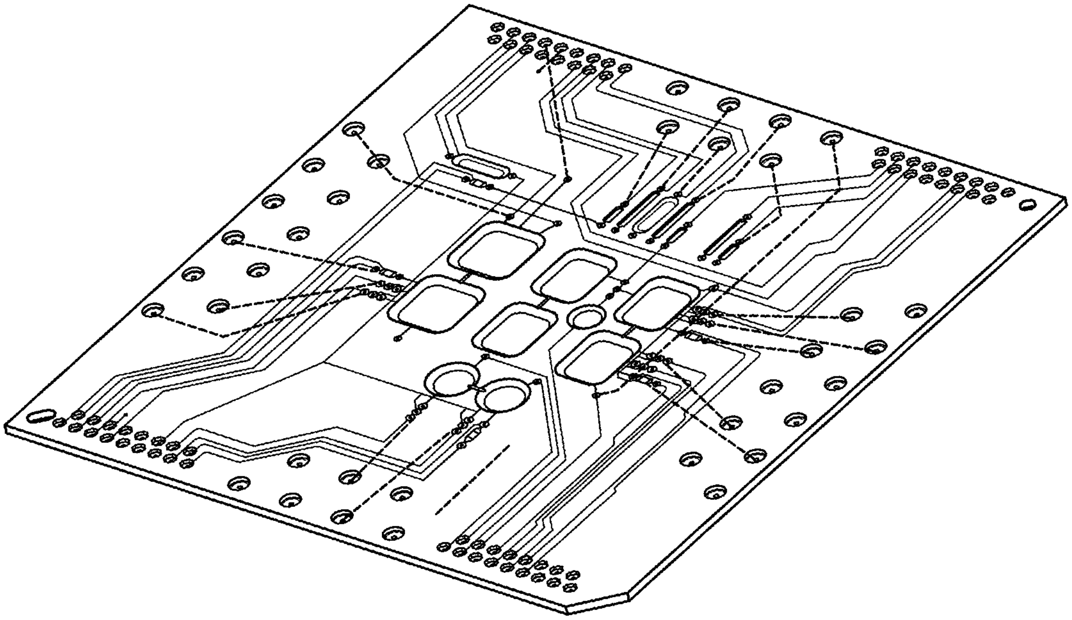
FIGS. 12D-12F illustrate examples of variations of microfluidic path devices similar to those shown in FIGS. 12A-12C.
Figure 12E:
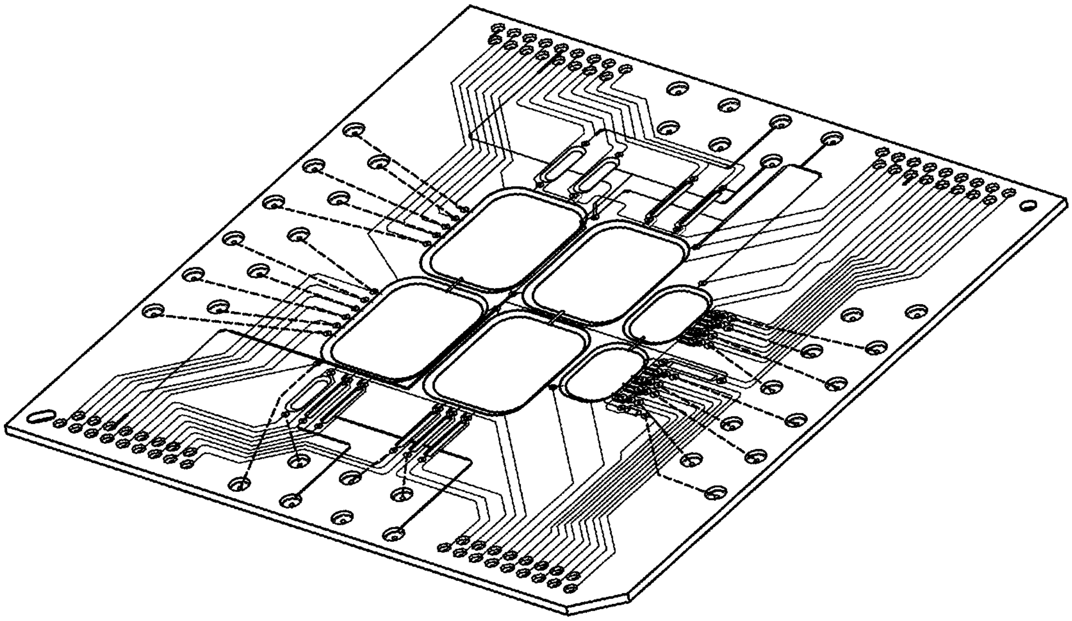
Figure 12F:
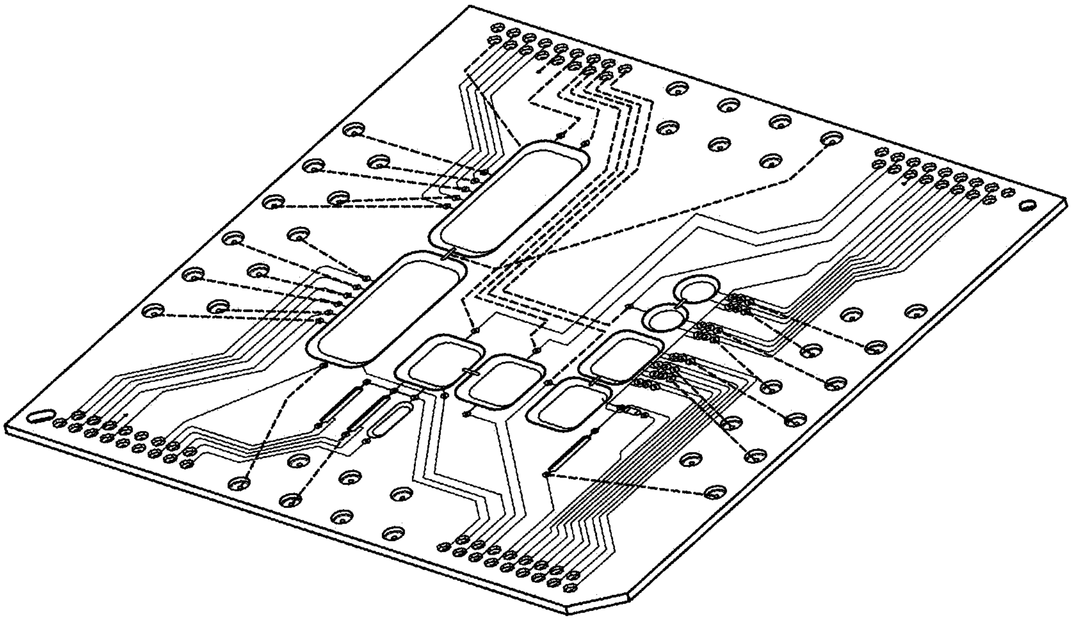

FIGS. 12D-12E illustrate alternative embodiments of the microfluidic path devices shown in FIGS. 12A-12C. FIG. 12D shows another example view of a template microfluidic path device, configured to form a template in a closed-path system as described herein; specifically the microfluidic path device shown in FIG. 12D may be used for forming a synthetic (e.g., non-bacterial) template. FIG. 12E is another example of an mRNA in vitro transcription (IVT) microfluidic path device, similar to that shown in FIG. 12B. FIG. 12F is another example of a formulation microfluidic path device similar to that shown in FIG. 12C, which may be used to encapsulate the polynucleotide (e.g., mRNA) in a delivery vehicle, as described herein. Any of these microfluidic path devices may be sterilized, e.g., using gamma irradiation, and may be packaged sterile. The microfluidic path device may be configured to process batches of predetermined sizes (e.g., about 5 mg of mRNA/2-4 days, about 50 mg of mRNA/2-4 days, about 100 mg of mRNA/2-4 days, etc.; in some variations 2 g/week).

Figure 13:
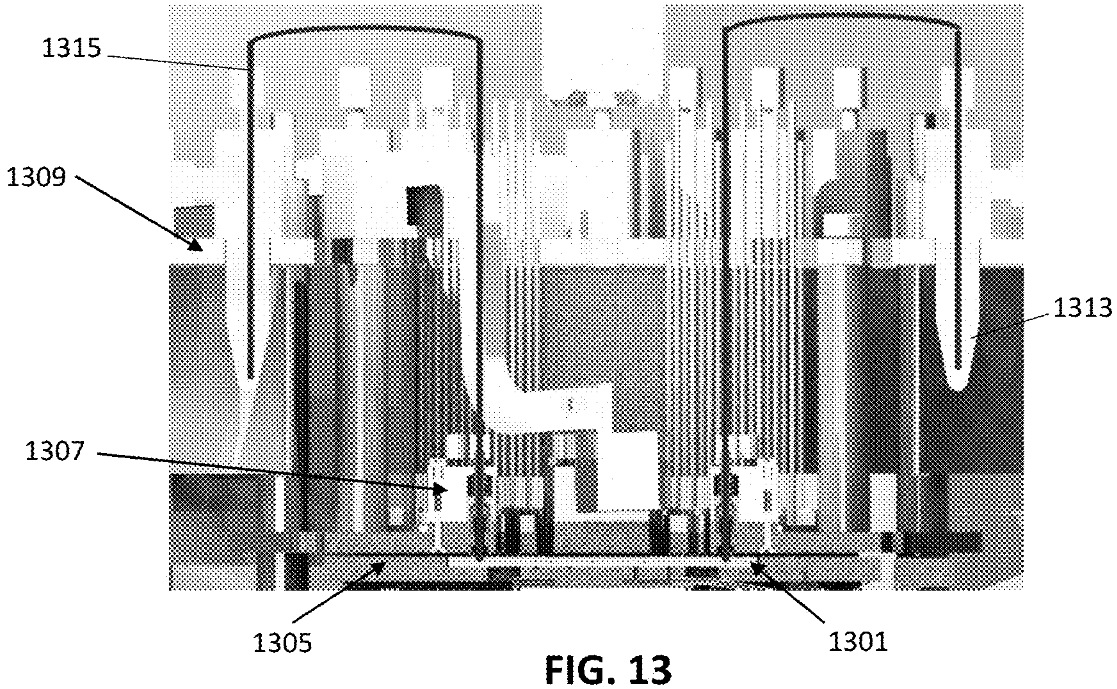
FIG. 13 show a section through an example of a microfluidic path device illustrating a closed fluidic path.

The microfluidic path devices may interface with the control system through a set of spring-loaded connections for both the reagents, as well as pneumatic lines used for managing fluid movement and valve control. The reagent and gas lines may be sealed by pressure against an elastomeric layer (elastic layer) of the microfluidic path device that creates a completely sealed path from reagent vials into the biochip and from the biochip to the export vials. FIG. 13 illustrates one example of a sealed path that may be maintained through all of the reactions inside the microfluidic path devices, effectively preventing any contact with the atmosphere and minimizing the risk of contamination. FIG. 13 shows a section through an example of a microfluidic path device mounted in a control system, in which the microfluidic path device 1301 is seated in a seating mount 1305, with a fluid interface assembly 1307 coupling fluidic and pressure lines from a reagent storage frame 1309. The closed fluid path 1315 starts from the reagent storage depots on the reagent storage frame 1309 and passes (via fluidic lines held by the fluid interface assembly against the microfluidic path device 1301) into the microfluidic path device 1301 for processing. The product then is exported off of the microfluidic path device back into a depot 1313 in the reagent storage frame.

The microfluidic path device control system (e.g., controller hardware/software, seating mount, fluid interface assembly, reagent storage frame, sensors, etc.) may provide a backbone for all the electronic and hardware components. A microfluidic path device control system may be aseptic and maintain a controlled environment. The system may also provide an interface for loading reagents and retrieving outputs, and may hold the microfluidic path device and provide a single-step connection to all the actuators.

A microfluidic path device control system may also monitor and control the operation of the device via one or more sensors, as described above. For example, a microfluidic path device control system may scan all the reagent and microfluidic path device barcodes, and may monitor fluid levels. The microfluidic path device control system may also automate all the microfluidic path device functions. As discussed above, these microfluidic path device control systems may also generate a visual recording of all process steps and/or may provide optical quality control (QC) analysis of intermediate process outputs.

The microfluidic path device control system (which may also be referred to herein as a management system) may include the components described above, such as the seating mount ("nest" or "holder") which may be configured such that microfluidic path devices are correctly aligned when in use, e.g., so that microfluidic path devices can only be inserted in a single orientation. For example, pins (e.g., two dowel pins) and/or a notch in the nest may be matched by the shape of the microfluidic path device. The microfluidic path device management system may also include vial racks to hold the reagent and export vials, a downward looking camera that records all liquid and valve movements, and product export. Side cameras on rails may capture barcodes and detect fluid levels, and a robotic arm, e.g., with magnets, may be controlled for bead manipulation. The microfluidic path device may be held in place with a vacuum chuck which ensures good contact with a thermal control (e.g., Peltier device) for temperature management. Once the microfluidic path device is in place, in some variations mating with all the connectors may be achieved in a single step by lowering the top part of the microfluidic path device management system through a dowel pin guided system.

A control panel, may be configured as a main interface for all electronic devices (e.g., CPU, Ethernet RIO device controller) as well as the valves and manifolds for pneumatic control, and pressure regulators. In some variations, the microfluidic path device control system may be held in a refrigerated container or cabinet (e.g., an ISO class 5 safety cabinet) that may provide a microbiologically safe enclosure through HEPA air filtering and air flow management and may ensure that all reagents are kept at the correct temperature through the manufacturing process. The cabinet may also be equipped with UV lamps for sterilization of the microfluidic path device and all the internal microfluidic path device management system components. In some variations, the microfluidic path device control system, may reside inside a mini environment (e.g., a 6 ft×6 ft ISO class 5 mini environment) that may itself be in a clean room (e.g., an ISO class 7 room). Operator and system interactions, including loading reagent vials and biochip may all be performed following aseptic manner. All reagents and consumables may enter the area double bagged and may be wiped clean and opened in the sterile environment, to control contamination risks.

The microfluidic path device operating system described herein may be automated by a controller. The controller may load a process protocol that defines types of microfluidic path device and reagents to use, and may ensure that the correct microfluidic path device type is being used. The controller may also capture the reagents and microfluidic path device identifiers (e.g., barcodes) and may ensure that the reagents have been released for use, are not expired and are loaded in the correct position. The controller may also execute the sequence of steps defined in the protocol, automating valve, pump, and blender actuators, temperature controllers, cameras, magnetic arms, and other required controllers. The controller may also create a batch log of events and process parameters and may record measurements from peripheral devices and in-line measurements involving light sources and detection systems. In some variations, this log may be stored as a full digital batch record in the cloud.

Figure 14:
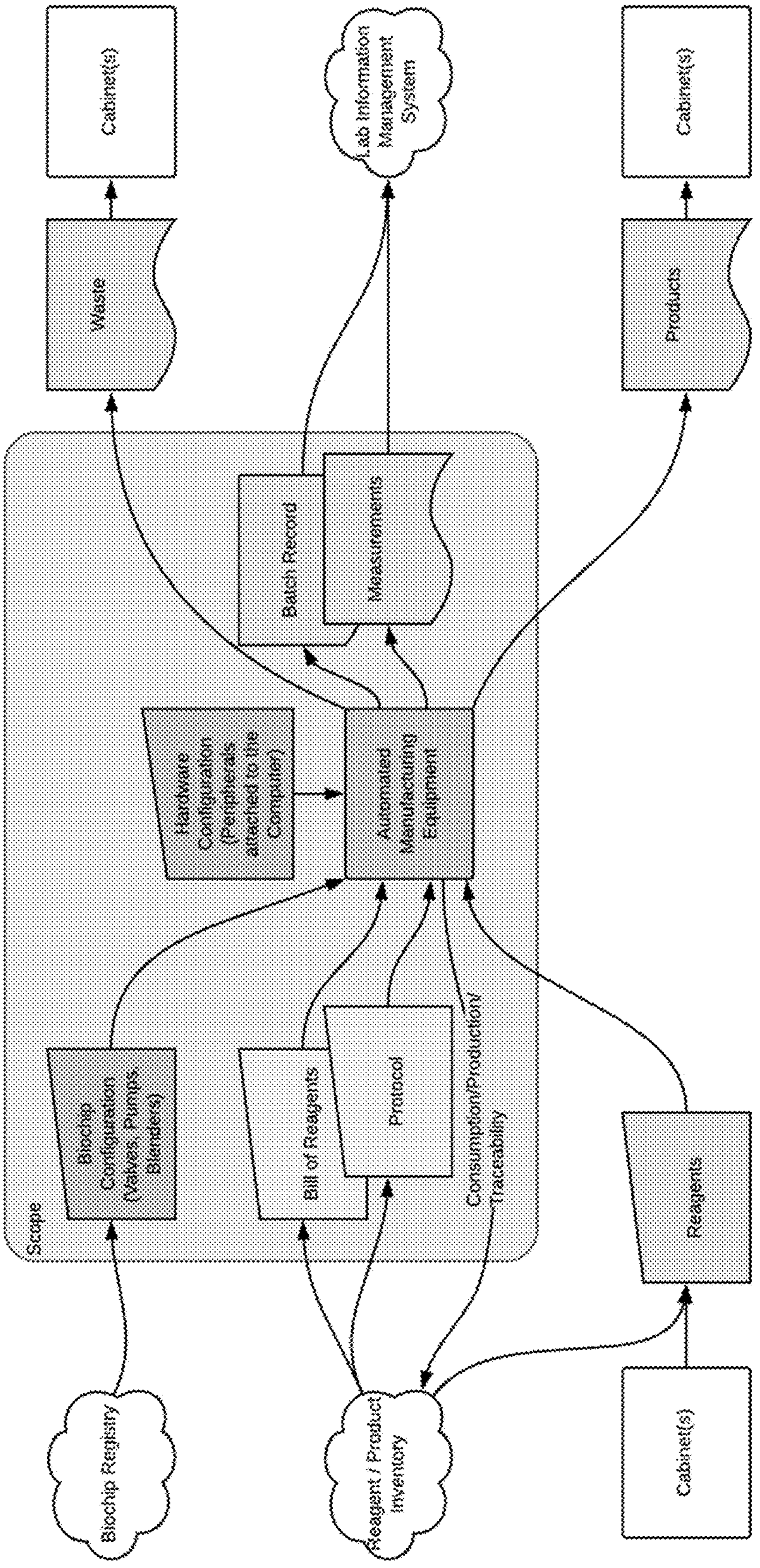
FIG. 14 schematically illustrates some of the functions of a microfluidic path device controller as described herein.

In use, an operator may select a protocol to run, e.g., from a library of preset protocols, or the user may enter a new protocol (or modify an existing protocol). From the protocol, the controller tells the operator which microfluidic path device type to use, what the vial contents should be, and where to place the vials in the nest. The operator may load the microfluidic path device, the required reagents and export vials into the system. The application may confirm the presence of the required peripherals, identifies the microfluidic path device, and scan the identifiers (e.g., barcodes) for each reagent and product vials, ensuring that vials match the bill-of-reagents for the selected protocol. After confirming the starting materials and required equipment, the controller may execute the protocol. During execution, valves and pumps are actuated to deliver reagents, reagents are blended, temperature is controlled, and reactions occur, measurements are made, and products are pumped to destination vials. At the conclusion of the protocol, a production batch record is created in the cloud. The batch-record is encrypted, and the system measurements are uploaded to the cloud. An example of a dataflow map in shown in FIG. 14, illustrating some of the functions of the controller.

As used herein, the term "processing polynucleotides" may include many types of manipulation, including but not limited to synthesizing polynucleotides, purifying polynucleotides, concentrating a solution containing polynucleotides, formulating polynucleotides, and any combination thereof. As used herein, the term "substantially horizontal" when used in reference to a surface means that the surface is within +/−X degrees of horizontal relative to ground (e.g., X may be, for example, 0.1 degree, 0.5 degrees, 1 degree, 2 degrees, 3 degrees, 5 degrees, 10 degrees, etc.).

Figure 15A:
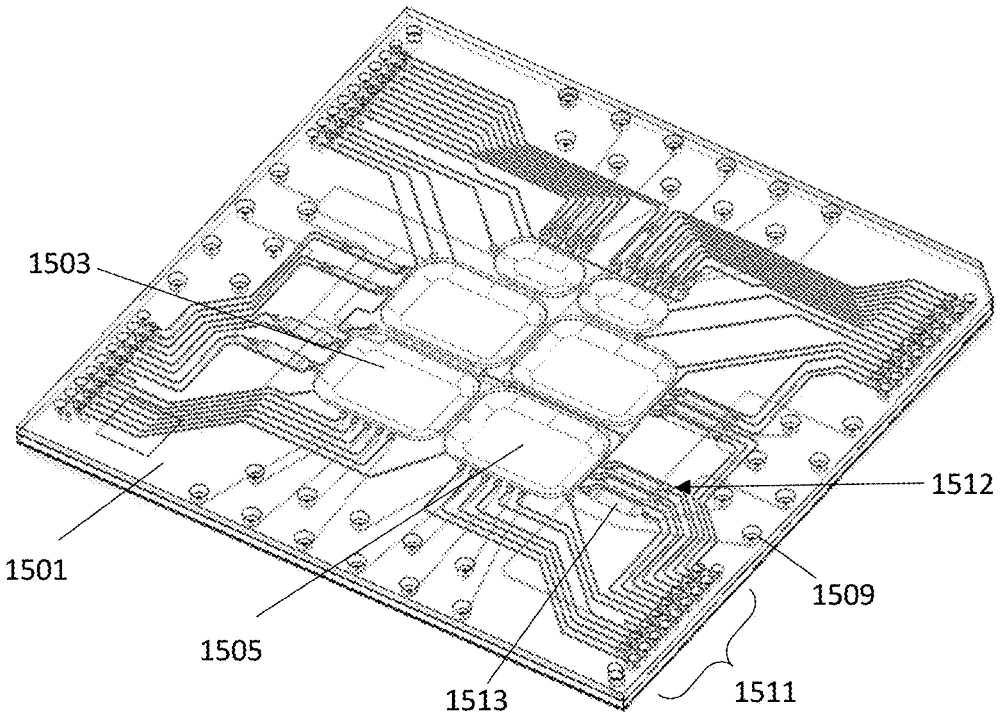
FIGS. 15A-15B show top and bottom views, respectively, of an example of a microfluidic path device including a heat spreader.
Figure 15B:
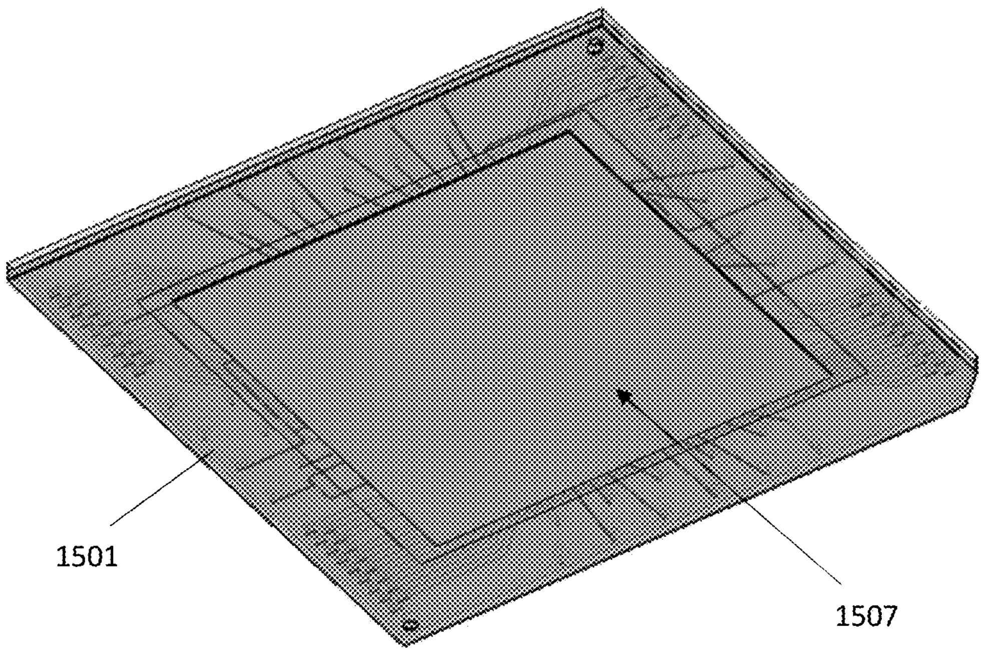

Any of the microfluidic path devices described herein may include a heat spreader on the microfluidic path device or a portion of the microfluidic path device to even out heating in this portion of the device. For example, FIGS. 15A-15B show another example of a microfluidic path device 1501 (shown here as an IVT microfluidic path device similar to that shown in FIGS. 12B and 12E, discussed above), but with a large heat spreader 1507 on the bottom side. In FIG. 15B, the microfluidic path device includes a plurality of reactors 1503, 1505 (shown as fluidically linked fluid-contacting sides of chambers formed between two surfaces of the microfluidic path device, as described above. The top of the device (shown in FIG. 15A) includes peripherally-arranged fluid ports 1509 and pressure ports 1511. The microfluidic path device shows a plurality of fluid power circuits between the pressure ports 1511, driving valves 1512, metering chambers, 1513 as well as reactors 1505, 1503. All of these chambers, valves and reactors may be formed as part of a fixed volume chamber that is formed between a first surface and a second surface in which an elastic layer divides each chamber into a fluid-contacting side (the reactor, metering chamber, etc.) in the second surface and a pressure-receiving side in the first surface (forming part of the fluid power circuit).

In the bottom view of the microfluidic path device 1501 shown in FIG. 15B, the device includes a heat spreader (e.g., a copper or other high thermal conductivity material that is attached to the bottom of the microfluidic path device). The high thermal conductivity material may be, e.g., copper, aluminum, silver, or materials like pyrolytic graphite with high thermal conductivity. The heat spreader 1507 may be mechanically attached to the microfluidic path device by fasteners and/or glued in place with adhesive. In some variation the microfluidic path device heat spreader may include or may be formed of a thermally conductive adhesive. The microfluidic path device may be thinner under the heat spreader to improve heat transfer into the material within the microfluidic path device. In some variations the heat spreader may also increase the stiffness of the microfluidic path device.

Although FIG. 15B shows a single heat spreader 1507 on the bottom of the microfluidic path device, more than one heat spreader may be used. For example, multiple heat spreaders could be used to create different temperature zones. The microfluidic path device may include a plastic material as part of the body (e.g., plate); plastic is generally a poor thermal conductor so it may maintain lateral temperature differences between different zones of the microfluidic path device. In some variations the microfluidic path device may underlie just the reactor regions.

In some variations the thermal transfer region is attached to a flat bottom and/or may be placed in pocket(s) in the part.

Figure 16B:
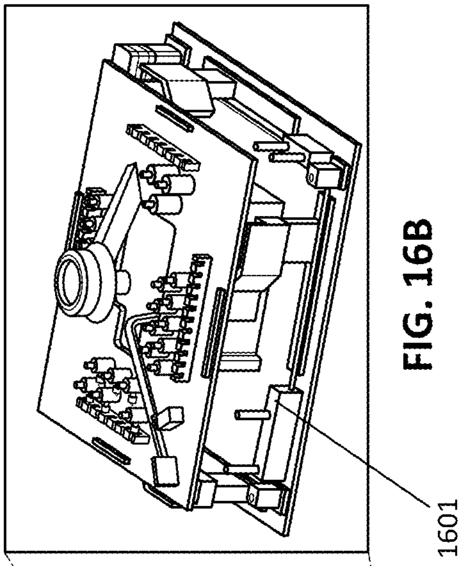
FIG. 16B illustrates the microfluidic apparatus within the class 5 cabinet.
Figure 16A:
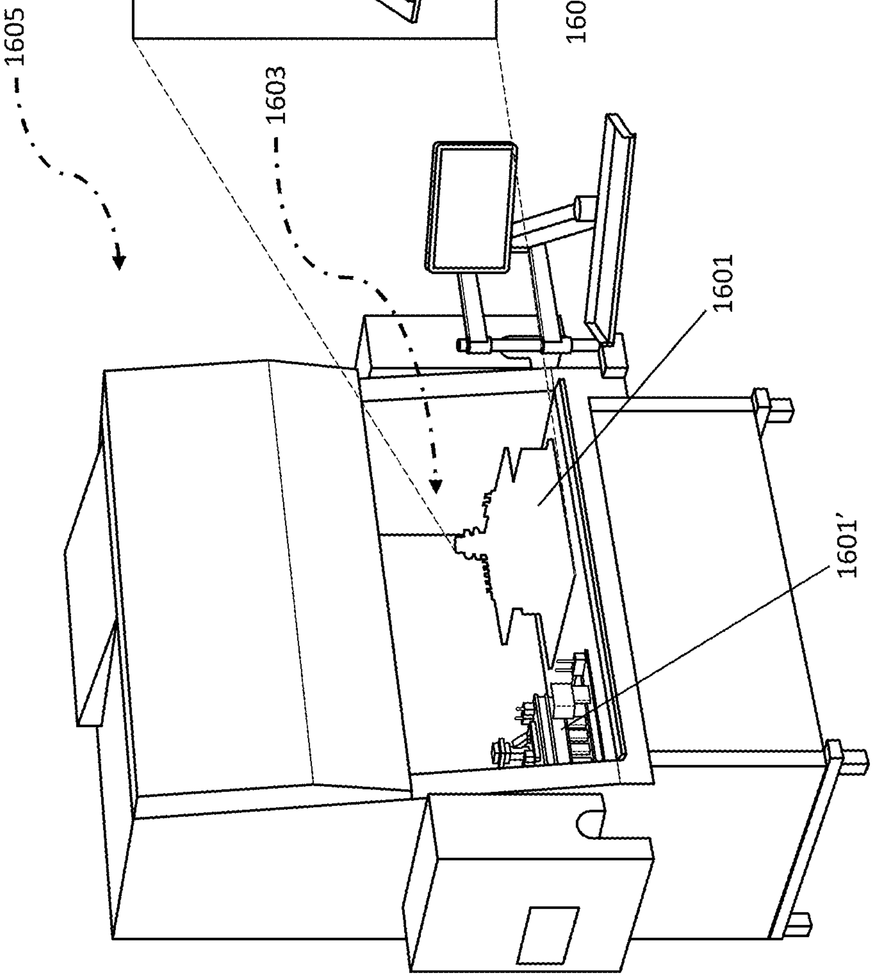
FIG. 16A shows one example of a system including a microfluidic apparatus in a class 5 isolation cabinet within a class 7 space. The system may be configured as a mini-factory.

The apparatuses described herein may include and/or may be used with one or more isolation chambers. For example in some variations the apparatuses described herein may be part of a therapeutic polynucleotide manufacturing 'factory' that may produce therapeutic polynucleotides, e.g., for delivery to a subject. The therapeutic polynucleotide may be, e.g., a therapeutic mRNA. FIGS. 16A-16B illustrate one example of an apparatus that may be used by itself as a factory apparatus or that may be used as part of a parallel manufacturing unit. In FIG. 16A the apparatus(s) 1601, 1601' may include or may be held in a class 5 isolation cabinet 1603; the isolation cabinet may itself be held within a class 7 isolation space. In FIG. 16A the cabinet includes two microfluidic control apparatuses 1601, 1601'. The apparatuses may be part of an assembly factory providing copy-exact GMP units that may automatically manufacture therapeutic polynucleotides, such as therapeutic mRNA rapidly for patient use. These apparatuses may be highly reconfigurable and allow for rapid deployment and low cost production. In some variations they may be deployed on-demand manufacturing "factory" units. In some variations these apparatuses may be set up as part of a mobile unit that may be deployed to a remote site temporarily or for a longer time period.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A microfluidic apparatus for forming a therapeutic polynucleotide, the apparatus comprising:

a seating mount for removably holding a microfluidic path device;

a plurality of pressure lines;

a plurality of fluid vials, wherein each fluid vial either comprises a fluidic line or is configured to couple with the fluidic line, wherein each fluidic line and at least a subset of the pressure lines are configured to be biased against the microfluidic path device held in the seating mount to form a closed fluid path;

an optical sensor drive configured to move one or more of a plurality of optical sensors around the seating mount or around the plurality of vials; and a controller comprising one or more processors, the one or more processors programmed to control the application of pressure through the pressure lines to drive fluidic movement in the microfluidic path device when the microfluidic path device is held in the seating mount, wherein the controller is configured to direct the synthesis of a synthetic template, direct an in vitro transcription (IVT) reaction using the template to form a therapeutic polynucleotide, and direct purification of the therapeutic polynucleotide in one or more microfluidic path devices held in the seating mount.

2. A microfluidic apparatus for forming a therapeutic polynucleotide, the apparatus comprising:

a seating mount for removably holding a microfluidic path device;

a plurality of pressure lines;

a plurality of fluid vials, wherein each fluid vial either comprises a fluidic line or is configured to couple with the fluidic line, wherein each fluidic line and at least a subset of the pressure lines are configured to be biased against the microfluidic path device held in the seating mount to form a closed fluid path;

an optical sensor drive configured to move one or more of a plurality of optical sensors around the seating mount or around the plurality of vials; and a controller comprising one or more processors, the one or more processors programmed to control the application of pressure through the pressure lines to drive fluidic movement in the microfluidic path device when the microfluidic path device is held in the seating mount, wherein the controller is configured to determine the contents of the fluid vials, transfer sub-microliter amounts of material from the fluid vials to one or more reactors in the microfluidic path device held in the seating mount, direct the synthesis of a synthetic template, direct an in vitro transcription (IVT) reaction using the template to form a therapeutic polynucleotide, and direct purification of the therapeutic polynucleotide in one or more microfluidic path devices held in the seating mount.

3. The apparatus of claim 1, further comprising a reagent storage frame holding the plurality of fluid vials.

4. The apparatus of claim 1, further comprising a plurality of optical sensors arranged to monitor fluid levels within the plurality of fluid vials and to monitor fluidic movement in the microfluidic path device when the microfluidic path device is held in the seating mount.

5. The apparatus of claim 1, further comprising a fluid interface assembly configured to hold the fluidic lines.

6. The apparatus of claim 1, further comprising a fluid interface assembly release control configured to release the fluid interface assembly from the apparatus.

7. The apparatus of claim 1, further comprising a reagent storage frame release control configured to release the reagent storage frame from the apparatus.

8. The apparatus of claim 1, further comprising a thermal control configured to modulate the temperature of at least one region of the microfluidic path device when the microfluidic path device is held in the seating mount.

9. The apparatus of claim 1, further comprising a magnetic field applicator configured to apply a magnetic field to at least one region of the microfluidic path device when the microfluidic path device is seated in the seating mount.

10. The apparatus of claim 9, wherein the magnetic field applicator comprises a control arm mounted to the reagent storage frame.

11. The apparatus of claim 1, wherein the controller is configured to detect an identifying code on the fluid vial.

12. The apparatus of claim 1, wherein the controller is configured to determine a level of a reagent held by one or more of the plurality of fluid vials.

13. The apparatus of claim 1, further comprising one or more alignment pins configured to align the microfluidic path device in the seating mount.

14. The apparatus of claim 1, further comprising an enclosure having a cover, configured to maintain the sterility of the apparatus during operation of the apparatus.

15. The apparatus of claim 1, further comprising the microfluidic path device.

16. The apparatus of claim 1, further comprising a fluid interface assembly configured to couple to the seating mount, the fluid interface assembly having a central opening through which the microfluidic path device may be imaged by one or more of a plurality of optical sensors, further wherein a distal end of each of the fluidic lines and pressure lines are arranged around a periphery of the central opening and configured to be sealed against the microfluidic device path held in the seating mount.

17. The apparatus of claim 1, further comprising a signal detector configured to detect a signal from within the microfluidic path device.

18. The apparatus of claim 17, wherein the signal is one or more of: a visible, fluorescent, UV absorbance or IR absorbance signal.

19. The apparatus of claim 17, wherein the signal detector is configured to measure a nanoparticle size distribution.

20. A microfluidic apparatus for forming a therapeutic polynucleotide, the apparatus comprising:

a seating mount for removably holding a microfluidic path device;

a plurality of pressure lines;

a plurality of fluid vials, wherein each fluid vial either comprises a fluidic line or is configured to couple with the fluidic line, wherein each fluidic line and at least a subset of the pressure lines are configured to be biased against the microfluidic path device held in the seating mount to form a closed fluid path;

a fluid interface assembly configured to couple to the seating mount, the fluid interface assembly having a central opening through which the microfluidic path device may be imaged by one or more of a plurality of optical sensors, further wherein a distal end of each of the fluidic lines and pressure lines are arranged around a periphery of the central opening and configured to be sealed against the microfluidic device path held in the seating mount; and a controller comprising one or more processors, the one or more processors programmed to control the application of pressure through the pressure lines to drive fluidic movement in the microfluidic path device when the microfluidic path device is held in the seating mount, wherein the controller is configured to direct the synthesis of a synthetic template, direct an in vitro transcription (IVT) reaction using the template to form a therapeutic polynucleotide, and direct purification of the therapeutic polynucleotide in one or more microfluidic path devices held in the seating mount.

21. The apparatus of claim 20, further comprising a reagent storage frame holding the plurality of fluid vials.

22. The apparatus of claim 20, further comprising a plurality of optical sensors arranged to monitor fluid levels within the plurality of fluid vials and to monitor fluidic movement in the microfluidic path device when the microfluidic path device is held in the seating mount.

23. The apparatus of claim 20, further comprising a fluid interface assembly configured to hold the fluidic lines.

24. The apparatus of claim 20, further comprising a fluid interface assembly release control configured to release the fluid interface assembly from the apparatus.

25. The apparatus of claim 20, further comprising a reagent storage frame release control configured to release the reagent storage frame from the apparatus.

26. The apparatus of claim 20, further comprising a thermal control configured to modulate the temperature of at least one region of the microfluidic path device when the microfluidic path device is held in the seating mount.

27. The apparatus of claim 20, further comprising a magnetic field applicator configured to apply a magnetic field to at least one region of the microfluidic path device when the microfluidic path device is seated in the seating mount.

28. The apparatus of claim 27, wherein the magnetic field applicator comprises a control arm mounted to the reagent storage frame.

29. The apparatus of claim 20, wherein the controller is configured to detect an identifying code on the fluid vial.

30. The apparatus of claim 20, wherein the controller is configured to determine a level of a reagent held by one or more of the plurality of fluid vials.

31. The apparatus of claim 20, further comprising an optical sensor drive configured to move one or more of a plurality of optical sensors around the seating mount or around the plurality of vials.

32. The apparatus of claim 20, further comprising one or more alignment pins configured to align the microfluidic path device in the seating mount.

33. The apparatus of claim 20, further comprising an enclosure having a cover, configured to maintain the sterility of the apparatus during operation of the apparatus.

34. The apparatus of claim 20, further comprising the microfluidic path device.

35. The apparatus of claim 20, further comprising a signal detector configured to detect a signal from within the microfluidic path device.

36. The apparatus of claim 35, wherein the signal is one or more of: a visible, fluorescent, UV absorbance or IR absorbance signal.

37. The apparatus of claim 35, wherein the signal detector is configured to measure a nanoparticle size distribution.

38. A microfluidic apparatus for forming a therapeutic polynucleotide, the apparatus comprising:

a seating mount for removably holding a microfluidic path device;

a plurality of pressure lines;

a plurality of fluid vials, wherein each fluid vial either comprises a fluidic line or is configured to couple with the fluidic line, wherein each fluidic line and at least a subset of the pressure lines are configured to be biased against the microfluidic path device held in the seating mount to form a closed fluid path;

a fluid interface assembly configured to couple to the seating mount, the fluid interface assembly having a central opening through which the microfluidic path device may be imaged by one or more of a plurality of optical sensors, further wherein a distal end of each of the fluidic lines and pressure lines are arranged around a periphery of the central opening and configured to be sealed against the microfluidic device path held in the seating mount; and a controller comprising one or more processors, the one or more processors programmed to control the application of pressure through the pressure lines to drive fluidic movement in the microfluidic path device when the microfluidic path device is held in the seating mount, wherein the controller is configured to determine the contents of the fluid vials, transfer sub-microliter amounts of material from the fluid vials to one or more reactors in the microfluidic path device held in the seating mount, direct the synthesis of a synthetic template, direct an in vitro transcription (IVT) reaction using the template to form a therapeutic polynucleotide, and direct purification of the therapeutic polynucleotide in one or more microfluidic path devices held in the seating mount.

* * * * *